US012577575B2

(12) United States Patent
Chen et al.

(10) Patent No.: US 12,577,575 B2
(45) **Date of Patent: *Mar. 17, 2026**

(54) METHODS AND COMPOSITIONS FOR PROMOTING NON-NATURAL AMINO ACID-CONTAINING PROTEIN PRODUCTION

(71) Applicant: Ambrx, Inc., La Jolla, CA (US)

(72) Inventors: Sigeng Chen, San Diego, CA (US); Yingchun Lu, San Diego, CA (US); Feng Tian, San Diego, CA (US)

(73) Assignee: Ambrx, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/506,836

(22) Filed: Nov. 10, 2023

(65) Prior Publication Data

US 2024/0167044 A1 May 23, 2024

Related U.S. Application Data

(63) Continuation of application No. 16/958,152, filed as application No. PCT/US2018/035764 on Jun. 2, 2018, now Pat. No. 11,851,662.

(60) Provisional application No. 62/514,754, filed on Jun. 2, 2017.

(51) Int. Cl.

*C12N 15/67* (2006.01)
*C12N 5/10* (2006.01)
*C12N 15/11* (2006.01)

(52) U.S. Cl.

CPC ............... *C12N 15/67* (2013.01); *C12N 5/10* (2013.01); *C12N 15/11* (2013.01); *C12N 2310/20* (2017.05); *C12N 2501/48* (2013.01); *C12N 2510/02* (2013.01)

(58) Field of Classification Search

CPC .......... C12N 15/67; C12N 5/10; C12N 15/11; C12N 2310/20; C12N 2501/48; C12N 2510/02; C12N 15/113; C12N 15/85; C12N 5/0682; C12N 9/93; C12N 2800/107; A61K 39/00; A61K 39/395; C07K 16/2875; C07K 16/3069; C07K 16/32; C12Y 601/01

See application file for complete search history.

(56) References Cited

U.S. PATENT DOCUMENTS

| | | | |
|---|---|---|---|
| 7,083,970 | B2 | 8/2006 | Schultz |
| 7,632,823 | B2 | 12/2009 | Tian |
| 7,736,872 | B2 | 6/2010 | Paulsel et al. |
| 7,829,310 | B2 | 11/2010 | Paulsel et al. |
| 7,838,265 | B2 | 11/2010 | Paulsel et al. |
| 7,846,689 | B2 | 12/2010 | Paulsel et al. |
| 7,858,344 | B2 | 12/2010 | Paulsel et al. |
| 7,883,866 | B2 | 2/2011 | Paulsel et al. |
| 8,420,792 | B2 | 4/2013 | Tian et al. |
| 9,133,495 | B2 | 9/2015 | Tian et al. |
| 9,586,988 | B2 | 3/2017 | Miao et al. |
| 11,851,662 | B2 | 12/2023 | Chen et al. |
| 2004/0198637 | A1 | 10/2004 | Schultz et al. |
| 2008/0254540 | A1 | 10/2008 | Wang |
| 2010/0003756 | A1 | 1/2010 | Collingwood et al. |
| 2012/0077224 | A1 | 3/2012 | Wang |
| 2012/0141978 | A1 | 6/2012 | Kim |
| 2015/0018530 | A1 | 1/2015 | Miao et al. |
| 2015/0141624 | A1 | 5/2015 | Barnett |
| 2015/0152187 | A1 | 6/2015 | Sun et al. |
| 2015/0152190 | A1 | 6/2015 | Barnett et al. |
| 2021/0017527 | A1 | 1/2021 | Chen et al. |

FOREIGN PATENT DOCUMENTS

| | | | |
|---|---|---|---|
| CN | 101160525 | A | 4/2008 |
| JP | 2010506591 | A | 3/2010 |
| JP | 2011522564 | A | 8/2011 |
| WO | 2002086075 | A2 | 10/2002 |
| WO | 2005003294 | A2 | 1/2005 |
| WO | 2006068802 | A2 | 6/2006 |
| WO | 2007021297 | A1 | 2/2007 |
| WO | 2007070659 | A2 | 6/2007 |
| WO | 2008030612 | A2 | 3/2008 |
| WO | 2008030613 | A2 | 3/2008 |
| WO | 2008030614 | A2 | 3/2008 |
| WO | 2008073184 | A2 | 6/2008 |
| WO | 2008127900 | A1 | 10/2008 |
| WO | 2008134697 | A2 | 11/2008 |
| WO | 2009151591 | A2 | 12/2009 |
| WO | 2010141851 | A1 | 12/2010 |
| WO | 2016066995 | A1 | 5/2016 |

OTHER PUBLICATIONS

Arnold, F.H. (1993). "Protein Engineering for Unusual Environments," Current Opinion in Bitechnology 4:450-455.

Atlas, R.M. & Parks (Eds). (1993). The Handbook of Microbiological Media, CRC Press, Boca Raton, FL.

Ausubel, F.M. et al. (1999). Current Protocols in Molecular Biology, Current Protocols Supplemental through 1999.

Barker, D.G. et al. (Dec. 1982). "The Tyrosyl-tRNA Synthetase from *Escherichia coli*," FEBS Letters 150(2):419-423.

Baselga, J. et al. (Jul. 1, 1999). "Recombinant Humanized Anti-HER2 Antibody (Herceptin) Enhances the Antitumor Activity of Paclitaxel and Doxorubicin Against HER2/neu Overexpressing Human Breast Cancer Xenografts," Cancer Res. 58:2825-2831, 11 pages.

Bass, S. et al. (1988). "Mutant Trp Repressors with New DNA-Binding Specificities," Science 242:240-245.

Batzer, M.A. et al. (1991). "Enhanced Evolutionary PCR Using Oligonucleotides with Inosine at the 3'-terminus," Nucleic Acid Res. 19(18):5081, 1 page.

(Continued)

*Primary Examiner* — Iqbal H Chowdhury
(74) *Attorney, Agent, or Firm* — Morrison & Foerster LLP

(57) ABSTRACT

Disclosed herein are methods and compositions for generation of cell lines to promote unnatural amino acid-containing protein production using genome engineering technology.

27 Claims, 27 Drawing Sheets

Specification includes a Sequence Listing.

(56) References Cited

OTHER PUBLICATIONS

Begems, E. et al. (Feb. 16, 2005). "Downregulation of eRF1 by RNA Interference Increases Mis-Acylated tRNA Suppression Efficiency in Human Cells," Protein Engineering Design and Selection 17(12):821-827.
Berger, S.L. et al. (1987). Guide to Molecular Cloning Techniques, Methods in Enzymology vol. 152.
Botstein, D. et al. (Sep. 20, 1985). "Strategies and Applications of In Vitro Mutagenesis," Science 229(4719):1193-1201.
Carter, P. (1986). "Site-Directed Mutagenesis," Biochem J. 237:1-7.
Carter, P. et al. (1985). "Improved Oligonucleotide Site-Directed Mutagenesis Using M13 Vectors," Nucleic Acids Res. 13(12):4431-4443.
Carter, P. et al. (1987). "Improved Oligonucleotide-Directed Mutagenesis Using M13 Vectors," Methods in Enzymol. 154:382-403.
Chatterjee, A. et al. (Aug. 7, 2013). "A Genetically Encoded Fluorescent Probe in Mammalian Cells," Journal of Amer. Med. Soc. 135(34):12540-12543.
Chin, J.W. (Feb. 10, 2014). "Expanding and Reprogramming the Genetic Code of Cells and Animals," Ann. Review of Biochem. 83(10):379-408.
Cohen, S. et al. (2016). "Single-Plasmid-Based System for Efficient Noncanonical Amino Acid Mutagenesis in Cultured Mammalian Cells," Chem. BioChem 17:1008-1011.
Cong, L. et al. (Feb. 15, 2013). "Multiplex Genome Engineering Using CRISPR/Cas Systems," Science 339(6121):819-823, 9 pages.
Creighton, T.E. (1993). Proteins: Structures and Molecular Properties 2nd Ed., 1 page.
Dale, S.J. et al. (1996). "Oligonucleotide-Directed Random Mutagenesis Using the Phosphorothioate Method," Methods Mal. Biol. 57:369-374.
Deb, N. et al. (Aug. 1996). "Treatment of Hormone-Refractory Prostate Cancer with 90Y-CYT-356 Monoclonal Antibody," Clin. Cancer Res. 2:1289-1297.
Dougherty, D.A. (2000). "Unnatural Amino Acids as Probes of Protein Structure and Function," Current Opinion in Chemical Biology 4:645-652.
Edwards, H. et al. (Apr. 1990). "A Bacterial Amber Suppressor in *Saccharomyces cerevisiae* is Selectively Recognized by a Bacterial Aminoacyl-tRNA Synthetase," Mol. Cell. Biol. 10:1633-1641.
Edwards, H. et al. (Feb. 1991). "An *Escherichia coli* Tyrosine Transfer RNA is a Leucine-Specific Transfer RNA in the Yeast *Saccharomyces cerevisiae*," PNAS 88:1153-1156.
Eghtedarzadeh, M.K. et al. (1986). "Use of Oligonucleotides to Generate Large Deletions," Nucl. Acids Res. 4(12):5115, 1 page.
Feng, L. et al. (May 13, 2003). "Expanding tRNA Recognition of a tRNA Synthetase by a Single Amino Acid Change," PNAS, 100(10):5676-5681.
Forster, A.C. et al. (May 27, 2003). "Programming Peptidornimetic Synthetases by Translating Genetic Codes Designed de novo," PNAS 100(11):6353-6357.
Francklyn, C. et al. (2002). "Aminoacyl-tRNA Synthetases: Versatile Players in the Changing Theater of Translation," RNA 8:1363-1372.
Freshney, R.I. et al. (1994). "Culture of Animal Cells a Manual of Basic Technique," 3rd Edition, Wiley-Liss, Inc.: New York, pp. 231-241, 2 pages. (Abstract Only).
Fritz, H.-J. et al. (1988). "Oligonucleotide-Directed Construction of Mutations: A Gapped Duplex DNA Procedure Without Enzymatic Reactions in vitro," Nucl. Acids Res. 16(14):6987-6999.
Fromm, M. et al. (Sep. 1985). "Expression of Genes Transferred into Monocot and Dicot Plant Cells by Electroporation," PNAS 82:5824-5828.
Gamborg, O.L. & Phillips, G.C. (Eds), Plant Cell, Tissue and Organ Culture: Fundamental Methods Springer Lab Manual, Springer-Verlag, Berlin-Heidelberg—NY, 1995, 2 pages.
Geoffroy, M.-C. et al. (Jan. 2000). "Use of Green Fluorescent Protein to Tag Lactic Acid Bacterium Strains Under Development as Live Vaccine Vectors," App. and Environ. Microbial. 66(1):383-391.
Gherna, R. et al. (1992). (eds), ATCC Catalog of Bacteria and Bacteriophage, 1 page.
Gillman, S. (1979). "Site-Specific Mutagenesis Using Synthetic Oligodeoxyribonucleotide Primers: II. In vitro Selection of Mutant DNA," Gene 8:99-106.
Goodman, H.M. et al. (Mar. 16, 1968). "Amber Suppression: A Nucleotide Change in the Anticodon of a Tyrosine Transfer RNA," Nature 217:1019-1024.
Grav, L.M. et al. (Sep. 2015, e-pub. Apr. 30, 2015). "One-Step Generation of Triple Knockout CHO Cell Lines Using CRISPR/Cas9 and Fluorescent Enrichment," Biotechnology Journal 10(9):1446-1456.
Grundström, T. et al. (1985). "Oligonucleotide-Directed Mutagenesis by Microscale 'Shot-Gun' Gene Synthesis," Nucl. Acids Res. 13(9):3305-3316.
Hamano-Takaku, F. et al. (Dec. 22, 2000). "A Mutant *Escherichia coli* Tyrosyl-tRNA Synthetase Utilizes the Unnatural Amino Acid Azatyrosine More Efficiently than Tyrosine," Journal of Biological Chemistry 275(51):40324-40328.
Hsu, PD. et al. (Jun. 5, 2014). "Development and Applications of CRISPR-Cas9 for Genome Engineering," Cell 157(6):1262-1278, 34 pages.
Hu, S.-Z. et al. (Jul. 1, 1996). "Minibody: A Novel Engineered Anti-Carcinoembryonic Antigen Antibody Fragment (Single-Chain Fv-CH3) Which Exhibits Rapid, High-Level Targeting of Xenografts," Cancer Res. 56:3055-3061.
Hu, W.-S. (2013). Cell Culture Bioprocess Engineering.
Hudson, P.J. (Aug. 1998). "Recombinant Antibody Fragments," Curr. Opin. Biotechnol. 9(4):395-402.
International Preliminary Report on Patentability, issued Sep. 23, 2019, for PCT Application No. PCT/US2018/035764, filed Jun. 2, 2018, 11 pages.
International Search Report and Written Opinion, mailed Nov. 7, 2018, for PCT Application No. PCT/US2018/035764, filed Jun. 2, 2018, 20 pages.
Italia, J.S. et al. (Apr. 13, 2017). "Expanding the Genetic Code of Mammalian Cells," Biochem. Society Transactions 45(2):555-562.
Jinek, M. et al. (Aug. 17, 2012, e-pub. Jun. 28, 2012). "A Programmable Dual-RNA-Guided DNA Endonuclease in Adaptive Bacterial Immunity," Science 337(6096):816-821, 14 pages.
Kiga, D. et al. (Jul. 23, 2002). "An Engineered *Escherichia coli* Tyrosyl-tRNA Synthetase for Site-Specific Incorporation of an Unnatural Amino Acid into Proteins in Vertebrate Translation and it's Application in a Wheat Germ Cell-Free System," PNAS 99(15):9715-9723.
Klein, T.M. et al. (1987). "High-Velocity Microprojectiles for Delivering Nucleic Acids into Living Cells," Nature 327:70-73.
Kramer, B. et al. (Oct. 1984). "Different Base/Base Mismatches Are Corrected With Different Efficiencies by the Methyl-Directed DNA Mismatch-Repair System of *E. coli*," Cell 38(3):879-887.
Kramer, W. et al. (1984). "The Gapped Duplex DNA Approach to Oligonucleotide-Directed Mutation Construction," Nucl. Acids Res. 12(24):9441-9458.
Kramer, W. et al. (1987). "Oligonucleotide-Directed Construction of Mutations Via Gapped Duplex DNA," Methods in Enzymol. 154:350-367.
Kramer, W. et al. (1988). "Improved Enzymatic in vitro Reactions in the Gapped Duplex DNA Approach to Oligonucleotide-Directed Construction of Mutations," Nucl. Acids Res. 16(14):7207, 1 page.
Kunkel, T. A. (Jan. 1987). "Rapid and efficient Site-Specific Mutagenesis Without Phenotypic Selection," Methods Enzymol 82:488-492.
Kunkel, T.A. (1987). "The Efficiency of Oligonucleotide Directed Mutagenesis," Nucleic Acids & Molecular Biology, 12 pages.
Kunkel, T.A. et al. (1987). "Rapid and Efficient Site-Specific Mutagenesis without Phenotypic Selection," Meth. Enzymology 154:367-382.
Lajoie, M.J. et al. (Oct. 18, 2013). "Genomically Recoded Organisms Expand Biological Functions," Science 342(6156):357-360.

(56) References Cited

OTHER PUBLICATIONS

Lee, C.P. et al. (Dec. 1991). "Mutants of *Escherichia coli* Initiator tRNA that Suppress Amber Codons in *Saccharomyces cervisiae* and are Aminoacylate with Tyrosine by Yeast Extracts," PNAS 88:11378-11382.
Ling, M. et al. (1997). "Approaches to DNA Mutagenesis:An Overview," Anal. Biochem. 254(AB972428):157-178.
Liu, D.R. et al. (Apr. 1999). "Progress Toward the Evolution of an Organism with an Expanded Genetic Code," Proc. Natl. Acad. Sci. USA 96:4780-4785.
Lorimer, I.A. et al. (1995). "Random Recombination of Antibody Single Chain Fv Sequence After Fragmentation with Dansel in the Present of Mn2+," Nuclei Acids Res. 23(15):3067-3068.
Mandecki, W. et al. (Oct. 1986). "Oligonucleotide-Directed Double-Strand Break Repair in Plasmids of *Escherichia coli*: A Method for Site Specific Mutagenesis," PNAS 83:7177-7181.
Maynard, J. et al. (2000). "Antibody Engineering," Annu Rev Biomed Eng 2:339-376.
Misagahi, S. et al. (May-Jun. 2013 e-pub. Apr. 18, 2013). "Resilient Immortals, Characterizing and Utilizing BAX/BAK Deficient Chinese Hamster Ovary (CHO) Cells for High Titer Antibody Production," Biotechnology Progress 29(3):727-737.
Nakamaye, K.L. et al. (1986). "Inhibition of Restriction Endonuclease Nci I Cleavage by Phosphorothioate Groups and It's Application to Oligonucleotide-Directed Mutagenesis," Nucl. Acids Res. 14(24):9679-9698.
Nambiar, K.P. et al. (1984). "Total Synthesis and Cloning of a Gene Coding for the Ribonuclease S Protein," Science 223:1299-1301.
Nangle, L.A. et al. (Oct. 20, 2006). "Global Effects of Mistranslation from an Editing Defect in Mammalian Cells," Chem. and Bio. 13(10):1091-1100.
Ohtsuka, E. et al. (Mar. 10, 1985). "An Alternative Approach to Deoxyoligonucleotides as Hybridization Probes by Insertion of Deoxyinosine at Ambiguous Codon Positions," J. Biol. Chem. 260(5):2605-2608.
Parrish, A.R. et al. (May 3, 2012). "Expanding the Genetic Code of Caenorhabditis elegans Using Bacterial Aminoacyl-tRNA Synthetase/tRNA Pairs," ACS Chemical Biology 7:1292-1302.
Paul (1999). Fundamental Immunology 4th Ed.
Payne, G. et al. (1992). Plant Cell and Tissue Culture in Liquid Systems, John Wiley & Sons, Inc., NY, 1 page.
Ran, F.A. et al. (Nov. 2013). "Genome Engineering Using the CRISPR-Cas9 System," Nat. Protoc. 8(11):2281-2308, 48 pages.
Roberts, S. et al. (Aug. 20, 1987). "Generation of an Antibody with Enhanced Affinity and Specificity for its Antigen by Protein Engineering," Nature 328:731-734.
Rossolini, G.M. et al. (1994). "Use of Deoxyinosine-containing Primers vs Degenerate Primers for Polymerase Chain Reaction Based on Ambiguous Sequence Information," Molecular and Cellular Probes 8:91-98.
Sakamar, T.P. et al. (1988). "Total Synthesis and Expression of a Gene for the A-Subunit of Bovin Rod Outer Segment Guanine Nucleotide-Binding Protein (Transducing)," Nucl. Acids Res. 16(14):6361-6372.
Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 28 pages, (Table of Contents only).
Sayers, J.R. et al. (1988). "Strand Specific Cleavage of Phosphonothioate-Containing DNA by Reaction with Restriction Endonucleases in the Presence of Ethidium Bromide," Nucl. Acids Res. 16(3):803-814.
Sayers, J.R. et al. (1988). "5'-3' Exonucleases in Phosphonothioate-Based Oligonucleotide-Direct Mutagenesis," Nucleic Acids Res. 16(3):791-802.
Schneider, E. et al. (1995). "Functional Purification of a Bacterial ATP-Binding Cassette Transporter Protein (MalK) from the Cytoplasmic Fraction of an Overproducing Strain," Protein Expr. Purif. 6:10-14.
Scott, S.D. et al. (1998). "Rituximab: A New Therapeutic Monoclonal Antibody for Non-Hodgkin's Lymphoma," Cancer Pract. 6(3):195-197.
Sieber, V. et al. (May 2001). "Libraries of Hybrid Proteins from Distantly Related Sequences," Nature Biotechnology 19:456-460.
Smith, M. (1985). "In Vitro Mutagenesis," Ann. Rev. Genet. 19:423-462.
Stemmer, W.P.C. (Aug. 4, 1994). "Rapid Evolution of a Protein In Vitro by DNA Shuffling", Nature 370:389-391.
Stemmer, W.P.C. (Oct. 1994). "DNA Shuffling by Random Fragmentation and Reassembly: In vitro Recombination for Molecular volution," Proc. Natl. Acad. Sci. USA 91:10747-10751.
Strate et al. (Feb. 1990). "Orthoclone OKT3 as First-Line Therapy in Acute Renal Allograft Rejection," Transplant. Proc. 22:219-220.
Taylor, J.W. et al. (1985). "The Rapid Generation of Oligonucleotide-Directed Mutations as High Frequency Using Phosphorothioate-Modified DNA," Nucl. Acids res. 13(24):8765-8787.
Taylor, J.W. et al. (1985). "The Use of Phosphorothioate-Modified DNA in Restriction Enzyme Reactions to Prepare Nicked DNA," Nucl. Acids Res. 13(24):8749-8764.
Tian, F. et al. (Feb. 4, 2014). "A General Approach to Site-Specific Antibody Drug Conjugates," Proc Nat Acad Sci USA 111(5):1766-1771.
Trézéguet, V. et al. (May 1991). "A Single Base Pair Dominates Over the Novel Identity of an *Escherichia coli* Tyrosine tRNA in *Scaccharomyces cerevisae*," Molecular & Cellular Biology 11(5):2744-2751.
Wang, Q. et al. (2008, e-pub. Apr. 22, 2008). "New Methods Enabling Efficient Incorporation of Unnatural Amino Acids in Yeast," Journal of the American Chemical Society 130:6066-6067.
Wang, Q. et al. (2012). "Genetic Incorporation of Unnatural Amino Acids Into Proteins in Yeast," Methods Mol. Biol. 794:199-213.
Watson, J.D. (1992). Recombinant DNA Second Edition Scientific American Books, NY.
Wells, J.A. et al. (1985). "Cassette Mutagenesis: An Efficient Method for Generation of Multiple Mutations at Defined Sites," Gene 34(2-3):315-323.
Wells, J.A. et al. (1986). "Importance of Hydrogen-Bond Formation in Stabilizing the Transition State of Subtilisin," Phil Trans. R. Soc. Lond. A. 317:415-423.
Wentworth, P.Jr. et al. (1998). "Catalytic Antibodies," Curr. Opin. Chem. Biol., 2: 138-144.
Wolfe, L.A. et al. (1999). "Antibody-Directed Enzyme Prodrug Therapy with the T268G Mutant of Human Carboxypeptidase A1: in vitro and in vivo Studies with Prodrugs of Methotrexate and the Thymidylate Synthase Inhibitors GW1031 and GW1843," Bioconjug. Chem. 10:38-48.
Wu, R. et al. (1987). vol. 154: Recombinant DNA Part: Methods in Enzymology.
Xie, M-H. et al. (Aug. 1997). "Direct Demonstration of MuSK Involvement in Acetylcholine Receptor Clustering Through Identification of Agonist scFv," Nature Biotechnology 15(8):768-771.
Zhang, B. et al. (Jan. 28, 2016). "CRISPRi-Manipulation of Genetic Code Expansion via RF1 for Reassignment of Amber Codon in Bacteria," Scientific Reports 6:20000, 8 pages.
Zoller, M.J. et al. (1983). "Oligonucleotide-Directed Mutagenesis of DNA Fragments Cloned Into M13 Vectors," Methods Enzymol. 100:468-500.
Zoller, M.J. et al. (1987). "Oligonucleotide-Directed Mutagenesis: A Simple Method Using Two Oligonucleotide Primers and a Single-Stranded DNA Template," Methods in Enzymol. 154:329-350.
Zoller, M.J. et al. (Oct. 25, 1982). "Oligonucleotide-Directed Mutagenesis Using M13-Derived Vectors: An Efficient and General Procedure for the Production of Point Mutations in Any Fragment of DNA," Nucleic Acids Res. 10(20):6487-6500.

| | Seeding Density | Deposition Rate | Outgrowth Rate | Monoclonal Outgrowth Rate |
|---|---|---|---|---|
| FACS SCD | 1 cell/well | 63% | 53% | 49% |
| LDC | 0.5 cell/well | 72% | 65% | 32% |

| Antibody | CLD | Titer g/L | Scale |
|---|---|---|---|
| mAbF-1st | MP-Amp-LDC | 1.0 | 5 L bioreactor |
| mAbH-1st | MP-LDC-Clonepix | 0.5 | 2000 L bioreactor |

| Cell Line | Viable Cell (Q3) | Early Apoptotic Cell (Q4) | Late Apoptotic Cell (Q2) | Dead Cell (Q1) |
|---|---|---|---|---|
| CHO-S | 96% | 2.4% | 1.5% | 0.1% |
| 4E2 | 85% | 6.7% | 7.4% | 0.7% |

SEQ ID NO: 93

SEQ ID NO: 94

*Forward primer K-F*

1   CAGACAGCCT TCTCTTGCTG ACTCCCAG̲C̲T̲ ̲C̲T̲G̲A̲C̲C̲C̲A̲G̲ ̲A̲A̲C̲A̲C̲A̲G̲C̲T̲ ̲G̲C̲C̲C̲A̲C̲G̲A̲C̲ ̲A̲C̲A̲G̲A̲C̲A̲G̲G̲ ̲T̲C̲T̲T̲T̲G̲C̲A̲G̲
     GTCTGTCGGA AGAGAACGAC TGAGGGTC̲G̲A̲ ̲G̲A̲C̲T̲G̲G̲G̲T̲C̲ ̲T̲T̲G̲T̲G̲T̲C̲G̲A̲ ̲C̲G̲G̲G̲T̲G̲C̲T̲G̲ ̲T̲G̲T̲C̲T̲G̲T̲C̲C̲ ̲A̲G̲A̲A̲A̲C̲G̲T̲C̲

81   T̲A̲T̲G̲T̲T̲T̲T̲C̲ ̲C̲A̲C̲T̲C̲C̲A̲C̲G̲ ̲A̲T̲C̲A̲C̲G̲A̲A̲C̲A̲ ̲A̲G̲A̲G̲A̲C̲C̲G̲C̲ ̲G̲G̲G̲C̲C̲G̲C̲T̲G̲ ̲T̲G̲T̲C̲T̲G̲C̲A̲A̲ ̲C̲C̲C̲C̲A̲C̲A̲T̲T̲ ̲C̲A̲C̲A̲A̲T̲T̲T̲C̲
     G̲A̲T̲A̲C̲A̲A̲A̲A̲G̲ ̲G̲T̲A̲G̲A̲G̲C̲T̲G̲ ̲T̲A̲G̲T̲C̲C̲T̲T̲G̲T̲ ̲T̲C̲T̲C̲T̲G̲G̲C̲G̲ ̲C̲C̲C̲G̲G̲C̲G̲A̲C̲ ̲G̲G̲G̲A̲C̲T̲G̲T̲T̲ ̲A̲G̲G̲T̲G̲T̲A̲A̲G̲ ̲G̲T̲G̲T̲T̲A̲A̲A̲G̲

Exon 2                                                    *gRNA site-I*

161  T̲C̲T̲A̲G̲A̲C̲C̲ ̲T̲A̲A̲C̲A̲G̲GTAA GCTCCAGCCC CAGGGGGACA GGTCCCGGGG GGAGGGGGAC TGGACTTATC TCTGTCATCT
     A̲G̲A̲T̲C̲T̲G̲G̲ ̲A̲T̲T̲G̲T̲C̲CATT CGAGGTCGGG GTCCCCTGT CCAGGGCCCC CCTCCCCCTG ACCTGAATAG AGACAGTAGA

241  CTCTCCCTTC TCAATCTGGT CCCCCCCCCA TCTGCAGTCC TATACTCCTT TCAGGACATG CCCGTCCTGT CCTTAGCACA
     GAGAGGGAAG AGTTAGACCA GGGGGGGGGT AGACGTCAGG ATATGAGGAA AGTCCTGTAC GGGCAGGACA GGAATCGTGT

321  GCCCTCCTGG CCACTGTCGA GGACGTTGGC GGTGCGGGGT AAAGTCTGCT CCTACCCCCA CCCCAGGAGA ATCCATTCTG
     CGGGAGGACC GGTGACAGCT CCTGCAACCG CCACGCCCCA TTTCAGACGA GGATGGGGGT GGGGTCCTCT TAGGTAAGAC

401  TGCCACGAGC CGGGTTCCCA ATCTCCAACT CCCGTTCTTA CAG̲C̲A̲T̲C̲T̲T̲G̲ ̲C̲G̲T̲C̲A̲G̲T̲G̲A̲ ̲A̲C̲T̲C̲G̲G̲A̲C̲T̲ ̲T̲G̲C̲T̲A̲T̲C̲A̲T̲
     ACGGTGCTCG GCCCAAGGGT TAGAGGTTGA GGGCAAGAAT GTC̲G̲T̲A̲G̲A̲A̲C̲ ̲G̲C̲A̲G̲T̲C̲A̲C̲T̲ ̲T̲G̲A̲G̲C̲C̲T̲G̲A̲ ̲A̲C̲G̲A̲T̲A̲G̲T̲A̲A̲

*gRNA site-II*                                          Exon 3

481  G̲G̲C̲A̲T̲C̲G̲C̲A̲ ̲T̲T̲A̲A̲C̲C̲G̲A̲G̲ ̲A̲T̲G̲C̲A̲G̲C̲A̲ ̲C̲A̲G̲T̲T̲C̲A̲A̲ ̲A̲T̲T̲T̲G̲C̲T̲G̲A̲ ̲G̲C̲A̲G̲C̲T̲C̲A̲G̲ ̲C̲C̲C̲A̲C̲A̲G̲T̲G̲ ̲G̲G̲A̲A̲T̲G̲C̲T̲A̲
     C̲C̲T̲T̲A̲C̲T̲G̲ ̲A̲A̲T̲G̲G̲C̲T̲T̲ ̲T̲A̲T̲G̲T̲C̲G̲T̲ ̲G̲T̲C̲A̲A̲G̲T̲T̲T̲ ̲T̲A̲A̲A̲T̲G̲A̲C̲T̲ ̲C̲G̲T̲C̲G̲A̲G̲T̲C̲ ̲G̲G̲T̲G̲T̲C̲A̲C̲ ̲C̲C̲T̲T̲A̲C̲G̲A̲T̲

561  G̲G̲A̲A̲C̲T̲T̲T̲C̲ ̲T̲C̲C̲A̲A̲C̲A̲T̲G̲ ̲C̲C̲T̲C̲G̲A̲GTA CCCACCACCA CCTGACCCAG CACACACGTG ATGGGCTCCC TGGCTGGGGA
     C̲C̲T̲T̲G̲A̲A̲A̲G̲ ̲A̲G̲G̲T̲T̲G̲T̲A̲C̲ ̲G̲G̲A̲G̲C̲T̲CAT GGGTGGTGGT GGACTGGGTC GTGTGTGCAC TACCCGAGGG ACCGACCCCT

641  CCGAGTTCGT GAACTCAGAT ACGATCCCCG CCCATCTCCC CGTCTCTGGG CCCCACTCGC TGTCTTCTGC ATACTTGCTG
     GGCTCAAGCA CTTGAGTCTA TGCTAGGGGC GGGTAGAGGG GCAGAGACCC GGGGTGAGCG ACAGAAGACG TATGAACGAC

721  TCATGCCTCT CAGGAGCTCT
     AGTACGGAGA GTCCTCGAGA

*Reverse primer K-R*

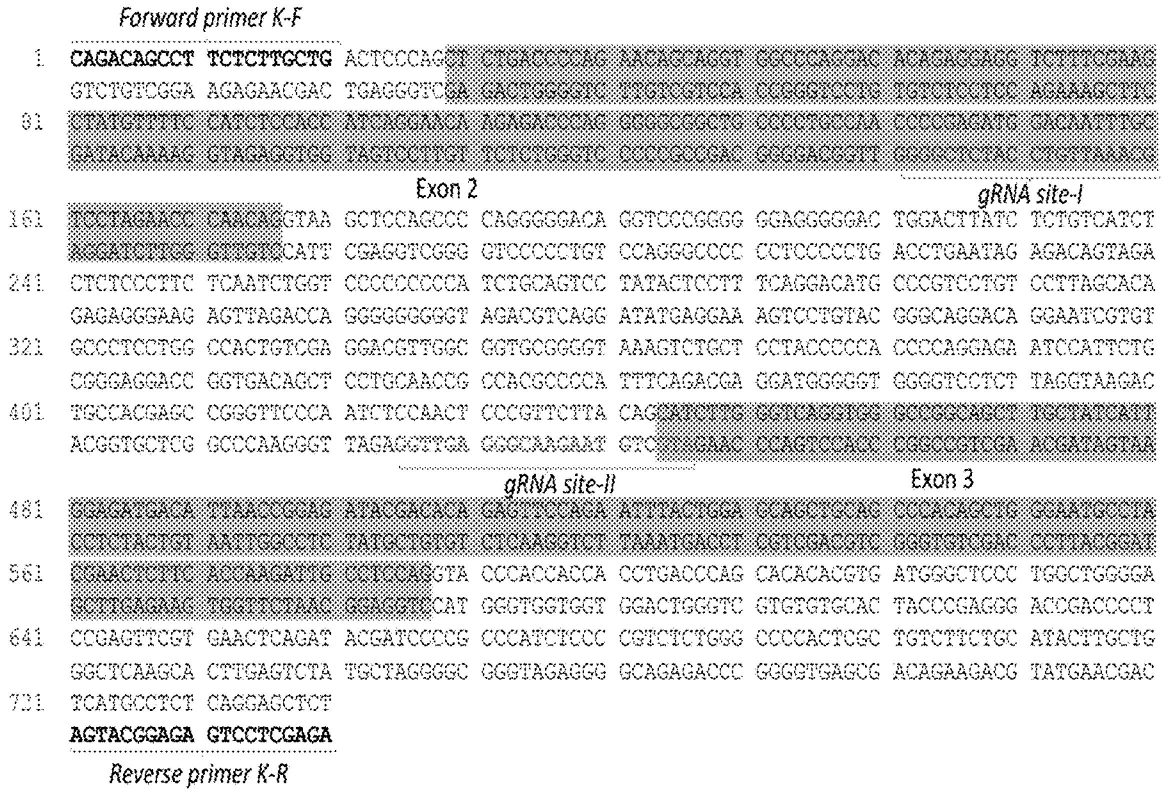

FIG. 6

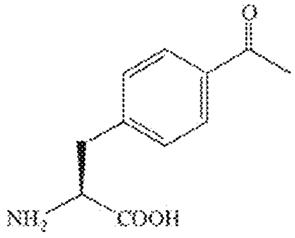
pAF
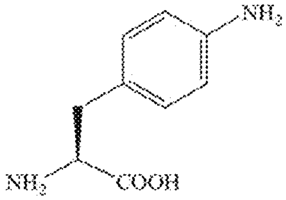
pAF2
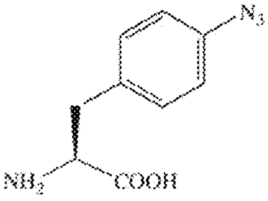
pAF3
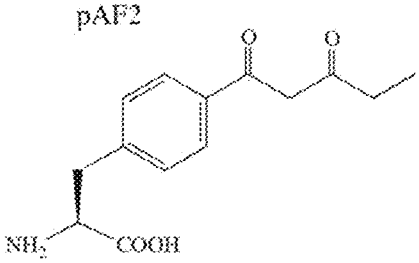
Axa 9.2
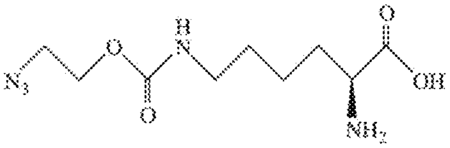
AZK
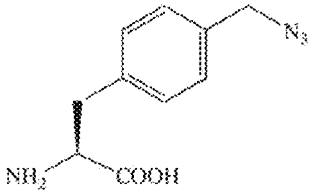
pAMF
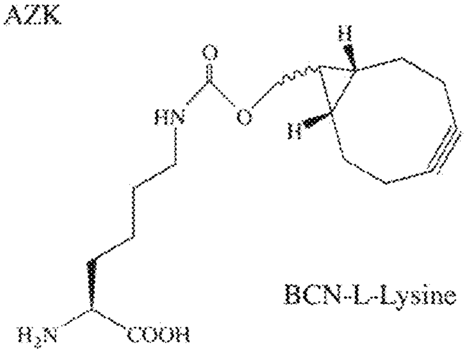
BCN-L-Lysine
FIG. 8

| SEQ ID NO: | | |
|---|---|---|
| 95 | Bak-CHO-gDNA1 | (418) |
| 96 | YA_082_K2_BakI-II | (388) |
| 97 | YA_084_K4_BakI-II | (388) |
| 98 | YA_086_K6_BakI-II | (107) |
| 99 | YA_088_K8_BakI-II | (108) |
| 100 | YA_090_K10_BakI-II | (106) |
| 101 | YA_092_K12_BakI-II | (106) |
| 102 | YA_093_K13_BakI-II | (110) |
| 103 | YA_095_K15_BakI-II | (103) |
| 104 | ZA_097_K17_BakI-II | (388) |
| 105 | ZA_098_K18_BakI-II | (388) |
| 106 | ZA_100_K20_BakI-II | (96) |
| 107 | ZA_101_K21_BakI-II | (97) |
| 108 | ZA_103_K23_BakI-II | (104) |
| 109 | ZA_105_K25_BakI-II | (389) |
| 110 | ZA_106_K26_BakI-II | (389) |
| 111 | ZA_108_K28_BakI-II | (104) |
| 112 | ZA_109_K29_BakI-II | (373) |
| 113 | ZA_110_K30_BakI-II | (104) |
| 114 | ZA_111_K31_BakI-II | (98) |
| 115 | ZA_112_K32_BakI-II | (387) |

| Cell Line | Viable Cell (Q3) | Early Apoptotic Cell (Q4) | Late Apoptotic Cell (Q2) | Dead Cell (Q1) |
|---|---|---|---|---|
| HER2-L082 | 40.1% | 11.8% | 41.8% | 6.2% |
| HER2-BB15 | 80.9% | 13.2% | 3.5% | 2.4% |

PSMA-882

| Cell line | Viable cells (Q3) | Early apoptotic cells (Q4) | Late apoptotic cells (Q2) | Dead cells (Q1) |
|---|---|---|---|---|
| PSMA-484 | 37.1% | 8.3% | 53.4% | 1.2% |
| PSMA-882 | 34.8% | 34.6% | 31.3% | 0.6% |
| PSMA-192 | 84.8% | 4.4% | 9.8% | 0.9% |
| PSMA-719 | 84.8% | 4.9% | 9.6% | 0.7% |
FIG. 17E
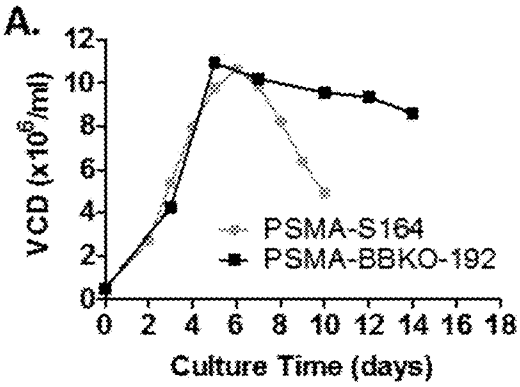
FIG. 18A
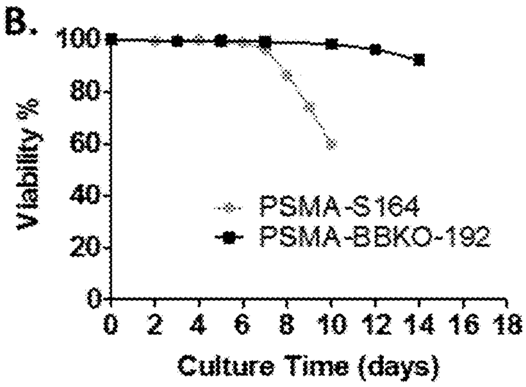
FIG. 18B
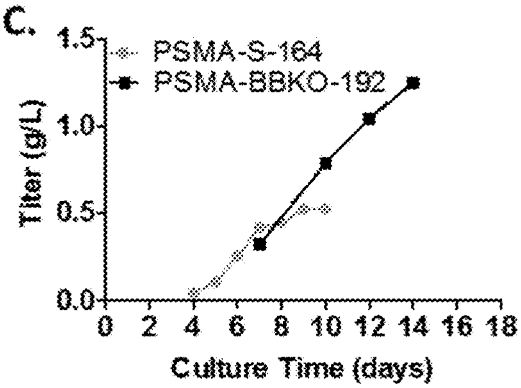
FIG. 18C

CD70-MW-108

CD70-BBKO-563

| Cell line | Viable cells (Q3) | Early Apoptotic Cells (Q4) | Late Apoptotic Cells (Q2) | Dead Cells (Q1) |
|---|---|---|---|---|
| CD70-MW-108 | 18.3% | 8.8% | 72.5% | 0.3% |
| CD70-BBKO-563 | 60.3% | 11.4% | 27.9% | 0.5% |

METHODS AND COMPOSITIONS FOR PROMOTING NON-NATURAL AMINO ACID-CONTAINING PROTEIN PRODUCTION

CROSS-REFERENCE TO RELATED APPLICATIONS

This application is a continuation of U.S. patent application Ser. No. 16/958,152, filed on Jun. 26, 2020, now U.S. Pat. No. 11,851,662 granted on Dec. 26, 2023, which is a U.S. National Stage entry under 35 U.S.C § 371 of International Application No. PCT/US2018/035764, filed on Jun. 2, 2018, which claims priority to and the benefit of U.S. Provisional Application Ser. No. 62/514,754 filed on Jun. 2, 2017; the entire contents of each of which are hereby incorporated by reference herein in their entirety.

SEQUENCE LISTING

The present application contains a Sequence Listing which has been submitted in XML format and is hereby incorporated by reference in its entirety. The XML copy, created on Jan. 22, 2024, is named AMBX-0223_02US and is 118,485 bytes in size.

FIELD OF THE INVENTION

The present disclosure pertains to the field of genome engineering and generation of cell lines to produce non-natural amino acid-containing polypeptides. The invention relates generally to the field of cell line generation, development, and production of non-natural amino acid-containing polypeptides and proteins.

BACKGROUND OF THE INVENTION

Application of chemically orthogonal directed engineered system in eukaryotic cells (EuCODE), (Feng et al., (2013), *A general approach to site-specific antibody drug conjugates, PNAS* 111(5): 1766-1771; Schultz et al., U.S. Pat. No. 7,083,970 each incorporated herein by reference), is a breakthrough in genetically producing proteins that contain non-natural amino acid. In recent years, this technology has made rapid progress in the field of antibody drug conjugation (ADC); (See for example, U.S. Patent Publications Nos. 20150018530, 20150141624, 20150152187 and 20150152190), each incorporated herein by reference. However, wider application of non-natural amino acid-containing proteins in industry has been hampered by the relative low yield in mammalian cells.

Observations indicate that a major factor likely contributing to the low yield of protein production, might be induced apoptosis caused by the excessive uncharged tRNA in the system. As known in the art, apoptosis can be initiated by various intrinsic or extrinsic factors in cell cultures, including production processes. Other challenges contributing to the low yield of protein production are cell stressors capable of activating intrinsic apoptotic pathways upon scale-up in the bioreactor processes. Therefore, there is a need, in the industry, for improved methods and compositions for promoting and increasing non-natural amino acid-containing protein production. This invention disclosure addresses these and other needs, as will be apparent upon review of the following disclosure.

SUMMARY OF THE INVENTION

Disclosed herein are methods and compositions for promotion of non-natural amino acid-containing protein production. Also disclosed herein are cell and cell lines for promoting non-natural amino acid-containing protein production. In one embodiment, the present invention disclosure provides a method of generating a cell line for incorporating a non-natural amino acid into a protein, the method comprising one or more site or region targeted for inactivation in a cell expressing a selector codon containing gene of interest, wherein cell comprises an orthogonal aminoacyl tRNA synthetase (O-RS), and an orthogonal suppressor tRNA (O-tRNA). In another embodiment the cell or cell line is eukaryotic. In other embodiments the cell or cell line is selected from COS, CHO, VERO, MDCK, WI38, V79, B14AF28-G3, BHK, HaK, NS0, SP2/0-Ag14, HeLa, or HEK293. In one other embodiment, the cell or cell line is transient, stable cell population or stable clonal cell line. In another embodiment, the cell is an isolated cell. The isolated cell is for obtaining a protein incorporating a non-natural amino acid.

In another embodiment the invention comprising a protein or polypeptide incorporating a non-natural amino acid. In other embodiments the non-natural amino acid is site specifically incorporated. In another embodiment the non-natural amino acid is para-acetyl phenylalanine, p-nitrophenylalanine, p-sulfotyrosine, p-carboxyphenylalanine, an o-nitrophenylalanine, an m-nitrophenylalanine, a p-boronyl phenylalanine, an o-boronylphenylalanine, an m-boronylphenylalanine, a p-aminophenylalanine, an o-aminophenylalanine, an m-aminophenylalanine, a p-acylphenylalanine, an o-acylphenylalanine, an m-acylphenylalanine, a p-OMe phenylalanine, an o-OMe phenylalanine, an m-OMe phenylalanine, a p-sulfophenylalanine, an o-sulfophenylalanine, an m-sulfophenylalanine, a 5-nitro His, a 3-nitro Tyr, a 2-nitro Tyr, a nitro substituted Leu, a nitro substituted His, a nitro substituted De, a nitro substituted Trp, a 2-nitro Trp, a 4-nitro Trp, a 5-nitro Trp, a 6-nitro Trp, a 7-nitro Trp, 3-aminotyrosine, 2-aminotyrosine, O-sulfotyrosine, 2-sulfooxyphenylalanine, 3-sulfooxyphenylalanine, O-carboxyphenylalanine, m-carboxyphenylalanine, p-acetyl-L-phenylalanine, a p-propargyl-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine or a p-propargyloxy-phenylalanine. In some embodiments of the present invention the non-naturally amino acid is selected from an O-methyl-L-tyrosine, an L-3-(2-naphthyl) alanine, a 3-methyl-phenylalanine, an O-4-allyl-L-tyrosine, a 4-propyl-L-tyrosine, p-propargyloxy-L-phenylalanine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, or an isopropyl-L-phenylalanine.

In other embodiments the invention provides a gene of interest or selector codon-containing gene of interest. The selector codon is a nonsense codon, a rare codon, or a fourbase codon. In another embodiment the selector codon comprises an ochre codon, an opal codon, or an amber codon. In certain embodiments, the selector codon is an amber codon.

In embodiments of the invention the gene of interest or selector codon-containing gene of interest is a biotherapeutic gene or product including a vaccine, or antibody. The gene of interest or selector codon-containing gene of interest is an antibody, scFv, scFv fusion proteins, Fc fusion proteins, Factor VII, Factor VIII, or Factor IV. In other embodiments, the gene of interest or selector codon-containing gene of interest is a cytokine, interleukin, interferon, chemokine, growth factor, hormone, and their receptors, analogs, bispecifics or fragments thereof. In another embodiment the gene of interest is HER2, CD-70, PSMA, 5T4, EGFR, TROP2, CD3, IL-2, IL-3, IL-10, IL-15, GPC3, DLL3, ROR1, leptin, FGF-21, FGF-23, HGH, FcR, insulin, TNFR1, TRAIL, EPO, and analogs, bispecifics or fragments thereof. In other embodiments, the gene of interest or selector codon-containing gene of interest is selected from the group consisting of: a cytokine, a growth factor, a growth factor receptor, an interferon, an interleukin, an inflammatory molecule, an oncogene product, a peptide hormone, a signal transduction molecule, a steroid hormone receptor, erythropoietin (EPO), insulin, human growth hormone, an Alpha-1 antitrypsin, an Angiostatin, an Antihemolytic factor, an antibody, an Apolipoprotein, an Apoprotein, an Atrial natriuretic factor, an Atrial natriuretic polypeptide, an Atrial peptide, a C—X—C chemokine, T39765, NAP-2, ENA-78, a Gro-a, a Gro-b, a Gro-c, an IP-10, a GCP-2, an NAP-4, an SDF-1, a PF4, a MIG, a Calcitonin, a c-kit ligand, a cytokine, a CC chemokine, a Monocyte chemoattractant protein-1, a Monocyte chemoattractant protein-2, a Monocyte chemoattractant protein-3, a Monocyte inflammatory protein-1 alpha, a Monocyte inflammatory protein-1 beta, RANTES, 1309, R83915, R91733, HCC1, T58847, D31065, T64262, a CD40, a CD40 ligand, a C-kit Ligand, a Collagen, a Colony stimulating factor (CSF), a Complement factor 5a, a Complement inhibitor, a Complement receptor 1, a cytokine, DHFR, an epithelial Neutrophil Activating Peptide-78, a GROα/MGSA, a GROβ, a GROγ a MIP-1α, a MIP-1δ, a MCP-1, an Epidermal Growth Factor (EGF), an epithelial Neutrophil Activating Peptide, an Erythropoietin (EPO), an Exfoliating toxin, a Factor IX, a Factor VII, a Factor VIII, a Factor X, a Fibroblast Growth Factor (FGF), a Fibrinogen, a Fibronectin, a G-CSF, a GM-CSF, a Glucocerebrosidase, a Gonadotropin, a growth factor, a growth factor receptor, a Hedgehog protein, a Hemoglobin, a Hepatocyte Growth Factor (HGF), a Hirudin, a Human serum albumin, an ICAM-1, an ICAM-1 receptor, an LFA-1, an LFA-1 receptor, an Insulin, an Insulin-like Growth Factor (IGF), an IGF-I, an IGF-II, an interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a Keratinocyte Growth Factor (KGF), a Lactoferrin, a leukemia inhibitory factor, a Luciferase, a Neurturin, a Neutrophil inhibitory factor (NIF), an oncostatin M, an Osteogenic protein, an oncogene product, a Parathyroid hormone, a PD-ECSF, a PDGF, a peptide hormone, a Human Growth Hormone, a Pleiotropin, a Protein A, a Protein G, a Pyrogenic exotoxins A, B, or C, a Relaxin, a Renin, an SCF, a Soluble complement receptor I, a Soluble I-CAM 1, a Soluble interleukin receptor, a Soluble TNF receptor, a Somatomedin, a Somatostatin, a Somatotropin, a Streptokinase, a Superantigen, a Staphylococcal enterotoxins, an SEA, an SEB, an SEC1, an SEC2, an SEC3, an SED, an SEE, a steroid hormone receptor, a Superoxide dismutase (SOD), a Toxic shock syndrome toxin, a Thymosin alpha 1, a Tissue plasminogen activator, a tumor growth factor (TGF), a TGF-α, a TGF-β, a Tumor Necrosis Factor, a Tumor Necrosis Factor alpha, a Tumor necrosis factor beta, a Tumor necrosis factor receptor (TNFR), a VLA-4 protein, a VCAM-1 protein, a Vascular Endothelial Growth Factor (VEGEF), a Urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, a SCF/c-Kit, a CD40 L/CD40, a VLA-4/VCAM-1, an ICAM-1/LFA-1, a hyalurin/CD44, and a corticosterone.

In other embodiments the invention provides one or more site or region targeted for inactivation, ablation, disruption or knockout. The one or more site or region targeted for inactivation is GS, Bcl-2, IGFBP4, AQP1, Maf1, eRF1, FUT8, P53, Caspase 3, UPF1, Smg1, Smac/DIABLO, Apaf-1, Caspase-6, Caspase-7, Caspase-9, Caspase-10, PARP, Alpha fodrin, NuMA, AIF, CAD, Puma, Noxa, 14-3-3, Aven, Myc, or HtrA2/Omi. In one embodiment, the site or region targeted for inactivation is an extrinsic selection marker gene. In another embodiment the selection marker gene is Zeocin, Hygromycin, or Puromycin. In another embodiment the site or region targeted for inactivation is a Bcl-2 site or region. In another embodiment the site or region targeted for inactivation is Bax or Bak. In other embodiments the site or region target for inactivation is fully or partially inactivated. A partially inactivated, disrupted, knocked out or ablated site or region may include a site or region that is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, inactivated, disrupted, knocked-out or ablated.

In another embodiment, the invention provides a cell or cell line for incorporating a non-natural amino acid into a protein, the cell expressing a selector codon-containing gene of interest, wherein the gene of interest comprises an orthogonal aminoacyl tRNA synthetase (O-RS), and an orthogonal suppressor tRNA (O-tRNA); and wherein the cell comprises one or more site or region targeted for inactivation.

In another embodiment, the invention provides a cell or cell line for incorporating a non-natural amino acid into a protein, comprising an orthogonal aminoacyl tRNA synthetase (O-RS), an orthogonal suppressor tRNA (O-tRNA), and wherein the cell comprises one or more site or region targeted for inactivation.

In other embodiments, the invention provides a cell or cell line expressing a gene of interest, the gene of interest comprising an orthogonal aminoacyl tRNA synthetase (O-RS), an orthogonal suppressor tRNA (O-tRNA), wherein the cell comprises one or more site or region targeted for inactivation.

In another embodiment, the invention provides a method of decreasing or reducing apoptosis in a cell comprising an orthogonal aminoacyl tRNA synthetase (O-RS) and an orthogonal suppressor tRNA (O-tRNA), the method comprising targeting for inactivation one or more pro-apoptotic site or region in the cell. In another embodiment the invention provides a cell or cell line for decreasing or reducing apoptosis a cell or cell line.

In another embodiment, the invention provides a method of generating a cell for incorporating a non-natural amino acid into a protein, the method comprising: providing a nucleic acid molecule capable of inactivating one or more site or region target for inactivation in a cell, the cell expressing a selector codon-containing gene of interest; and introducing the nucleic acid molecule into the cell expressing the selector codon-containing gene of interest comprising an orthogonal aminoacyl tRNA synthetase (O-RS), and an orthogonal suppressor tRNA (O-tRNA). In other embodiments, the nucleic acid molecule is selected from SEQ. ID NOs. 1-42. In another embodiment the nucleic acid molecule inactivates one or more site or region targeted for inactivation. In one other embodiment the one or more site or region targeted for inactivation is the same or different.

In another embodiment, the invention provides a method or cell or cell line for improving the yield of a protein or polypeptide incorporating a non-natural amino acid. In some embodiments the cell is a transient, stable cell population or stable clonal cell. In another embodiment of the invention provides a method for decreasing or reducing apoptosis in a cell. In another embodiment the invention provides a method for improving the yield of a protein or polypeptide having a non-natural amino acid site-specifically incorporated.

In another embodiment, the invention provides a method of generating a cell line comprising a non-natural amino acid, the method comprising: providing a cell line expressing a selector codon-containing gene of interest comprising an orthogonal aminoacyl tRNA synthetase (O-RS), and an orthogonal suppressor tRNA (O-tRNA); introducing into the cell a nucleic acid molecule capable of inactivating one or more target sites in the cell; and providing a non-natural amino acid to the cell.

In other embodiments, the invention provides a method of generating a cell for incorporating a non-natural amino acid into a protein, the method comprising: providing a nucleic acid molecule capable of inactivating one or more site or region target for inactivation in a cell; and introducing the nucleic acid molecule into the cell comprising an orthogonal aminoacyl tRNA synthetase (O-RS), and an orthogonal suppressor tRNA (O-tRNA).

In another embodiment, the invention provides an isolated cell or cell line according any of the claims. In other embodiments, the invention provides a method for obtaining a stable cell or cell line wherein the cell line comprises an orthogonal aminoacyl tRNA synthetase (O-RS), and an orthogonal suppressor tRNA (O-tRNA). In other embodiments, the stable cell or cell line a platform or production cell or cell line.

In another embodiment, the invention provides a method for optimizing a production cell line development wherein the cell line comprises an orthogonal aminoacyl tRNA synthetase (O-RS), and an orthogonal suppressor tRNA (O-tRNA). In one other embodiment, the invention provides an isolated polypeptide comprising a non-natural amino acid. In another embodiment, the invention provides a cell or cell line wherein the yield of the non-natural amino acid containing protein is at least 0.5-fold or greater than in the absence of inactivating one or more site or region targeted for inactivation in a cell.

In an embodiment of the invention, one or more engineered nucleic acid molecule is introduced into the cell line. The one or more engineered nucleic acid molecules may include 1, 2, 3, 4, 5, 6, 7, 8, 9, 10 or more engineered nucleic acids molecules. In other embodiments, the one or more engineered nucleic acid molecules is from the same or different target site or region. In some embodiments, the engineered nucleic acid molecules may include 1, 2, 3, 4, 5, 6, 7, 8, 9, 10 or more engineered nucleic acids molecules from the same target site or region in a cell. In some embodiments, the engineered nucleic acid molecules may include 1, 2, 3, 4, 5, 6, 7, 8, 9, 10 or more engineered nucleic acids molecules from a different target site or region.

In other embodiments, a polynucleotide recognizing one or more sites or regions targeted for inactivation, ablation, knockout or disruption in a cell may include a polynucleotide recognizing 1, 2, 3, 4, 5, 6, 7, 8, 9, 10 or more sites or regions.

In other embodiments, a cell or cell line is provided. In certain embodiments, a stable production cell line is provided. In other embodiments, the cell or cell line is eukaryotic cell or cell line. In other embodiments, the eukaryotic cell or cell line may include any of, for example, a mammalian cell, a yeast cell, a fungus cell, a plant cell, an insect cell, but not limited to such. In some embodiments the eukaryote cell or cell line is a vertebrate cell or cell line. In some embodiments the eukaryote cell or cell line is a mammalian or human cell or cell line. In other embodiments, the cell or cell line may include a COS, CHO (for example, CHO-S, CHO-K1, CHO-DG44, CHO-DUXB11, CHO-DUKX, CHOKISV), VERO, MDCK, WI38, V79, B14AF28-G3, BHK, HaK, NS0, SP2/0-Ag14, HeLa, or HEK293 (for example, HEK293-F, HEK293-H, HEK293-T) cell or cell line, but is not limited to such. In other embodiments, the cell or cell line is a CHO cell or cell line including, for example, CHO-S, CHO-K1, CHO-DG44, CHO-DUXB11, CHO-DUKX, CHOKISV. In other embodiments, the cell or cell line is a CHO-K1, MDCK or HEK293 cell or cell line. In certain embodiments, the cell or cell line is a CHO-K1 cell or cell line.

In other embodiments, optimizing, or enhancing, or increasing, or improving the yield of a non-natural amino acid-containing polypeptide or protein may include optimizing, or enhancing, or increasing, or improving the yield at least 0.5-fold, at least 1-fold, at least 2-fold, at least 3-fold, at least 4-fold, at least 5-fold, at least 6-fold, at least 7-fold, at least 8-fold, at least 9-fold, or at least 10 or more-fold greater than in the absence of a nucleic acid molecule comprising a polynucleotide recognizing one or more sites or regions targeted for inactivation, ablation, disruption or knockout.

In another embodiment, the invention provides a vaccine manufactured any of methods and cells disclosed herein.

BRIEF DESCRIPTION OF THE DRAWINGS

The novel features of the invention are set forth with particularity in the appended claims. A better understanding of the features and advantages of the present invention disclosure will be obtained by reference to the following detailed description that sets forth illustrative embodiments, in which the principles of the invention are utilized, and the accompanying drawings provided.

As shown in FIG. 4C, in comparison to CHO-S cells (viability is 96%), 4E2 exhibited excessive apoptosis (viability is 85%).

FIG. 6. CRISPR gRNA design of targeted BAK gene in CHO cells. Genomic DNA sequence of BAK gene in CHO cells in which two gRNA sequences have been annotated are depicted. Genomic DNA sequence of BAK gene, exon 2 and exon 3 are shown in gray shade. The other sequence of BAK is shown in plain text. Primers used in PCR and sequencing are shown at the beginning and the end of the sequence as forward primer and reverse primer respectively.

FIG. 8. depicts the structures of representative non-natural amino acids of the present invention.

FIG. 12A depicts Annexin V apoptosis analysis of parental cell line L082. FIG. 12B depicts BAX/BAK double knockout cell lines. BB15. FIG. 12C shows cell viability is improved from 40% to 80% after BAX and BAK knockout. Simultaneously, the apoptotic cells decrease from 53% to 17%.

FIG. 17A-FIG. 17E. Apoptosis analysis of BAX/BAK knockout anti-PSMA expressing cell lines. Annexin V apoptosis analysis of BAX/BAK double knockout cell lines PSMA-192 (FIG. 17C) and PSMA 719 (FIG. 17D) with cell viability of about 85% compared to approximately 35-37% in single KO clones (PSMA-882; FIG. 17B) or non-knockout clones (PSMA-484; FIG. 17A) are depicted, as summarized in FIG. 17E.

FIG. 18A-FIG. 18C. Promotion in anti-PSMA antibody production in BAX/BAK knockout cell lines in fed-batch culture. The protein production changes in BAX/BAK double knockout cell lines, for example, cell line PSMA-BBKO-192 is shown. Protein productions are analyzed during fed-batch production. Viable Cell Density (VCD, FIG. 18A). Cell Viability (FIG. 18B). During fed-batch production (day 14), BAX/BAK double knockout cell line showed titer increase from 500 mg/L to 1400 mg/L (FIG. 18C).

DETAILED DESCRIPTION

Figure 1A:
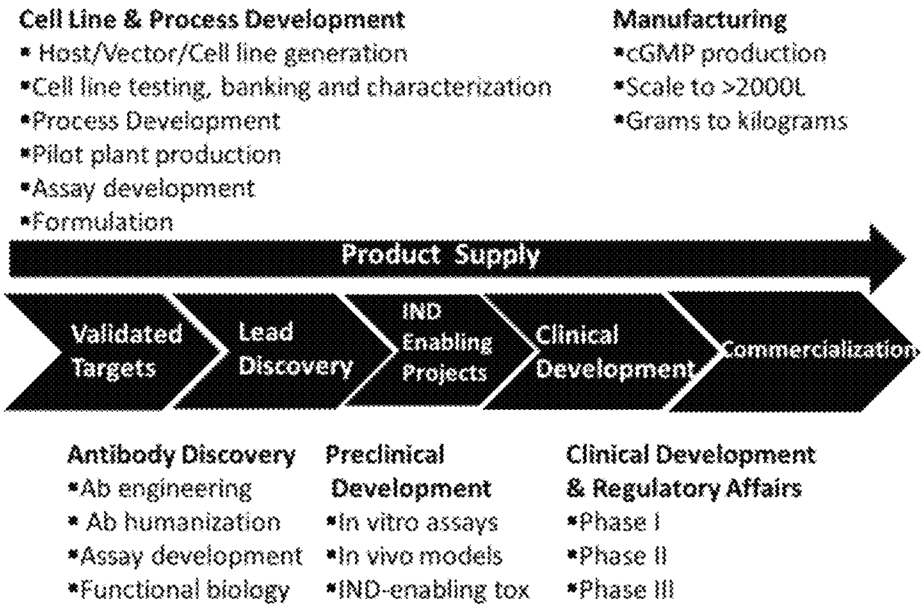
FIG. 1A-FIG. 1B. A strategy for utilizing platform cell lines in industry and in pharmaceutical companies to produce non-natural amino acid-containing proteins. The important roles of using a platform cell line in industry (FIG. 1A) and in pharmaceutical companies (FIG. 1B) are depicted.

Before describing the present invention in detail, it is to be understood that this invention is not limited to particular methodologies, or compositions, or biological systems, which can, of course, vary. It is also to be understood that the terminology used herein is for the purpose of describing particular embodiments only and is not intended to be limiting. As used in this specification and the appended claims, the singular forms "a", "an" and "the" include plural referents unless the content clearly dictates otherwise. Thus, for example, reference to "a cell" includes a combination of two or more cells and the like.

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless otherwise defined herein or below in the remainder of the specification, all technical and scientific terms used herein have the same meaning as commonly understood by those of ordinary skill in the art to which the invention belongs.

Definitions

The term "nucleic acid," as used herein, refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidates, and the like); (iii) conservatively modified variants thereof (including but not limited to, degenerate codon substitutions) and complementary sequences and sequence explicitly indicated. By way of example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. Additionally, such "polypeptides," "peptides" and "proteins" include amino acid chains of any length, including full length proteins, wherein the amino acid residues are linked by covalent peptide bonds.

As used herein, the term "orthogonal" refers to a molecule (e.g., an orthogonal tRNA (O-(RNA) and/or an orthogonal aminoacyl tRNA synthetase (O-RS)) that functions with endogenous components of a cell with reduced efficiency as compared to a corresponding molecule that is endogenous to the cell or translation system, or that fails to function with endogenous components of the cell. In the context of tRNA's and aminoacyl-tRNA synthetases, orthogonal refers to an inability or reduced efficiency, e.g., less than 20% efficient, less than 10% efficient, less than 5% efficient, or less than 1% efficient, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functional endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA in a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 50% efficiency, 60% efficiency, 70% efficiency, 75% efficiency, 80% efficiency, 90% efficiency, 95% efficiency, or 99% or more efficiency) to that of a corresponding tRNA/RS endogenous pair.

The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

The term "suppressor tRNA" is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four-base codon, a rare codon, and/or the like.

The term "translation system" refers to the collective set of components that incorporate a naturally occurring amino acid into a growing polypeptide chain (protein). Components of a translation system can include, e.g., ribosomes, tRNA's, synthetases, mRNA, amino acids, and the like. The components of the invention (e.g., ORS, OtRNA's, unnatural amino acids, etc.) can be added to an in vitro or in vivo translation system, e.g., a eukaryote cell, a vertebrate cell, e.g., a yeast cell, a mammalian cell, a plant cell, an algae cell, a fungus cell, an insect cell, and/or the like.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to compounds that have the same basic chemical structure as a naturally occurring amino acid, by way of example only, an α-carbon that is bound to a hydrogen, a carboxyl group, an amino group, and an R group. Such analogs may have modified R groups (by way of example, norleucine) or may have modified peptide backbones while still retaining the same basic chemical structure as a naturally occurring amino acid. Non-limiting examples of amino acid analogs include homoserine, norleucine, methionine sulfoxide, methionine methyl sulfonium.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence is a "conservatively modified variant" where the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M); (sec, e.g., Creighton, Proteins: Structures and Molecular Properties (W H Freeman & Co.; 2nd edition (December 1993).

As used herein, the term "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids. It is noted that reactive groups in the non-natural amino acids are not available from functional groups present in the 20 canonical amino acids. Accordingly, these reactive groups can be used to modify polypeptides site specifically and homogeneously.

The term "antibody," as used herein, includes, but is not limited to a polypeptide substantially encoded by an immunoglobulin gene or immunoglobulin genes, or fragments thereof, which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology,* 4th Ed., 1999, Raven Press, New York, for antibody structure and terminology. Antibody fragment refers to any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')2, single chain Fv (scFv), diabodies, triabodies, tetrabodies, bifunctional hybrid antibodies, CDR1, CDR2, CDR3, combinations of CDR's, variable regions, framework regions, constant regions, heavy chains, light chains, and variable regions, and alternative scaffold non-antibody molecules, bispecific antibodies, and the like (Maynard & Georgiou, 2000, Annu. Rev. Biomed. Eng. 2:339-76; Hudson, 1998, Curr. Opin. Biotechnol. 9:395-402). Another functional substructure is a single chain Fv (scFv), comprised of the variable regions of the immunoglobulin heavy and light chain, covalently connected by a peptide linker (S-z Hu et al., 1996, Cancer Research, 56, 3055-3061). These small (Mr 25,000) proteins generally retain specificity and affinity for antigen in a single polypeptide and can provide a convenient building block for larger, antigen-specific molecules. Unless specifically noted otherwise, statements and claims that use the term "antibody" or "antibodies" specifically includes "antibody fragment" and "antibody fragments."

The term "isolated," as used herein, refers to separating and removing a cell or clone from a homogenous or heterogeneous cell population. In embodiments of the present invention, the term isolated include an isolated or single cell that has been obtained from a cell culture or population of cells. A cell or clone can be selected over other cell populations or clonal populations by culturing in medium that provides some selective advantage to the desired cell or clone of interest. For example, in routine cell culture, a particular cell type can be enriched by adding specific growth factors and cytokines. This may include enriching populations of a certain lineage and differentiation stage to achieve the desired cell or clone, the use of selective media that allow specific cells to grow and inhibit others through antibiotics or specific growth inhibitors or a combination of such selection strategies as are well known to one of skill in the art. For example, selective media is often used for isolating transfected cells. Common antibiotics used for mammalian cell selection include bleomycin, puromycin and hygromycin but not limited to such. The term "isolated," as used herein, also refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. Purity and homogeneity may be determined using analytical chemistry techniques including, but not limited to, polyacrylamide gel electrophoresis or high-performance liquid chromatography. In addition, when a component of interest is isolated and is the predominant species present in a preparation, the component is described herein as substantially purified. The term "purified," as used herein, may refer to a component of interest which is at least 85% pure, at least 90% pure, at least 95% pure, at least 99% or greater pure. By way of example only, nucleic acids, polypeptides or proteins are "isolated" when such nucleic acids, polypeptides or proteins are free of at least some of the cellular components with which it is associated in the natural state, or that the nucleic acid, polypeptides, or protein has been concentrated to a level greater than the concentration of its in vivo or in vitro production. Also, by way of example, a gene is isolated when separated from open reading frames which flank the gene and encode a polypeptide or protein other than the gene of interest.

As used herein, the term "eukaryote" refers to organisms belonging to the phylogenetic domain Eucarya, including but not limited to animals (including but not limited to, mammals, insects, reptiles, birds, etc.), ciliates, plants (including but not limited to, monocots, dicots, and algae), fungi, yeasts, flagellates, microsporidia, and protists. The terms "vertebrate" and "eukaryote" may be used interchangeably herein.

Embodiments of the present invention provide a platform cell line generated from CHOK1 to stably express orthogonal suppressor tRNA/aminoacyl-tRNA synthetase pair for efficient incorporation of non-natural amino acid, provided in the media culture, into proteins in CHO cells (See for example, Tian F, et al., 2014). Production cell lines can be generated to produce non-natural amino acid incorporated proteins by transfecting amber nonsense codon containing a gene of interest in GS (glutamine synthetase) expression system into the platform cell line host. The GS expression system uses glutamine synthetase as selectable marker gene for selection of stable integration of the linked product gene into the genome of the host cell during the stable cell line development to generate manufacturing cell line. The platform cell line has been well characterized and developed with improved non-natural amino acid incorporation efficiency and clone selection efficiency. The platform cell line was pre-adapted to suspension growth for rapid progression into bioreactors.

From the industry perspective, platform cell line can be used to provide stage-appropriate material to support every stage of drug development, but also to generates stable, well-characterized production cell line(s) prior to introduction of the product to the clinics and commercialization. Therefore, in pharmaceutical companies, cell line and cell culture group are closely involved in cross-function activities. For example, the discovery team identifies targets and generates candidate molecules. Transient transfection and stable pool generation in platform cell line host are conducted to evaluate the expression of candidate molecules and provide material for development studies (purification, conjugation and analytical method development) and functional assay to identify a lead molecule. Once a lead molecule is selected, the stable cell lines are then generated to produce high yield product with desirable quality attributes. The top clone selection involves cell line, process development and analytical functions to identify stable, well-characterized production cell line scalable to industry standard manufacturing to support clinical trial and commercialization. Cell culture process development starts with cell line generation and selection, followed by process and media optimization in small scale systems, including 96-well plates, shake flasks and bench-scale bioreactors, for high throughput screening purposes. Once conditions are defined, the process is often transferred to a pilot scale to test scalability and produce material for preclinical toxicology studies, then large scale manufacturing for production of clinical material under current good manufacturing practices (cGMP) regulation. Once development of commercial cell culture process for production of a biological product is completed at the laboratory and pilot scales, the commercialization process begins with process characterization, scale-up, technology transfer, and validation of the manufacturing process. Most such methods for cell line development, cell culture process development and manufacturing, or such alternative are well known in the art. See for example, Weishou Hu, et al., Cell Culture Process Engineering (2013).

In the present invention, stable cell line development strategy has been implemented to obtain production cell line with 5-10 PCD in 3-4 months and 20-30 PCD in 6 months using the platform cell line as parental cells. See also, Examples herein. The production cell lines passed the stability study for at least 8 weeks affording up to 12,000 L bioreactor manufacturing scale. A clone used for master cell bank (MCB) was chosen based on growth, productivity and product quality. Further cell line engineering using CRISPR/Cas9 genome editing technology in production cell line yielding 0.5 g/L or 500 mg/L demonstrated to improve cell growth and increase the volumetric titer up to 1.5 g/L or 1500 mg/L. A fed-batch process developed for the production cell line demonstrated scalability at 2000 L single use bioreactor (SUB) scale for clinical material preparation. Thus, in other embodiments, the present invention provides for the optimization of high producing cell line development. Such optimization of high production cell line development can be achieved by methods and techniques well known in the art, including but not limited to FACS-dependent single cell deposition, CRISPR knock out procedure, and production scale-up.

Methodology and Techniques

The present invention employs a number of conventional techniques in molecular biology, cell culture, biochemistry, and the like, well known within the art. Methods and techniques for cell line development, cell culture process development and manufacturing, are well described in, for example, Weishou Hu, et al., Cell Culture Process Engineering (2013). General texts which describe molecular biological techniques include Berger and Kimmel, Guide to Molecular Cloning Techniques, Methods in Enzymology volume 152 Academic Press, Inc., San Diego, CA (Berger); Sambrook et al., Molecular Cloning—A Laboratory Manual (2nd Ed.), Vol. 1-3, Cold Spring Harbor Laboratory, Cold Spring Harbor, New York, 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel")). These texts describe the use of vectors, promoters and many other relevant topics related to, for example, the generation of genes that include selector codons for production of proteins that include unnatural amino acids, orthogonal tRNA's, orthogonal synthetases, and pairs thereof.

Other procedures may be found in the following publications and references cited within: Ling et al., *Approaches to DNA mutagenesis: an overview*, Anal Biochem. 254(2): 157-178 (1997); Dale et al., *Oligonucleotide-directed random mutagenesis using the phosphorothioate method*, Methods Mol. Biol. 57:369-374 (1996); Smith, *In vitro mutagenesis*, Ann. Rev. Genet. 19:423-462(1985); Botstein & Shortle, *Strategies and applications of in vitro mutagenesis*, Science 229:1193-1201(1985); Carter, *Site-directed mutagenesis*, Biochem. J. 237:1-7 (1986); Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, *Rapid and efficient site-specific mutagenesis without phenotypic selection*, Proc. Natl. Acad. Sci. USA 82:488-492 (1985); Kunkel et al., *Rapid and efficient site-specific mutagenesis without phenotypic selection*, Methods in Enzymol. 154, 367-382 (1987); Bass et al., *Mutant Trp repressors with new DNA-binding specificities*, Science 242:240-245 (1988); Methods in Enzymol. 100: 468-500 (1983); Methods in Enzymol. 154: 329-350 (1987); Zoller & Smith, *Oligonucleotide-directed mutagenesis using M*13*-derived vectors: an efficient and general procedure for the production of point mutations in any DNA fragment*, Nucleic Acids Res. 10:6487-6500 (1982); Zoller & Smith, *Oligonucleotide-directed mutagenesis of DNA fragments cloned into M*13 *vectors*, Methods in Enzymol. 100:468-500 (1983); Zoller & Smith, *Oligonucleotide-directed mutagenesis: a simple method using two oligonucleotide primers and a single-stranded DNA template*, Methods in Enzymol. 154:329-350 (1987); Taylor et al., *The use of phosphorothioate-modified DNA in restriction enzyme reactions to prepare nicked DNA*, Nucl. Acids Res. 13: 8749-8764 (1985); Taylor et al., *The rapid generation of oligonucleotide-directed mutations at high frequency using phosphorothioate-modified DNA*, Nucl. Acids Res. 13: 8765-8787 (1985); Nakamaye & Eckstein, *Inhibition of restriction endonuclease Nci I cleavage by phosphorothioate groups and its application to oligonucleotide-directed mutagenesis*, Nucl. Acids Res. 14: 9679-9698 (1986); Sayers et al., *Y-T Exonucleases in phosphorothioate-based oligonucleotide-directed mutagenesis*, Nucl. Acids Res. 16:791-802 (1988); Sayers et al., *Strand specific cleavage of phosphorothioate-containing DNA by reaction with restriction endonucleases in the presence of ethidium bromide*, (1988) Nucl. Acids Res. 16: 803-814; Kramer et al., *The gapped duplex DNA approach to oligonucleotide-directed mutation construction*, Nucl. Acids Res. 12: 9441-9456 (1984); Kramer & Fritz *Oligonucleotide-directed construction of mutations via gapped duplex DNA*, Methods in Enzymol. 154:350-367 (1987); Kramer et al., *Improved enzymatic in vitro reactions in the gapped duplex DNA approach to oligonucleotide-directed construction of mutations*, Nucl. Acids Res. 16: 7207 (1988); Fritz et al., *Oligonucleotide-directed construction of mutations: a gapped duplex DNA procedure without enzymatic reactions in vitro*, Nucl. Acids Res. 16: 6987-6999 (1988); Kramer et al., *Point Mismatch Repair*, Cell 38:879-887 (1984); Carter et al., *Improved oligonucleotide site-directed mutagenesis using M*13 *vectors*, Nucl. Acids Res. 13: 4431-4443 (1985); Carter, *Improved oligonucleotide-directed mutagenesis using M*13 *vectors*, Methods in Enzymol. 154: 382-403 (1987); Eghtedarzadch & Henikoff, *Use of oligonucleotides to generate large deletions*, Nucl. Acids Res. 14: 5115 (1986); Wells et al., *Importance of hydrogen-bond formation in stabilizing the transition state of subtilisin*, Phil. Trans. R. Soc. Lond. A 317: 415-423 (1986); Nambiar et al., *Total synthesis and cloning of a gene coding for the ribonuclease S protein*, Science 223: 1299-1301 (1984); Sakamar and Khorana, *Total synthesis and expression of a gene for the a-subunit of bovine rod outer segment guanine nucleotide-binding protein (transducin)*, Nucl. Acids Res. 14: 6361-6372 (1988); Wells et al., *Cassette mutagenesis: an efficient method for generation of multiple mutations at defined sites*, Gene 34:315-323 (1985); Grundström et al., *Oligonucleotide-directed mutagenesis by microscale 'shot-gun' gene synthesis*, Nucl. Acids Res. 13: 3305-3316 (1985); Mandecki, *Oligonucleotide-directed double-strand break repair in plasmids of Escherichia coli: a method for site-specific mutagenesis*, Proc. Natl. Acad. Sci. USA, 83:7177-7181 (1986); Arnold, *Protein engineering for unusual environments*, Current Opinion in Biotechnology 4:450-455 (1993); Sieber, et al., Nature Biotechnology, 19:456-460 (2001). W. P. C. Stemmer, Nature 370, 389-91 (1994); and, I. A. Lorimer, I. Pastan, Nucleic Acids Res. 23, 3067-8 (1995). Additional details on many of the above methods can be found in Methods in Enzymology Volume 154, which also describes useful controls for trouble-shooting problems with various mutagenesis methods.

A variety of techniques and methodologies for purification and detection of polypeptides and proteins of the invention are known in that art. These techniques and methodologies can be applied to detecting and purifying proteins comprising non-natural amino acids as noted herein. In general, antibodies are useful reagents for ELISA, western blotting, immunochemistry, affinity chromatography methods, surface plasmon resonance (SPR), Annexin V, FACS and many other methods. The references herein provide details on how to perform ELISA assays, western blots, SPR and the like. Other techniques and methodologies of the invention can include intact mass spectrometry (MS) and size exclusion chromatography (SEC). Intact mass spectrometry provides information on the accurate mass of the protein and the relative abundance of its isoforms. Size exclusion chromatography (SEC), also known in the art as molecular sieve chromatography, is a chromatographic method in which molecules in solution are separated by their size, and in some cases molecular weight.

Genome Editing Technology

In some embodiments, the present invention provides polynucleotides for inactivation, disruption, ablation or knockout of a target site or region in a cell using gene editing tools. As used herein, the terms "target", "target for", "targeted" or "targeted for" knockout, ablation, inactivation or disruption refers to a site or region in a cell or gene that is ablated, inactivated, disrupted, or knocked out. Several gene editing tools can be used to precisely modify a gene by inducing targeted DNA double-strand breaks (DSBs). Such gene editing tools, well known in the art, can include, but are not limited to, zinc-finger nucleases (ZFNs), transcription activator-like effector nucleases (TALENs), and meganucleases (MNs) also known in the art as homing endonuclease (HEs) (Gaj et al, 2013; Guha et al, 2017), and clustered regularly interspaced short palindromic repeats (CRISPR). In aspects of the present invention, gene editing tools were used to design constructs to recognize target sites or regions in a cell expressing a gene of interest or a production cell. and make double strand breaks in the target gene after transfection.

ZFNs are artificial fusion proteins of a zinc-finger DNA-binding domain and a non-specific DNA-cleavage domain from FokI restriction endonuclease. The zinc-finger domain can be engineered to be able to recognize specific DNA sequences so that gene editing can be achieved. TALENs are also artificial fusion proteins that consists of a DNA-binding domain from TALE proteins and a non-specific DNA-cleavage domain from FokI restriction endonuclease. TALEs (Transcription Activator-Like Effectors) are proteins from Xanthomonas bacteria and its DNA-binding domain can be engineered to bind to specific DNA sequences. Similar to ZFNs, TALENS can induce DSBs so that gene inactivation can be achieved. MNs, also known in the art as homing endonucleases are endonucleases that are highly site-specific in generating double strand DNAs. MNs have a large site-specific recognition site that can recognize 18-44 base pairs of DNA. Among the family members of MNs, LAGLIDADG is the most extensively investigated and engineered in applications of genome editing. Clustered regularly interspaced short palindromic repeats (CRISPR) technology is a recent genome editing technology that uses RNA-guided nuclease (Cas9 is the most widely used type II nuclease) to form targeted DNA double-stranded breaks (DSBs). During the self-repair process of targeted DSBs in the cell, nucleotide deletions and insertions often occurs and results in frame-shift of the corresponding genomic sequences of the coding region of targeted proteins and eventually their loss of function. Although CRISPR was initially discovered as an immune system of prokaryotic cells in defending viral invasion, its application in eukaryotic cells as a genome editing tool has been successfully developed (See for example, Cong, et al, 2013; Hsu, et al, 2014; Jinek, et al., 2012; Ran, et al., 2013). In comparison to the other genome editing technologies such as zinc-finger nucleases (ZFNs) and transcription activator-like effector nucleases (TALENs), and meganucleases (MNs) that use specific DNA binding domains to induce the formation of DSBs (for example, U.S. Pat. No. 8,597,912), CRISPR technology catalyzes the breaking of DNA with the help of guided RNAs (gRNAs) that use Watson-Crick base pairing to specific DNA sequences.

Although any of gene editing tool described herein can be use with the present invention, CRISPR technology is exemplified as it provides for a more efficient, highly specific technology that can be applied in variety of cells and organisms (Hsu, et al, 2014). As exemplified in the Examples herein, gRNA targeting sites or regions for knock-out, ablation, inactivation or disruption in a cell expressing a gene of interest can be designed using an online CRISPR gRNA design tool specific to CHO-K1 genome (see on the world wide web at staff.biosustain.dtu.dk/laeb/crispy/). Examples of sites or regions target gene that can be knocked out, ablated, inactivated or disrupted in a gene of interest are provided in Table 1 below.

TABLE 1 gRNA sequences used in CRISPR constructs

| SEQ. ID. NO. | Gene name | gRNA sequence | Genomic locus |
|---|---|---|---|
| 1 | BAX site-I | AGGCACTCGCTCAACTTCT | Exon 2 |
| 2 | BAX site-II | TGAGTGTGACCGGCTGTTG | Exon 1 |
| 3 | BAX site-III | TTTCATCCAGTATCGAGCT | Exon 2 |
| 4 | BAK-I | GAACAAATTGTCCATCTCG | Exon 2 |
| 5 | BAK-II | ATGCTGTAAGAACGGGAGT | Exon 3 |
| 6 | BAK-III | GAAGCCGGTCAAACCACGT | Exon 3 |
| 7 | UPF1-I | TCATGGATTGGCCAGTAAC | Exon 3 |
| 8 | UPF1-II | CCACTGGGCGAGACGGTGC | Exon 4 |
| 9 | UPF1-III | GAAGCACCGGTCCTGGATC | Exon 5 |
| 10 | Smg1-I | AGCTCTGTAGGTGGCGCAC | Exon 6 |
| 11 | Smg1-II | TGACATATGCCTCGGTAAT | Exon 10 |
| 12 | Smg1-III | TAATCGGTGGACCCCGAAT | Exon 10 |
| 13 | GS-I | AACAGGAGTATACTCTCTTG | Exon 1 |
| 14 | GS-II | CGCCAGACAAAGCCTATCGCA | Exon 1 |
| 15 | GS-III | AGCCTACGATCCCAAGGGGG | Exon 1 |
| 16 | isoGS-I | GCCTCCTCGATGTGCCTGG | Exon 1 |
| 17 | isoGS-II | CATTGTCCAGGTCCCCCTT | Exon 1 |
| 18 | isoGS-III | ACAATGCCCGTCGTCTGAC | Exon 2 |
| 19 | Zeocin-I | TGACCCTGTTCATCAGCGC | Exon 1 |
| 20 | Zeocin-II | TCAGCGCGGTCCAGGACCA | Exon 1 |
| 21 | Zeocin-III | TCCAGGACCAGGTGGTGCC | Exon 1 |
| 22 | Hygromycin-I | TCGATGAGCTGATGCTTTG | Exon 1 |
| 23 | Hygromycin-II | AGCTGATGCTTTGGGCCGA | Exon 1 |
| 24 | Hygromycin-III | GAGGACTGCCCCGAAGTCC | Exon 1 |
| 25 | Puromycin-I | GGCGGTGTTCGCCGAGATC | Exon 1 |
| 26 | Puromycin-II | CCGAGATCGGCCCGCGCAT | Exon 1 |
| 27 | Puromycin-III | GCGCATGGCCGAGTTGAGC | Exon 1 |
| 28 | IGFBP4-I | CAGGGCCTCGGCCGAGCCT | Exon 1 |
| 29 | IGFBP4-II | CCCGCTGCCGCCCCCCTGT | Exon 1 |
| 30 | IGFBP4-III | GGCTTGGGGATGCCCTGCG | Exon 1 |
| 31 | AQP1-I | TACATCATCGCCCAGTGTG | Exon 1 |
| 32 | AQP1-II | AGCTTCTTCTTGAATTCGC | Exon 1 |
| 33 | AQP1-III | ATGAAGACGAAGAGGGTCA | Exon 1 |
| 34 | Maf1-1 | AGATGCCCATATTATTGGC | Exon 1 |
| 35 | Maf1-2 | ATCTGGACTCAGACCCCTT | Exon 5 |
| 36 | Maf1-3 | GCAGGCAATGCATTGGACT | Exon 6 |
| 37 | eRF1-1 | CTCTTTTTGGCACGCTCCA | Exon 3 |

TABLE 1-continued gRNA sequences used in CRISPR constructs

| SEQ. ID. NO. | Gene name | gRNA sequence | Genomic locus |
|---|---|---|---|
| 38 | eRF1-2 | ATCCACAGTGAATTTGTGC | Exon 3 |
| 39 | eRF1-3 | CGTTTTGCCCGTTTAAGAA | Exon 4 |
| 40 | FUT8-I | GCAGATATGTTATTCTCCGC | Exon 4 |
| 41 | FUT8-II | GATCCGTCCACAACCTTGGC | Exon 4 |
| 42 | FUT8-III | GATAAACTGCAATCTGGTTG | Exon 9 |

In other aspects of the present invention, oligonucleotides were synthetized and used to amplify the genomic DNA locus of the gRNAs disclosed in the above Table as depicted in Table 2 below. These techniques are fully explained in the literature. See for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates.

TABLE 2

Oligo sequences used to amplify genomic DNA locus

| SEQ. ID. NO. | Gene name | Oligo sequence | Oligo ID |
|---|---|---|---|
| 43 | BAX | AGGGTTATGAGCCTCCCTAG | X-F |
| 44 | BAX | GGCTACCATGTAAAGAGACC | X-R |
| 45 | BAK | CAGACAGCCTTCTCTTGCT | K-I-II-F |
| 46 | BAK | AGAGCTCCTGAGAGGCATGA | K-I-II-R |
| 47 | BAK | TTTCACGCTGTGACACCCA | K-III-F |
| 48 | BAK | CAGAACCACACCAAGAATTG | K-III-R |
| 49 | UPF1 | TGTTTAGGACCTTCGGTTTC | U-I-F |
| 50 | UPF1 | ATGTCAAGGGCACTATAGAC | U-I-R |
| 51 | UPF1 | CCCAACGCAAGAGACCTTC | U-II-III-F |
| 52 | UPF1 | AGAGTGAACCTCAGCGCACG | U-II-III-R |
| 53 | Smg1 | AGTGAAAGAGAGAGGAGAGG | S-I-F |
| 54 | Smg1 | GATGAAGTGAAGTTGCTCTACC | S-I-R |
| 55 | Smg1 | CTACGCAAGGCACGAGGTTC | S-II-III-F |
| 56 | Smg1 | ATAAGCCTCTGCTACTCCAG | S-II-III-R |
| 57 | GS | CACTTGAACAAAGGCATCAAG | G-F |
| 58 | GS | TCTCATTGAGAAGGCATGTGC | G-R |
| 59 | isoGS | GGGAATTCCAAATAGGACCC | isoG-F |
| 60 | isoGS | CTGCTCGGGAAGGTTATGTT | isoG-R |
| 61 | Zeocin | ATGGCCAAGTTGACCAGTGCC | Z-F |
| 62 | Zeocin | TCAGTCCTGCTCCTCGGCCAC | Z-R |
| 63 | Hygromycin | ATGAAAAAGCCTGAACTCACC | H-F |

TABLE 2-continued

Oligo sequences used to amplify genomic DNA locus

| SEQ. ID. NO. | Gene name | Oligo sequence | Oligo ID |
|---|---|---|---|
| 64 | Hygromycin | TCATTCCTCTGCCCTCGGACG | H-R |
| 65 | Puromycin | ATGACCGAGTACAAGCCCACG | P-F |
| 66 | Puromycin | AGTCCGTGGCCCGAACGCCCA | P-R |
| 67 | IGFBP4 | GGCAGCGCGTCAGCCCCCTGC | I-F |
| 68 | IGFBP4 | TCAGTGCCAGTTTTCTTGGCT | I-R |
| 69 | AQP1 | GCTGAGGGGGCAGCAAGCTGC | A-F |
| 70 | AQP1 | CTGCCCAGCCCGAGGAGGCAG | A-R |
| 71 | Maf1 | ATGAAGCTACTCGAGAACTCC | M-I-F |
| 72 | Maf1 | TTTCATCCTCACCACCCTGGC | M-I-R |
| 73 | Maf1 | CAGGTGGGCTCACATCTTTGC | M-II-III-F |
| 74 | Maf1 | TCACATACAGATCACTGGAAC | M-II-III-R |
| 75 | eRF1 | TCATACTGTGTTGAGTGGGAC | RF-F |
| 76 | eRF1 | CCACACTAGAGAGCCCACAAC | RF-R |
| 77 | FUT8 | ATGCCATCATATATCGTGAGCATC | FUT-I-F |
| 78 | FUT8 | AAACAAGCTTGTTCCCTAACTAG | FUT-I-R |
| 79 | FUT8 | AGGAGTGTAGTGTAGTGATGAT | FUT-II-F |
| 80 | FUT8 | ATTTGCTCTGCTGCCCTAACT | FUT-II-R |
| 81 | FUT8 | TGACAGCAATGGACTGTTCTC | FUT-III-F |
| 82 | FUT8 | CAGCTTCAGGATATGTAGGGTA | FUT-III-R |

Gene Editing Targets

In embodiments of the invention disclosure genes targeted for knockout, disruption, ablation or inactivation in a cell expressing a gene of interest are provided. The term target for targeted knockout gene, target or targeted ablated gene, target or targeted inactivated gene, target or targeted disrupted gene as used herein refers to a gene that is targeted for knockout, ablation, or inactivation by gene editing. In some aspects of the invention the target or targeted site or region is involved in the apoptotic pathways. In other embodiments the invention provides, genes targeted for knockout, disruption, ablation or inactivation in a cell or cell line. The targeted knockout, disrupted, ablated or inactivated gene may include genes that modulate cell growth, differentiation, regulation, and the like. In other embodiments target genes for knockout, disruption, ablation or inactivation in a cell expressing a gene of interest including genes involved in the apoptotic pathways, for example pro-apoptotic genes, oncogenes and the like. Target genes for knockout, disruption, ablation or inactivation can include GS, Bcl-2 family, IGFBP4, AQP1, Maf1, eRF1, FUT8, P53, Caspase 3, UPF1, Smg1 and any extrinsically added selection marker genes (if applicable) such as Zeocin, Hygromycin, Puromycin, and the like, Smac/DIABLO, Apaf-1, Caspase-6, Caspase-7, Caspase-9, Caspase-10, PARP, Alpha fodrin, NuMA, AIF, CAD, Puma, Noxa, 14-3-3, Aven, Myc, HtrA2/Omi and the like, but are not limiting to such. The target gene for knockout, disruption, ablation or inactivation may include the bel-2 family such as Bcl-xl, Bak, Bax, Bcl-xs, Bid, Bim, Bad and Bik. In certain embodiments, the target for knockout, disruption, ablation or inactivation is BAX and/or BAK. In other embodiments, the targeted knockout, disrupted, ablated or inactivated gene is fully or partially knocked out, ablated or inactivated. A partially inactivated, disrupted, knocked out or ablated gene may include a gene that is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, inactivated, disrupted, knocked-out or ablated.

Biotherapeutic Genes

The invention disclosure provides a gene of interest expressed in a platform cell line. Such genes of interest can be a biotherapeutic including, but not limited to, cytokines, growth factors, hormones, interferons, interleukins, other regulatory peptides and proteins and antibodies. Biotherapeutics of the invention can include any biological products from genetically engineered bacteria, yeast, fungi, or cells. Biotherapeutics of the invention include DNA, RNA, recombinant DNA, proteins, polypeptides. In some embodiments the biotherapeutic is a vaccine, the vaccine obtained by any method or cell of the invention.

In other embodiments, the present invention provides platform cells or cell lines expressing a gene of interest including, but is not limited to, for example, Alpha-1 antitrypsin, Angiostatin, Antihemolytic factor, antibodies, Apolipoprotein, Apoprotein, Atrial natriuretic factor, Atrial natriuretic polypeptide, Atrial peptides, Calcitonin, CD40 ligand, C-kit Ligand, Collagen, Colony stimulating factor (CSF), Complement factor 5a, Complement inhibitor, Complement receptor 1, cytokines, (for example, epithelial Neutrophil Activating Peptide-78, GROα/MGSA, GROβ, GROγ, MIP-1α, MIP-1δ, MCP-1), Epidermal Growth Factor (EGF), Erythropoietin ("EPO",), Exfoliating toxins A and B, Factor IX, Factor VII, Factor VIII, Factor X, Fibroblast Growth Factor (FGF), Fibrinogen, Fibroncctin, G-CSF, GM-CSF, CD116, M-CSF, CSF-1R, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., *Staphylococcal enterotoxins* (SEA, SEB, SEC1, SEC2, SEC3, SED, SEE), Superoxide dismutase (SOD), Toxic shock syndrome toxin (TSST-1), Thymosin alpha 1, Tissue plasminogen activator, TGF beta and MIF, Vascular Endothelial Growth Factor (VEGF), Urokinase, and the like.

In other embodiments gene of interest can include interleukins such as but not limited to, IL-1 and CD121a, IL-2 and CD25/CD122/CD137, IL-3 and CD123, IL-4 and CD124, IL-5 and CD125, IL-6 and CD126, IL-7 and CD127/CD132, IL-9 and IL-9R, IL-10 and CRF2-4, IL-11 and IL-11R, IL-12 and IL-12Rβ1c/IL-12Rβ2, IL-13 and IL-13R, IL-15 and CD122/CD132, IL-16 and CD4, IL-17 and CD217, IL-18 and IL-1Rrp, IL-19 and IL-20Rα/IL-10Rβc, IL-21 and IL-21R/CD132, IL-22 and IL-22Rαc/IL-10Rβc, IL-23 and IL-23R, IL-24 and IL-22Rαc/IL-10Rβc, IL-25 and IL-17BR, IL-26 and IL-20Rα/IL-10Rβc, IL-27 and WSX-1/CD130c, IL-28 and IL-28Rαc/IL-10Rβc, IL-29 and IL-28Rαc/IL-10Rβc, IL-30 and WSX-1/CD130c, IL-31 and IL31A/OSMR, IL-32, IL-33 and ST2/IL1RAP, IL-34 and CSF-1R, IL-35 and IL-12RB2, IL-36 and IL-1Rrp2, IL-37 and IL-18Rα, TSLP and TSLPR, LIF and LIFR, OSM and OSMR and the like.

In some aspects of the invention a gene of interest may include tumor necrosis factor TNF) including, but not limited to, tumor necrosis factor beta (TNF beta), Tumor necrosis factor receptor (TNFR), Tumor necrosis factor-alpha (TNF alpha) and p55/p75, LT-α and p55/p75, LT-β and p55/p75, CD40 L and CD40, FasL and CD95, CD27 L and CD27, CD30 L and CD30, 4-1BBL and 4-1BB, Trail and DR4, RANK-L and RNAK, APRIL and TAC1, LIGHT and HVEM, TWEAK and TWEAKR, BAFF and TAC1, and the like.

The gene of interest may include C—X—C chemokines (for example, T39765, NAP-2, ENA-78, Gro-a, Gro-b, Gro-c, IP-10, GCP-2, NAP-4, SDF-1, PF4, MIG), including CXCL1 and CXCR2, CXCL2 and CXCR2, CXCL3 and CXCR2, CXCL4 and CXCR3B, CXCL5 and CXCR2, CXCL6 and CXCR2, CXCL7 and CXCR1/CXCR2, CXCL8 and CXCR1/CXCR2, CXCL9 and CXR3A/3B, CXCL10 and CXCRA/3B, CXCL11 and CXCR3A/3B/CRCR7, CXCL12 and CXCR4/CXCR7, CXCL13 and CXCR5, CXCL14, CXCL15, CXCL16 and CXCR6 and the like. The gene of interest may also include CC chemokines (for example, Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), including CCL1 and CCR6, CCL2 and CCR2, CCL3 and CCR1/5, CCL4 and CCR5, CCL5 and CCR1/CCR3, CCR5, CCL6 and CCR1, CCL7 and CCR1/CCR2/CCR3/CCR5, CCL8 and CCR1/CCR2/CCR5, CCL9 and CCR1, CCL11 and CCR3, CCL12 and CCR2, CCL13 and CCR2/3, CCL14 and CCR1/3/5, CCL15 and CCR1/3, CCL16 and CCR1/2/5/8, CCL17 and CCR4, CCL18 and PITPNM3, CCL19 and CCR7, CCL20 and CCR6, CCL21 and CCR7, CCL22 and CCR4, CCL23 and CCR1/FPRL-1, CCL24 and CCR3, CCL25 and CCR9, CCL26 and CCR3, CCL27 and CCR10, CCL28 and CCR10, and including XCL1 and XCR1, XCL2 and XCR1, CX3CL1 and CX3CR1 and the like.

The methods, compositions, strategies and techniques described herein are not limited to a particular type, class or family of polypeptides or proteins. Indeed, virtually any polypeptides may be designed or modified to include at least one "modified or unmodified" non-natural amino acids described herein. By way of example only, the polypeptide can be homologous to a biotherapeutic or therapeutic protein described herein. Proteins or polypeptides of interest with at least one non-natural amino acid are a feature of the invention. The invention also includes polypeptides or proteins with at least one non-natural amino acid produced using the compositions and methods of the invention. An excipient (e.g., a pharmaceutically acceptable excipient) can also be present with the protein.

By producing proteins or polypeptides of interest with at least one non-natural amino acid incorporated in vertebrate cells, proteins or polypeptides will typically include vertebrate posttranslational modifications. In certain embodiments, a protein includes at least one non-natural amino acid and at least one post-translational modification that is made in vivo by a vertebrate cell, where the post-translational modification is not made by a prokaryotic cell. For example, the post-translation modification includes, e.g., acetylation, acylation, lipid-modification, palmitoylation, palmitate addition, phosphorylation, glycolipid-linkage modification, glycosylation, and the like.

The invention disclosure includes a selector codon-containing gene or gene of interest. The gene of interest may include a therapeutic protein or polypeptide, genes involve in cell growth, differentiation, regulation, inflammation, oncogenes and the like, but not limited to such. In other embodiments, the invention disclosure includes a selector codon-containing antibody gene. In other embodiments, the antibody can be any antibody of interest, including but not limited to an anti-Her2, anti CD-70, anti-PSMA, 5T4, EGFR, TROP2, CD3, Interleukins (including 2, 3, 10 but not limited to such), GPC3, DLL3, ROR1, leptin, the FGF family including FGF-21 and FGF-23, HGH, FcR, insulin, TNFR1, TRAIL, erythropoietin, and analogs, bispecifics and fragments thereof and the like, but not limited to such. In some embodiments, the invention includes selector codon-containing antibody gene. Antibodies of the invention can be, for example, polyclonal, monoclonal, chimeric, humanized, single chain, Fab fragments, fragments produced by a Fab expression library, or the like. Antibodies of the invention may include, but is not limited to, for example, tumor-specific MAbs that arrest tumor growth by targeting tumor cells for destruction by antibody-dependent cell-mediated cytotoxicity (ADCC) or complement-mediated lysis (CML) (these general types of Abs are sometimes referred to as "magic bullets"). One example is Rituxan, an anti-CD20 MAb for the treatment of Non-Hodgkins lymphoma (Scott (1998) *Rituximab: a new therapeutic monoclonal antibody for non-Hodgkin's lymphoma* Cancer Pract 6: 195-7); Antibodies which interfere with a critical component of tumor growth. Herceptin is an anti-HER-2 monoclonal antibody for treatment of metastatic breast cancer, and provides an example of an antibody with this mechanism of action (Baselga et al. (1998) *Recombinant humanized anti-HER2 antibody (Herceptin) enhances the antitumor activity of paclitaxel and doxorubicin against HER2/neu overexpressing human breast cancer xenografts* [published erratum appears in *Cancer Res* (1999) 59(8): 2020], *Cancer Res* 58: 2825-31). Another example relates to antibodies for delivery of cytotoxic compounds (toxins, radionuclides, etc.) directly to a tumor or other site of interest. For example, one application Mab is CYT-356, a 90Y-linked antibody that targets radiation directly to prostate tumor cells (Deb et al. (1996) *Treatment of hormone-refractory prostate cancer with 90Y-CYT-356 monoclonal antibody Clin Cancer Res* 2: 1289-97. Other examples may include antibody-directed enzyme prodrug therapy, where an enzyme co-localized to a tumor activates a systemically-administered pro-drug in the tumor vicinity. For example, an anti-Ep-CAMI antibody linked to carboxypeptidase A is being developed for treatment of colorectal cancer (Wolfe et al. (1999) *Antibody-directed enzyme prodrug therapy with the T268G mutant of human carboxypeptidase A1: in vitro and in vivo studies with prodrugs of methotrexate and the thymidylate synthase inhibitors GW1031 and GW1843 Bioconjug Chem* 10: 38-48). Other antibodies (e.g., antagonists) designed to specifically inhibit normal cellular functions for therapeutic benefit may be included. An example is Orthoclone OKT3, an anti-CD3 MAb offered by Johnson and Johnson for reducing acute organ transplant rejection (Strate et al. (1990) *Orthoclone OKT3 as first-line therapy in acute renal allograft rejection Transplant Proc* 22: 219-20. Another class of antibodies may include those that are agonists. These Mabs are designed to specifically enhance normal cellular functions for therapeutic benefit. For example, Mab-based agonists of acetylcholine receptors for neurotherapy are under development (Xie et al. (1997) *Direct demonstration of MuSK involvement in acetylcholine receptor clustering through identification of agonist ScFv Nat. Biotechnol.* 15: 768-71. Any of these antibodies can be modified to include one or more unnatural amino acid to enhance one or more therapeutic property (specificity, avidity, serum-half-life, etc.). Another example may include catalytic antibodies such as Ig sequences that have been engineered to mimic the catalytic abilities of enzymes (Wentworth and Janda (1998) *Catalytic antibodies Curr Opin Chem Biol* 2: 138-44. Catalytic antibodies can also be modified to include one or more unnatural amino acid to improve one or more property of interest.

Selector codons of the invention expand the genetic codon framework of the protein biosynthetic machinery. For example, a selector codon includes, e.g., a unique three base codon, a nonsense codon, such as a stop codon, e.g., an amber codon (UAG), an opal codon (UGA), an unnatural codon, at least a four-base codon, a rare codon, or the like. A number of selector codons can be introduced into a desired gene, e.g., one or more, two or more, more than three, etc. A gene can include multiple copies of a given selector codon, or can include multiple different selector codons, or any combination thereof. In one embodiment, the methods and compositions of the invention involve the use of a selector codon-containing gene or gene of interest, disclosed herein. In one embodiment, the methods and compositions of the invention involve the use of a selector codon-containing antibody wherein the selector codon can be on the heavy chain, the light chain or both. Thus, a selector codon of the invention includes a stop codon for the incorporation of unnatural amino acids in vivo in a eukaryote cell.

Production Cells

In some embodiments, the invention disclosure provides production cells, cell lines and clones generated therefrom expressing a gene of interest. Such production cells or cell lines include, but are not limited to, transiently transfected cell populations, stable bulk cell populations (for example, mixed or pool of cells), stable mini cell populations (for example, mini pools or master well populations), and stable clonal cell lines (for example as derived from a single cell). Transiently transfected cell populations used herein refers to a pool of cells in which a gene of interest is introduced into and may not be stably integrated into the genome. Stable cell or stable production cell line used herein refers to a cell in which a gene of interest is introduced into and stably integrated into the genome. A stable mini cell population may have less heterogenicity than a stable bulk cell population.

In some embodiment, the invention relates to a stable production cell line comprising an orthogonal aminoacyl tRNA synthetase (O-RS), an orthogonal suppressor tRNA (O-tRNA), and a selector codon-containing gene of interest with a non-natural amino acid incorporated, and a target knockout, ablated, inactivated or disrupted gene. In other embodiments, the invention disclosure relates to production cells, cell lines and clones generated therefrom expressing a gene of interest and a target knockout, ablated, inactivated or disrupted gene. In other embodiments, the target knockout, ablated, inactivated or disrupted gene is a gene involve in promoting cell growth and productivity. In other embodiments the target knockout, ablated, inactivated or disrupted gene is a gene involved in the apoptosis pathway, for example pro-apoptotic gene. In an exemplary embodiment, the invention disclosure provides methods and compositions for generation of a cell or cell line expressing a gene of interest with a non-natural incorporated amino acid and one or more target knockout, disruption, ablation or inactivation gene (for example, BAX and/or BAK). Other target knockout genes may include the Bcl-2 family of proteins well known in the art for their ability to control apoptotic cell death via the mitochondrial pathway. Bcl-2 and some of its homologues, such as Bcl-xl, are known to inhibit apoptosis. Other known pro-apoptotic Bcl-2 family members and include Bak, Bax, Bcl-xs, Bid, Bim, Bad and Bik. With an appropriate stimulus, Bax and/or Bak can induce or accelerate apoptosis. The Bcl-2 family of proteins share significant sequence and structural homology. This family of proteins is characterized by up to four regions of sequence homology, known as the Bcl-2 homology domains. For example, Bax protein shares highly conserved domains with Bcl-2. Some of these domains are involved in Bax/Bcl-2 heterodimer formation which are thought to be important for cell survival or cell death in response to apoptotic signals. Upon activation, Bax translocates to the outer mitochondrial membrane where it oligomerizes, renders the membrane permeable, and releases several death-promoting factors, including cytochrome C (Scorrano et al. (2003) Biochem. Biophys. Res. Commun. 304:437-444). Bax can be rendered inactive in normal cells via interaction with the Ku70 protein, which sequesters Bax from mitochondria (Sawada et al. (2003) Nat. Cell Biol. 5:320-329). Like Bax, the Bak gene product enhances apoptotic cell death in the presence of an appropriate stimulus. Bak also promotes cell death and counteracts Bcl-2 apoptotic protection. Bak is a known potent apoptosis inducer in various cell types. Thus, the invention disclosure, in an exemplary manner, provides methods and compositions generation of producer cell lines with partial or complete inactivation of one or more of a BAK gene and/or a BAX gene in a cell or cell line expressing a gene of interest and a non-natural amino acid-incorporated. Inactivation of an apoptotic agent, (for example, BAX and/or BAK), in a cell expressing a gene of interest can be used to generate cell lines that are resistant to apoptosis and improve the production of recombinant proteins including but not limited to, for example, antibodies, recombinant viral vectors and in the manufacture of vaccines.

Cell lines of the present disclosure can be utilized for recombinant protein production. Recombinant protein includes, but is not limited to, antibodies, antigens, therapeutic proteins as disclosed elsewhere herein. In some embodiments the invention involves eukaryote or vertebrate cells or cell lines, including but not limited mammals, insects, reptiles, birds, and the like or ciliates, plants (including but not limited to, monocots, dicots, and algae), fungi, yeasts, flagellates, microsporidia, and protists. Eukaryotic cells can be used for in vivo incorporation of an unnatural amino acid. Cells can be used for genetically engineered (e.g., transformed, transduced or transfected) with the polynucleotides of the invention or constructs which include a polynucleotide of the invention, e.g., a vector of the invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., Proc. Natl. Acad. Sci. USA 82, 5824 (1985), infection by viral vectors, high velocity ballistic penetration by small particles with the nucleic acid either within the matrix of small beads or particles, or on the surface (Klein et al., Nature 327, 70-73 (1987)).

Several well-known methods of introducing nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular nucleic acid of interest. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and vertebrate systems. Vectors are suitable for replication and integration in prokaryotes, eukaryotes, or preferably both. See, Giliman & Smith, Gene 8:81 (1979); Roberts, et al., Nature, 328:731 (1987); Schneider, B., et al., Protein Expr. Purif. 6435: 10 (1995); Ausubel, Sambrook, Berger (all supra). A catalogue of Bacteria and Bacteriophages useful for cloning is provided, e.g., by the ATCC, e.g., The ATCC Catalogue of Bacteria and Bacteriophage (1992) Gherna et al. (eds) published by the ATCC. Additional basic procedures for sequencing, cloning and other aspects of molecular biology and underlying theoretical considerations are also found in Watson et al. (1992) Recombinant DNA Second Edition Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, TX mcrc.com), The Great American Gene Company (Ramona, CA available on the World Wide Web at genco.com), ExpressGen Inc. (Chicago, IL available on the World Wide Web at expressgen.com), Operon Technologies Inc. (Alameda, CA) and many others.

The cells or cell lines of the invention disclosure can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, NY;

Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, FL.

Conventional medium or media, as used herein, refer to any culture medium used to grow and harvest cells and/or products expressed and/or secreted by such cells. Such "medium" or "media" include, but are not limited to, solution, solid, semi-solid, or rigid supports that may support or contain any host cell, including, by way of example, bacterial host cells, yeast host cells, insect host cells, plant host cells, eukaryotic host cells, mammalian host cells, CHO cells, prokaryotic host cells, *E. coli*, or *Pseudomonas* host cells, and cell contents. Such "medium" or "media" includes, but is not limited to, medium or media in which the host cell has been grown into which a polypeptide has been secreted, including medium either before or after a proliferation step. Such "medium" or "media" also includes, but is not limited to, buffers or reagents that contain host cell lysates, by way of example a polypeptide produced intracellularly and the host cells are lysed or disrupted to release the polypeptide. In other embodiments of the present invention, the media may be a complete cell culture medium, a traditional cell culture medium, or a chemically defined medium. A complete cell culture medium often has two major categories of components: basal medium and growth supplements. The basal medium is the nutrient mixture consisting of the small molecular weight components including sugar, amino acids, vitamins, various salts, etc. The basal medium does not merely provide a nutritional source for deriving energy and making new cell mass and product, it also provides balanced salt concentrations and osmolarity to allow for cell growth. However, most cells will not grow if provided with basal medium alone, as basal medium does not contain growth factors or other factors necessary for "optimal" growth conditions. Growth supplements that may be added to basal medium include growth factors, phospholipids, soy hydrolysate, scrum, etc. These supplements may promote cell growth by providing constituent components for specific signaling pathways or may supply special nutritional needs (such as delivering cholesterol) and may direct cellular differentiation. Traditional cell culture medium contains up to 15% animal serum in addition to basal medium. Serum is a highly complex fluid in terms of its chemical composition. Such a medium, containing a largely undefined chemical composition, is called a complex medium. Many supplements commonly used in industrial processes, e.g., plant hydrolysates, soy phospholipids, also fall into this category. Their use renders the chemical composition of the medium undefined. A chemically defined medium contains only components whose chemical composition is known and characterized and has all of its chemical species specified. It does not contain any mixture of components with unknown or undefined composition. For example, "lipids" or "phospholipids" are not well-defined compounds but are mixtures of a class of compounds and are not chemically specified. A chemically defined medium often contains growth factors, cytokines, and carrier proteins. Thus, a chemically defined medium is not necessarily protein-free.

In embodiments of the present invention batch and fed-batch production are utilized. Standard methods for batch and fed batch production are well understood in the art. In a batch process, the constraint of osmolarity limits the amount of nutrients that can be added initially. This low-nutrient level prevents the culture from attaining high cell and product concentrations. In fed batch cultures, medium is added during cultivation to prevent nutrient depletion, thus prolonging the growth phase and ultimately increasing cell and product concentrations. A variety of fed batch operations, ranging from very simple to highly complex and automated, are utilized in current production facilities. The media used in both batch and fed batch can be commercially available or proprietary media developed in-house. The type of media can be a complex medium containing a largely undefined chemical composition, or a chemically defined medium comprising components having a chemical composition(s) that is known and characterized and has all of its chemical species specified. In some embodiments, the chemically defined medium comprises only components whose chemical composition is known and characterized and has all of its chemical species specified. In other embodiments, the type of media utilized can be an admixture containing undefined chemical composition and chemically defined composition. In another embodiment, the undefined chemical composition and chemically defined composition be in any of a combination of 99%-90% and 1%-10% respectively, or 89%-80% and 11%-20% respectively, or 79%-70% and 21%-30% respectively, or 69%-60% and 31%-40% respectively, or 59%-50% and 41%-50% respectively; or in any of a combination of 1%-10% and 99%-90% respectively, or 11%-20% and 89%-80% respectively, or 21%-30% and 79%-70% respectively, or 31%-40% and 69%-60% respectively, or 41%-50% and 59%-50% respectively. Most such methods or alternative methods are well known to the skilled artisan. See for example, Weishou Hu, et al., *Cell Culture Process Engineering* (2013).

The methods and compositions of the present invention provide for high producer eukaryote cell or cell lines for the generation of proteins or polypeptides containing or comprising non-natural amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the polypeptide of protein that comprises an non-natural amino acid, or an amount that can be achieved with in vivo protein production methods. In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nl to about 100 L). The production of large quantities (e.g., greater that that typically possible with other methods, e.g., in vitro translation) of a protein in a eukaryote or vertebrate cell including at least one non-natural amino acid is a feature of the invention.

In some embodiments, a cell of the present invention is an engineered or recombinant host cell or a platform cell, also referred to as "host cell." Such platform, engineered or recombinant host cell, or host cell, refers to a cell which includes an exogenous polynucleotide, wherein the methods used to insert the exogenous polynucleotide into a cell include, but are not limited to, direct uptake, transduction, f-mating, or other methods known in the art to create recombinant host cells. By way of example only, such exogenous polynucleotide may be a nonintegrated vector, including but not limited to a plasmid, or may be integrated into the host genome. In other aspects of the invention, the gene of interest can be transfected into a platform, engineered or recombinant host cell to generate a production cell line for generating or manufacturing a biotherapeutic, including but not limited to an antibody. In another embodiment of the invention a production cell line is a cell line having a gene of interest. In other embodiments of the invention a production cell line that has a gene of interest silenced or knocked out, ablated, inactivated or disrupted can become a platform cell line. In some aspects of the invention, a platform cell can be a cell line comprising an orthogonal tRNA/RS system without having a gene of interest.

In some embodiments, the compositions of the invention may be substantially purified. The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% of contaminating components. Thus, a "substantially purified" component of interest may have a purity level of about 70%, about 75%, about 80%, about 85%, about 90%, about 95%, about 96%, about 97%, about 98%, about 99% or greater. By way of example only, a natural amino acid polypeptide or a non-natural amino acid polypeptide may be purified from a native cell, or host cell in the case of recombinantly produced natural amino acid polypeptides or non-natural amino acid polypeptides. By way of example a preparation of a natural amino acid polypeptide or a non-natural amino acid polypeptide may be "substantially purified" when the preparation contains less than about 30%, less than about 25%, less than about 20%, less than about 15%, less than about 10%, less than about 5%, less than about 4%, less than about 3%, less than about 2%, or less than about 1% of contaminating material. By way of example when a natural amino acid polypeptide or a non-natural amino acid polypeptide is recombinantly produced by host cells, the natural amino acid polypeptide or non-natural amino acid polypeptide may be present at about 30%, about 25%, about 20%, about 15%, about 10%, about 5%, about 4%, about 3%, about 2%, or about 1% or less of the dry weight of the cells. By way of example when a natural amino acid polypeptide or a non-natural amino acid polypeptide is recombinantly produced by host cells, the natural amino acid polypeptide or non-natural amino acid polypeptide may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. By way of example, "substantially purified" natural amino acid polypeptides or non-natural amino acid polypeptides may have a purity level of about 30%, about 35%, about 40%, about 45%, about 50%, about 55%, about 60%, about 65%, about 70%, about 75%, about 80%, about 85%, about 90%, about 95%, about 99% or greater as determined by appropriate methods, including, but not limited to, SDS/PAGE analysis, RP-HPLC, SEC, and capillary electrophoresis. The polypeptide or protein of the invention may include an excipient (e.g., buffer, water, pharmaceutically acceptable excipient, but not limiting to such).

In certain embodiments, the invention provides a vector (for example, a plasmid, a cosmid, a phage, a virus, but not limiting to such) comprising an engineered nucleic acid of the invention, an orthogonal suppressor tRNA (O-tRNA), an orthogonal aminoacyl tRNA synthetase (O-RS), a selector codon-containing antibody gene. In one embodiment, the vector is an expression vector. In another embodiment, the expression vector includes a promoter operably linked to one or more of the polynucleotides of the invention. In another embodiment, a cell comprises a vector that includes a polynucleotide of the invention. The vector may further comprise a reporter. As used herein, the term "reporter" refers to a component that can be used to select target components of a system of interest. For example, a reporter can include a fluorescent screening marker (e.g., green fluorescent protein), a luminescent marker (e.g., a firefly luciferase protein), an affinity based screening marker, or selectable marker genes such as his3, ura3, leu2, lys2, lacZ, β-gal/lacZ (β-galactosidase), Adh (alcohol dehydrogenase), or the like.

The methods and compositions of the invention may include agents, substances and markers for screening or selecting a gene, polypeptide or protein. A selection or screening agent as used herein, refers to an agent that, when present, allows for a selection/screening of certain components from a population. For example, a selection or screening agent includes, but is not limited to, e.g., a nutrient, an antibiotic, a wavelength of light, an antibody, an expressed polynucleotide (e.g., a transcriptional modulator protein), or the like. The selection agent can be varied, e.g., by concentration, intensity, etc. In other embodiments, the methods and compositions of the invention include a detectable substance. Detectable substances may also be used. The term "detectable substance," as used herein, refers to an agent that, when activated, altered, expressed or the like, allows for the selection/screening of certain components from a population. For example, the detectable substance can be a chemical agent, e.g., 5-fluroorotic acid (5-FOA), which under certain conditions, e.g., expression of a URA3 reporter, becomes detectable, e.g., a toxic product that kills cells that express the URA3 reporter. In addition, methods, compositions, cells or cell lines of the invention include a positive and/or a negative selection or screening marker. As used herein, the term "positive selection or screening marker" refers to a marker that when present, e.g., expressed, activated or the like, results in identification of a cell with the positive selection marker from those without the positive selection marker. As used herein, the term "negative selection or screening marker" refers to a marker that when present, e.g., expressed, activated or the like, allows identification of a cell that does not possess the desired property (e.g., as compared to a cell that does possess the desired property).

Orthogonal tRNA and Orthogonal Aminoacyl-tRNA Synthetase

In some embodiment, the invention relates to a stable production cell line comprising an orthogonal aminoacyl tRNA synthetase (O-RS), an orthogonal suppressor tRNA (O-tRNA), and a selector codon-containing gene of interest (for example biotherapeutics including antibodies). The ability to genetically modify the structures of proteins directly in eukaryote cells, beyond the chemical constraints imposed by the genetic code, provides a powerful molecular tool to both probe and manipulate cellular processes. The invention provides translational components that expand the number of genetically encoded amino acids in vertebrate cells. These include tRNA's (e.g., orthogonal tRNA's (O-tRNA's)), aminoacyl-tRNA synthetases (e.g., orthogonal synthetase (O-RS)), pairs of O-tRNA/O-RSs, and unnatural amino acids.

An orthogonal pair is composed of an O-tRNA, e.g., a suppressor tRNA, a frameshift tRNA, or the like, and an O-RS. The O-tRNA is not acylated by endogenous synthetases and is capable of mediating incorporation of an unnatural amino acid into a protein that is encoded by a polynucleotide that comprises a selector codon that is recognized by the O-tRNA in vivo. The O-RS recognizes the O-tRNA and preferentially aminoacylates the O-tRNA with an unnatural amino acid in a vertebrate cell. Methods for producing orthogonal pairs along with orthogonal pairs produced by such methods and compositions of orthogonal pairs for use in vertebrate cells are disclosed in International patent applications WO 2002/086075, entitled "Methods and compositions for the production of orthogonal tRNA-aminoacyltRNA synthetase pairs." See also, Forster et al., (2003) *Programming peptidomimetic synthetases by translating genetic codes designed de novo* PNAS 100(11):6353-6357; and, Feng et al., (2003), *Expanding* 1*RNA recognition of a tRNA synthetase by a single amino acid change*, PNAS 100(10): 5676-5681; each incorporated herein by reference. The development of multiple orthogonal tRNA/synthetase pairs can allow the simultaneous incorporation of multiple unnatural amino acids using different codons in a vertebrate cell.

Orthogonal tRNA and Orthogonal aminoacyl-tRNA are known in the art. See for example, WO 2008/030612, WO 2008/030614, WO 2008/030613, WO 2006/068802, WO 2007/021297, WO 2007/070659, U.S. Pat. Nos. 8,420,792, 9,133,495; 7,736,872; 7,846,689; 7,883,866; 7,838,265; 7,829,310; 7,858,344; 7,632,823; and 9,586,988, each incorporated herein by reference. Additional details for producing O-RS can be found in WO 2002/086075 entitled "Methods and compositions for the production of orthogonal tRNA-aminoacyltRNA synthetase pairs." See also, Hamano-Takaku et al., (2000)*A mutant Escherichia coli Tyrosyl-tRNA Synthetase Utilizes the Unnatural Amino Acid Azatyrosine More Efficiently than Tyrosine*, Journal of Biological Chemistry, 275(51):40324-40328; Kiga et al. (2002), *An engineered Escherichia coli tyrosyl-*1*RNA synthetase for site-specific incorporation of an unnatural amino acid into proteins in vertebrate translation and its application in a wheat germ cell-free system*, PNAS 99(15): 9715-9723; and, Francklyn et al., (2002), *Aminoacyl-tRNA synthetases: Versatile players in the changing theater of translation*; RNA, 8:1363-1372.

An orthogonal O-tRNA/O-RS pair in a vertebrate cell can be produced by importing a pair, e.g., a nonsense suppressor pair, from a different organism with inefficient cross species aminoacylation. The O-tRNA and O-RS are efficiently expressed and processed in the vertebrate cell and the O-tRNA is efficiently exported from the nucleus to the cytoplasm. For example, one such pair is the tyrosyl-tRNA synthetase/$tRNA_{CUA}$ pair from *E. coli* (see, e.g., H. M. Goodman, et al., (1968), Nature 217:1019-24; and, D. G. Barker, et al., (1982), FEBS Letters 150:419-23). *E. coli* tyrosyl-tRNA synthetase efficiently aminoacylates its cognate *E. coli* $tRNA_{CUA}$ when both are expressed in the cytoplasm of *S. cerevisiae*, but does not aminoacylate *S. cerevisiae* tRNA's. See, e.g., H. Edwards, & P. Schimmel, (1990), Molecular & Cellular Biology 10:1633-41; and, H. Edwards, et al., (1991), PNAS United States of America 88:1153-6. In addition, *E. coli* tyrosyl $tRNA_{CUA}$ is a poor substrate for *S. cerevisiae* aminoacyl-tRNA synthetases (see, e.g., V. Trezeguet, et al., (1991), Molecular & Cellular Biology 11:2744-51), but functions efficiently in protein translation in *S. cerevisiae*. See, e.g., H. Edwards, & P. Schimmel, (1990) Molecular & Cellular Biology 10:1633-41; H. Edwards, et al., (1991), PNAS United States of America 88:1153-6; and, V. Trezeguet, et al., (1991), Molecular & Cellular Biology 11:2744-51. Moreover, *E. coli* TyrRS does not have an editing mechanism to proofread an unnatural amino acid ligated to the tRNA.

Non-Natural Amino Acids

The incorporation of a non-natural or unnatural amino acid can be done to, tailor changes in protein structure and/or function including to change size, acidity, nucleophilicity, hydrogen bonding, hydrophobicity, accessibility of protease target sites, target to a moiety (e.g., for a protein array), and the like. Proteins that include a non-natural amino acid can have enhanced or even entirely new catalytic or physical properties. For example, the following properties are optionally modified by inclusion of anon-natural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one non-natural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function*, Current Opinion in Chemical Biology, 4:645-652.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

Non-natural amino acids that may be used in the methods and compositions described herein include, but are not limited to, amino acids comprising amino acids with novel functional groups, amino acids that covalently or noncovalently interact with other molecules, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Specific examples of unnatural amino acids include, but are not limited to, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like.

The chemical moieties incorporated into polypeptides via incorporation of non-natural amino acids into such polypeptides offer a variety of advantages and manipulations of polypeptides. For example, the unique reactivity of a carbonyl or dicarbonyl functional group (including a keto- or aldehyde-functional group) allows selective modification of proteins with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The polypeptide with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Non-natural amino acid uptake by a eukaryotic cell is one issue that is typically considered when designing and selecting non-natural amino acids, including but not limited to, for incorporation into a polypeptide or protein. For example, the high charge density of α-amino acids suggests that these compounds are unlikely to be cell permeable. Natural amino acids are taken up into the eukaryotic cell via a collection of protein-based transport systems. A rapid screen can be done which assesses which non-natural amino acids, if any, are taken up by cells. See, e.g., the toxicity assays in, e.g., the U.S. Patent Publication No. 2004/198637 entitled "Protein Arrays," which is herein incorporated by reference in its entirety, and Liu, D. R. & Schultz, P. G. (1999) *Progress toward the evolution of an organism with an expanded genetic code*. Proc. Natl. Acad. Sci. USA., 96:4780-4785. Although uptake is easily analyzed with various assays, an alternative to designing non-natural amino acids that are amenable to cellular uptake pathways is to provide biosynthetic pathways to create amino acids in vivo.

Typically, the non-natural amino acid produced via cellular uptake as described herein is produced in a concentration sufficient for efficient protein biosynthesis, including but not limited to, a natural cellular amount, but not to such a degree as to affect the concentration of the other amino acids or exhaust cellular resources. Typical concentrations produced in this manner are about 10 mM to about 0.05 mM.

Many biosynthetic pathways already exist in cells for the production of amino acids and other compounds. While a biosynthetic method for a particular non-natural amino acid may not exist in nature, including but not limited to, in a cell, the methods and compositions described herein provide such methods. For example, biosynthetic pathways for non-natural amino acids can be generated in host cell by adding new enzymes or modifying existing host cell pathways. Additional new enzymes include naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided herein. Additional enzymes sequences are found, for example, in Genbank. Artificially evolved enzymes can be added into a cell in the same manner. In this manner, the cellular machinery and resources of a cell are manipulated to produce non-natural amino acids.

A variety of methods are available for producing novel enzymes for use in biosynthetic pathways or for evolution of existing pathways. For example, recursive recombination, including but not limited to, as developed by Maxygen, Inc. (available on the world wide web at.maxygen.com), can be used to develop novel enzymes and pathways. See, e.g., Stemmer (1994), *Rapid evolution of a protein in vitro by*

*DNA shuffling*, Nature 370(4):389-391; and, Stemmer, (1994), *DNA shuffling by random fragmentation and reassembly: In vitro recombination for molecular evolution*, Proc. Natl. Acad. Sci. USA., 91:10747-10751. Similarly, DesignPath™, developed by Genencor (available on the world wide web at genencor.com) is optionally used for metabolic pathway engineering, including but not limited to, to engineer a pathway to create a non-natural amino acid in a cell. This technology reconstructs existing pathways in host organisms using a combination of new genes, including but not limited to those identified through functional genomics, molecular evolution and design. Diversa Corporation (available on the worldwide web at diversa.com) also provides technology for rapidly screening libraries of genes and gene pathways, including but not limited to, to create new pathways for biosynthetically producing non-natural amino acids.

Typically, the non-natural amino acid produced with an engineered biosynthetic pathway as described herein is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and a non-natural amino acid is generated, in vivo selections are optionally used to further optimize the production of the non-natural amino acid for both ribosomal protein synthesis and cell growth. The non-natural amino acids described herein may be synthesized using methodologies described in the art or using the techniques described herein or by a combination thereof.

Product Characterization

Comprehensive characterization of biotherapeutics is necessary to satisfy safety standards set by regulatory agencies and to help ensure protein drug efficacy. Biopharmaceutical characterization is required throughout all stages of drug development and manufacturing. Therefore, it is paramount to monitor product quality during each stage of cell line development, engineering, and cell culture process development to ensure the right clone is selected as the product quality and productivity are often dependent on both clone and cell culture conditions. During clone selection processes, emphasis is placed on product quality parameters that are likely to be clone specific. These parameters include, for example, enzymatic processes, such as glycosylation and proteolytic clipping, and genetic issues, such as mutations, frame shifts, and splices, but are not limited to such. Emphasis is also placed on molecular parameters that are known to contribute to biological activity. For example, antibody-dependent cellular cytotoxicity (ADCC) relies on fucosylation, and complement-dependent cytotoxicity (CDC) is dependent on galactosylation. Observed differences between clones in the extent of chemical modifications, such as oxidation or deamidation, may be narrowed or eliminated through purification process optimization or by adjustment of cell culture process parameters and will be less significant. (Lewis et al, 2010).

In embodiments of the present invention, the impact of CRISPR-Cas9 genome editing and single cell cloning on the product quality of a cell or cell line expressing a biotherapeutic is examined. Product quality attributes assessed during clone selection of CRISPR-Cas9 engineered cells can include molecule integrity, aggregation, glycosylation and charge heterogeneity, but are not limited to such. Molecule integrity is clone dependent and can be caused by genetic issues or proteolytic clipping. Various methodologies, techniques and assays, all well known to one of skill in the art, can be used to assess molecule integrity with the criteria to avoid amino acid sequence mutation or truncated antibodies. Such methodologies, techniques and assays can include, but is not limited to, cDNA sequencing, peptide mapping, CE-SDS or SDS-PAGE. Aggregation can be measured using, for example, size exclusion chromatography (SEC). The criteria for this analysis is to avoid high level of aggregation which can be immunogenic. Some levels of aggregation can be reduced by cell culture process optimization or removed through purification process optimization. Glycosylation is another important molecular and posttranslational attribute that is highly dependent on the cell line. HPLC or CE based glycan assays, well known in the art, are commonly used for glycosylation assessment at the clone selection stage with the goal of avoiding high levels of unusual glycosylation forms. Charge heterogeneity, which can occur due to chemical modification(s), is highly dependent on cell culture processes and therefore has a less significant role during the clone selection stage. Therefore, in embodiments of the present invention disclosure are provided methods, techniques and assays by which to determine clone specific product quality parameters of a cell or cell line expressing a biotherapeutic of the invention including, for example, anti-Her2, anti-CD70, or anti-PSMA expressing cell or cell line, but not limited to such.

Intact mass spectrometry (MS) provides information on the accurate mass of the protein and the relative abundance of its isoforms. Size exclusion chromatography (SEC), also known as molecular sieve chromatography, is a chromatographic method in which molecules in solution are separated by their size, and in some cases molecular weight. In the present invention, MS was utilized in demonstrating that for the engineered clones and parental cell lines generated, the primary amino acid sequence is the same as deduced from the cDNA sequence in confirming the identification of the mAb. SEC was also modified and utilized for determination of purity and manufacturing consistency of monoclonal antibodies (mAb) generated.

Kits

Kits are also a feature of the invention where the kit includes one or more containers containing any of the components of the invention. The kit can contain one or more of an engineered nucleic acid molecule or polynucleotide sequence comprising or encoding an orthogonal aminoacyl tRNA synthetase (O-RS), and/or an orthogonal suppressor tRNA (O-RNA), and/or a selector codon-containing gene of interest. The kit can include at least one unnatural amino acid. In another embodiment, the kit can contain a cell or line together or separately from an orthogonal aminoacyl tRNA synthetase (O-RS), an orthogonal suppressor tRNA (O-tRNA), or a selector codon-containing gene of interest. Any of the components, materials disclosed herein can be provided separately or together in one or more containers. In another embodiment, the kit further comprises instructional materials for producing the polypeptide or protein of interest.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Figure 1B:
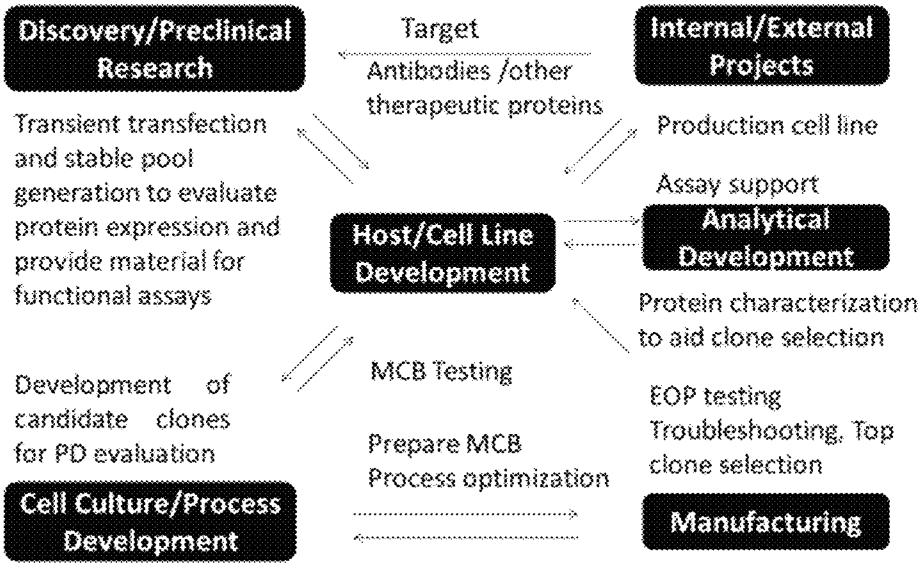

Example 1: The Strategy of Utilizing Platform Cell Line Engineering in Drug Development Industry: From Discovery to Manufacturing In the perspective of industry, platform cell line development not only supports every stage of drug development by providing stage appropriate material, but also generates stable, well-characterized production cell line prior to introduction of the product to the clinics and commercialization (FIG. 1A and FIG. 1B). To support every stage of drug development efficiently, multiple ways to provide material including transient, stable bulk pool, stable cell line was developed as illustrated in FIG. 1A and FIG. 1B. For antibody candidate molecule selection, transient expression was utilized to provide small amount product rapidly. Stable bulk pool is an alternative to provide large amount of material for developability study (purification, formulation, analytical method development) up to IND-enabling toxicology study (100-200 g) in 8 weeks. Once the lead molecule was determined, the stable cell line was generated in 6 months with titer up to 1.5 g/L. This provides support for clinical trial and potential commercialization.

Figures 2, 3A:
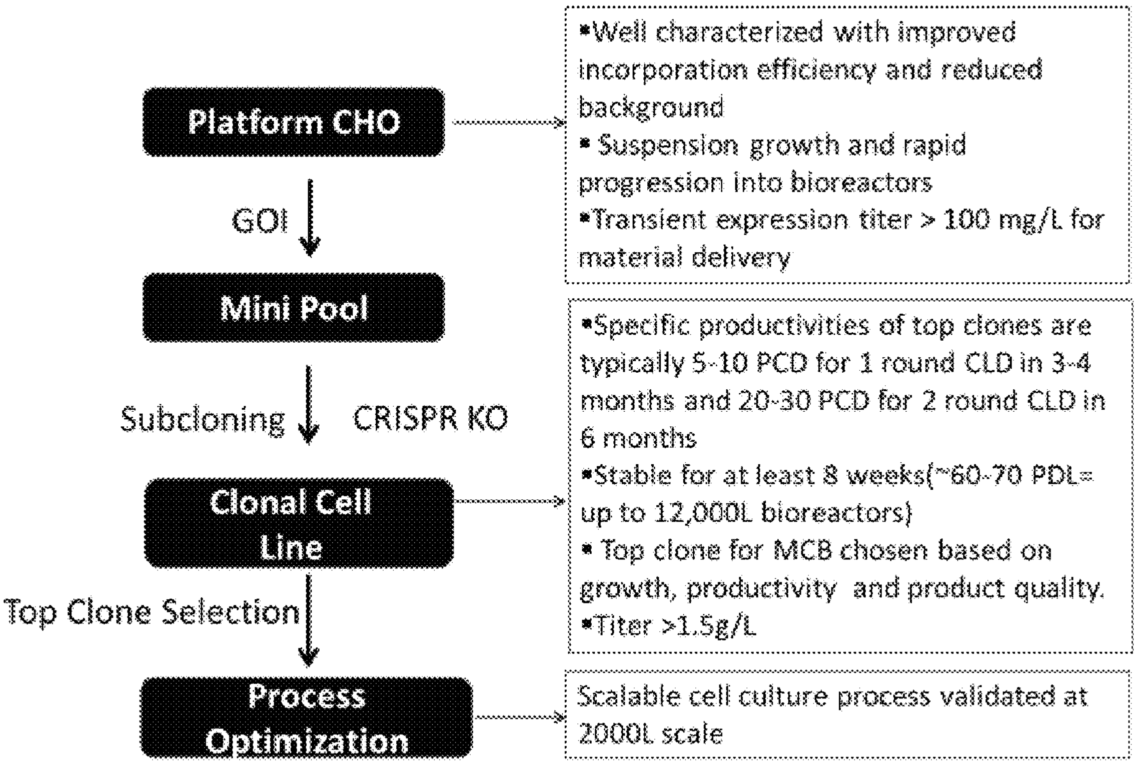
FIG. 2 depicts a general procedure of utilizing a platform cell line in the development of high production cell line.
FIG. 3A-FIG. 3C depict strategies for optimizing of high production cell line development, including optimization of high production cell line development from several aspects such as FACS-dependent single cell deposition (FIG. 3A), CRISPR knock out (FIG. 3B), and cell line development process optimization (FIG. 3C). FACS SCD yields 3-fold of monoclonal outgrowths than traditional LDC (FIG. 3A).

Example 2: A General Procedure of Utilizing Platform Cell Line in the Development of High Production Cell Line FIG. 2 depicts a flowchart for stable cell line development. The inventors employed this strategy to generate high producing, stable, well-characterized production cell lines scalable to industry standard manufacturing, to support clinical trial and commercialization while maintaining the desired safety and efficacy profiles of therapeutics. Mammalian expression vector carrying a gene of interest (GOI) and selectable marker(s) was transfected into engineered CHO platform cell line to generate mini-pool (MP) in 96 well. After selection and screening, the top MPs were plated as single cell per well using FACS followed by high resolution imaging to derive clonal cell line. The single cell derived cell lines were screened and the top clones transferred to cell culture group for process development. Final clone selection for manufacturing clinical material was based on growth, productivity and PQ. The whole CLD process takes 6 months and the cell-specific productivity was 20-30 picogram per cell per day. Stable for greater than 10 weeks to support 12,000 L bioreactor manufacturing, cell line and fed-batch process can be scaled up to 2000 L so far to support the ongoing clinical trial.

Example 3: Optimization of High Production Cell Line Development

Figure 3B:
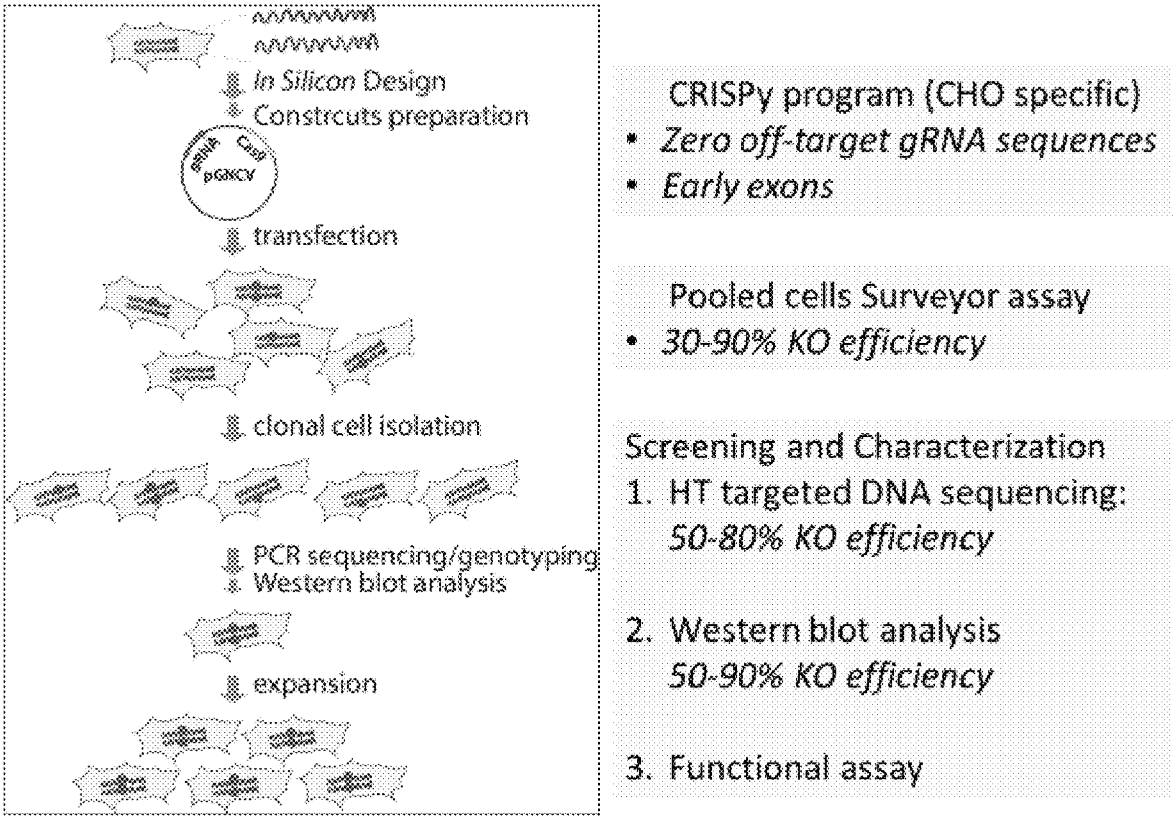
Figure 3C:
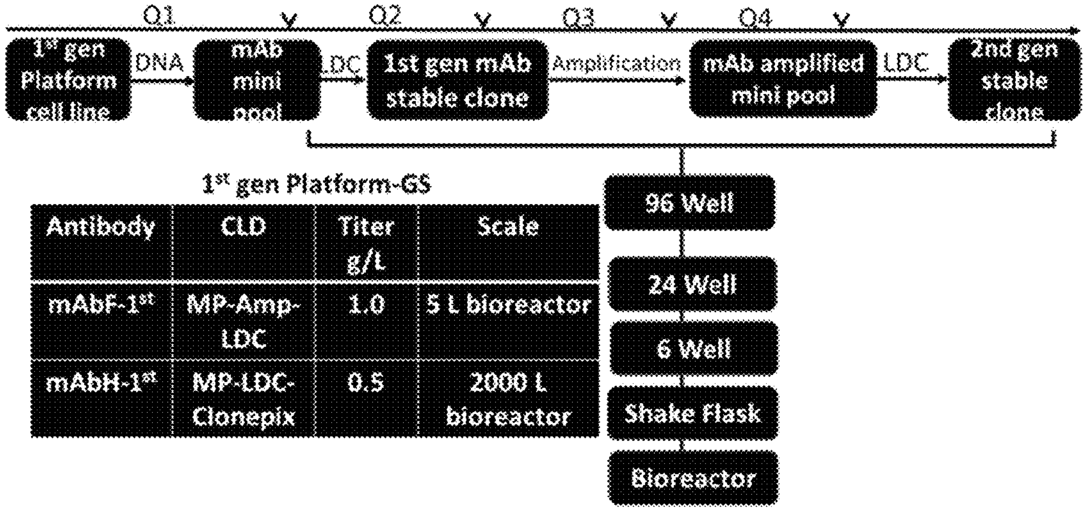

Optimization of high production cell line development can be achieved from several aspects such as FACS-dependent single cell deposition (FIG. 3A), CRISPR knock out procedure (FIG. 3B) and cell line development process optimization (FIG. 3C).

Regulatory guidance (ICH Q5D) instructs cloning the cell substrate “from a single cell progenitor” during cell line development. Over the last several years an expectation to provide high assurance of clonality has been established (Kennett, 2014; Novak, 2017; Welch, 2017) by the FDA and industry. The FDA has recommended that two-rounds of limiting dilution cloning (LDC) at sufficiently low seeding densities (<0.5 cells/well) provides acceptable probability that a cell line is clonal. More, recently, one-round of cloning through FACS or LDC with sufficient supporting justification, such as use of imaging technology, has provided acceptable assurance of clonality when using validated methods. The inventors thus modified and validated FACS single cell deposition (FACS SCD) coupled with high resolution imaging as one-round of cloning step in the cell line development process to shorten the time line as well as satisfy regulatory requirement for assurance of clonality.

As shown here (FIG. 3A), compared to traditional limiting dilution cloning (LDC), FACS SCD generated comparable deposition and outgrowth rate. However, efficiency of isolating monoclonal outgrowth (ratio of number of wells containing colonies derived from single cell divided by total number of wells) using FACS approach is 1.5-fold of that using LDC (49% VS 32%), saving significant time and resources on imaging and screening. Extensive optimization in FACS instrumentation and centrifugation g-force variation along with thorough image analysis for each well was conducted to validate the approach. Probability of monoclonality of the single cell derived colony was observed to be >99.5%.

Genetic engineering of the production cell line using CRISRR-cas9 genome editing technology has been tested to target a panel of genes to improve the cell growth and productivity while maintaining the desired product quality. The CRISPR knockout procedure is illustrated in FIG. 3B. A web-based target finding tool, CRISPy, was used to rapidly identify gRNA target sequences preferably in the early exons with zero off-target in the CHO-K1 cells. The gRNAs were cloned into mammalian expression vector pGNCV co-expressing with CHO codon-optimized version of Cas9. Production cell line was transfected with vector pGNCV to generate pool of cells followed by cloning to identify single cell isolates with gene knockout. The indel (insert/deletion) frequency from composite results of multiple projects was 30-90% and 50-80% for the pool of cells and single cell isolates, respectively. The Western blot reconfirmed the knock out efficiency as 50-90% for the DNA sequencing verified knock out single cell isolates. The knockout single cell clones were subjected to further assessment for productivity, growth, apoptosis assay and product quality to select a production clone for cGMP manufacturing. The validated targets used for knockout were tested using the production cell line. This proved to be beneficial for assessing productivity and growth and was applicable to disruption in the platform cell line host using CRISPR to increase efficiency of isolating high producing cell line for future gene of interest.

The cell line development process has also been optimized along with platform cell line evolvement. Using the first platform cell line as host, it takes three to four steps (or 9 months to 12 months) to generate a production cell line producing titer 0.5-1 g/L (FIG. 3C). Current cell line development process has been shortened to two steps or 6 months, attributed to improved platform cell line and one-step cloning as illustrated in (FIG. 2).

Example 4: Platform Cell Line Exhibits Excessive Apoptosis in the Culture

Figure 4A:
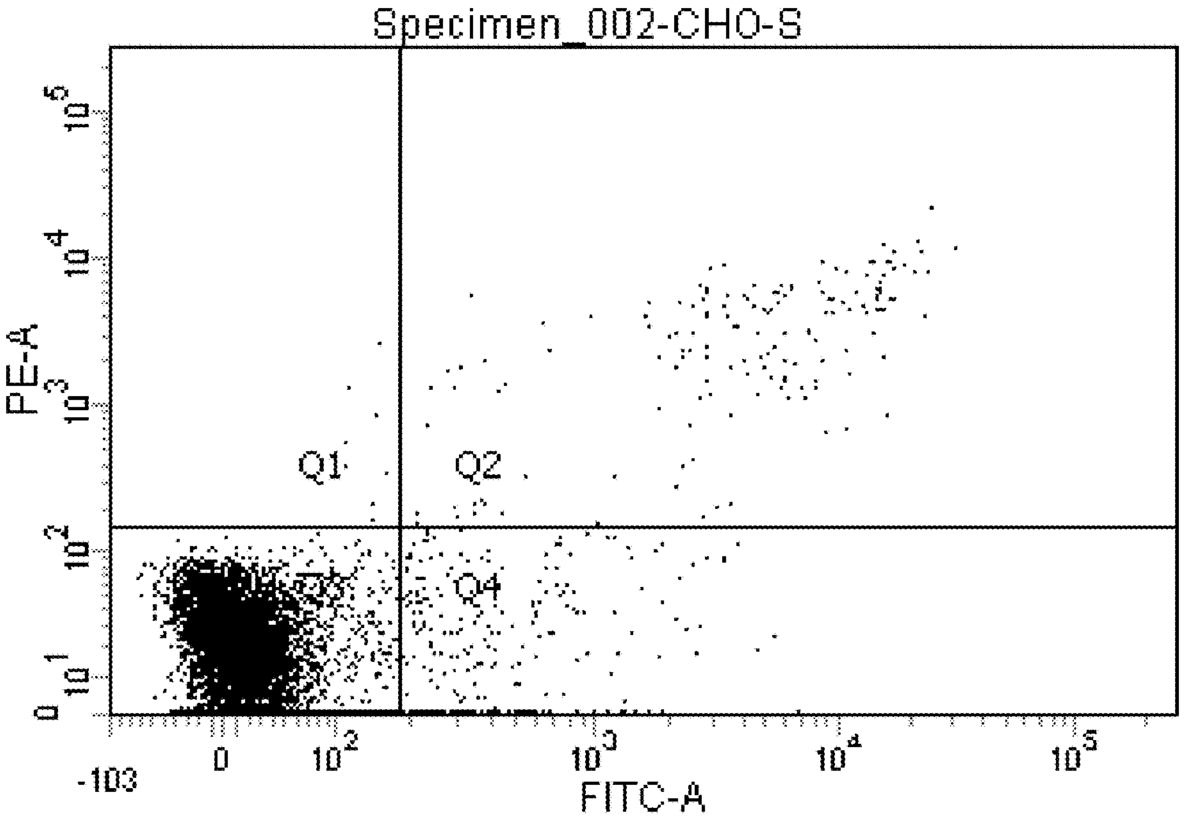
FIG. 4A-FIG. 4C. Observation of apoptosis in the cells from platform cell line-4E2. Annexin V assay was used to evaluate the viability of CHO-S cells (FIG. 4A) and platform cell line 4E2 (FIG. 4B) containing genetically incorporated orthogonal pair tRNA/aminoacyl-tRNA synthetase incorporating para-acetyl-L-phenylalanine specifically.
Figures 4B, 4C:
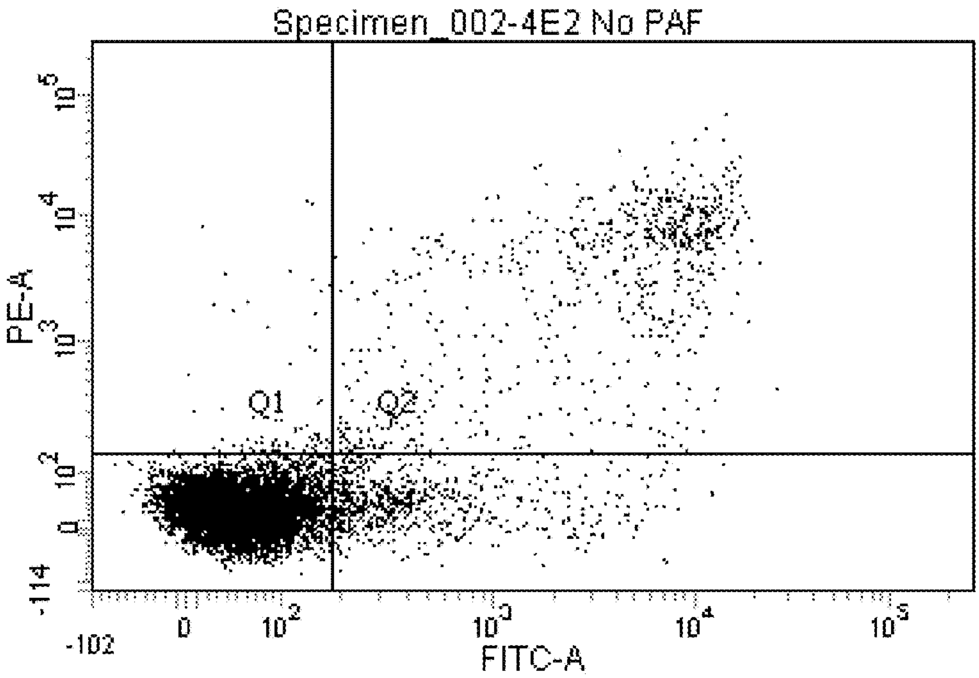

Annexin V assay was used to evaluate the viability of CHO-S cells and a platform cell line 4E2 that contains genetically incorporated orthogonal pair of tRNA/aminoacyl-tRNA synthetase specific for para-acetyl-L-phenylalanine. As shown in FIG. 4A, FIG. 4B and FIG. 4C, in comparison to CHO-S cells (viability is 96%), 4E2 exhibited excessive apoptosis (viability is 85%). Observations show 4E2 cells that have incorporated tRNA synthetase and tRNA pair (specific to for, example, non-natural amino acid para-acetylalanine, pAF) exhibited excessive apoptosis than its counterpart cells, CHO-S cells.

Example 5: Design and Preparation of BAX- and BAK-CRISPR Constructs

Figure 7:
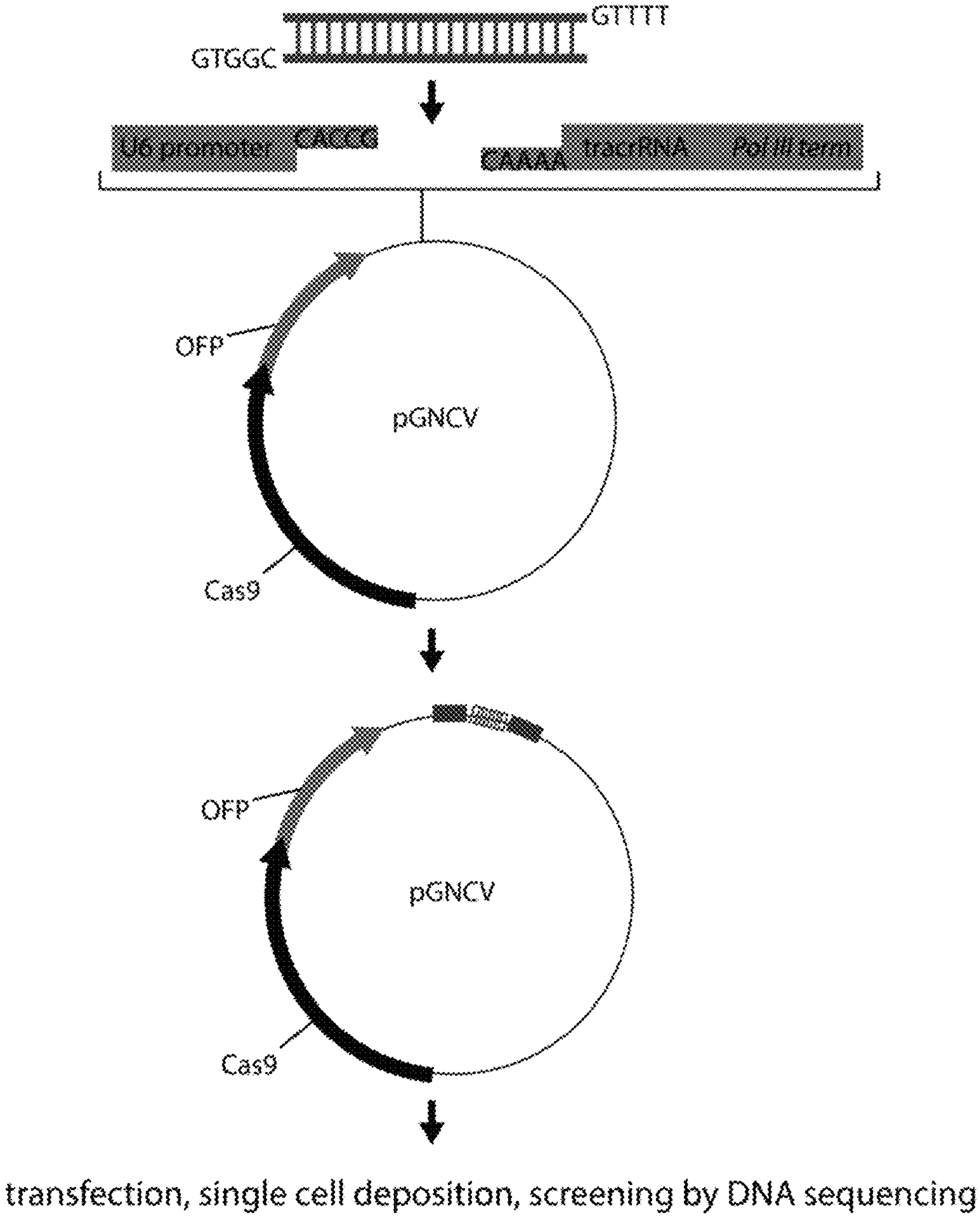
FIG. 7. BAX or BAK CRISPR constructs. The design of CRISPR plasmids used in BAX or BAK knockout experiments is depicted. Gencart CRISPR Nuclease Vector (pGCNV) is a commercially available vector from Thermo Fisher scientific, (San Diego, CA). The complete form of pGCNV plasmid is prepared by inserting an oligo-duplex into the cut-open pGCNV vector that contains a slot for oligo duplex that is designed with specific 19-nucleotide-long gRNA sequences to target gene site individually (see Table 1 elsewhere herein).

CRISPR constructs were designed to recognize target sites in BAX or BAK gene and make double strand breaks in CHO cells after transfection. Exemplary designs are shown in FIG. 5, FIG. 6 and FIG. 7.

Knockout of a gene can be done using a sequential or a simultaneous procedure. BAX and BAK double knock out can also be achieved by sequential knock out procedure. In general, the first step is to apply three BAX targeted gRNA constructs on anti-HER2 expressing cell line. After following similar produced used in simultaneous knock out procedure, a cell line that has BAX knock out is isolated. Using this cell line, two BAK targeted gRNA constructs are applied to achieve BAK knock out. After verification by genomic DNA sequencing, BAX and BAK double knock out cell line is confirmed being achieved by such a sequential procedure.

Figure 5:
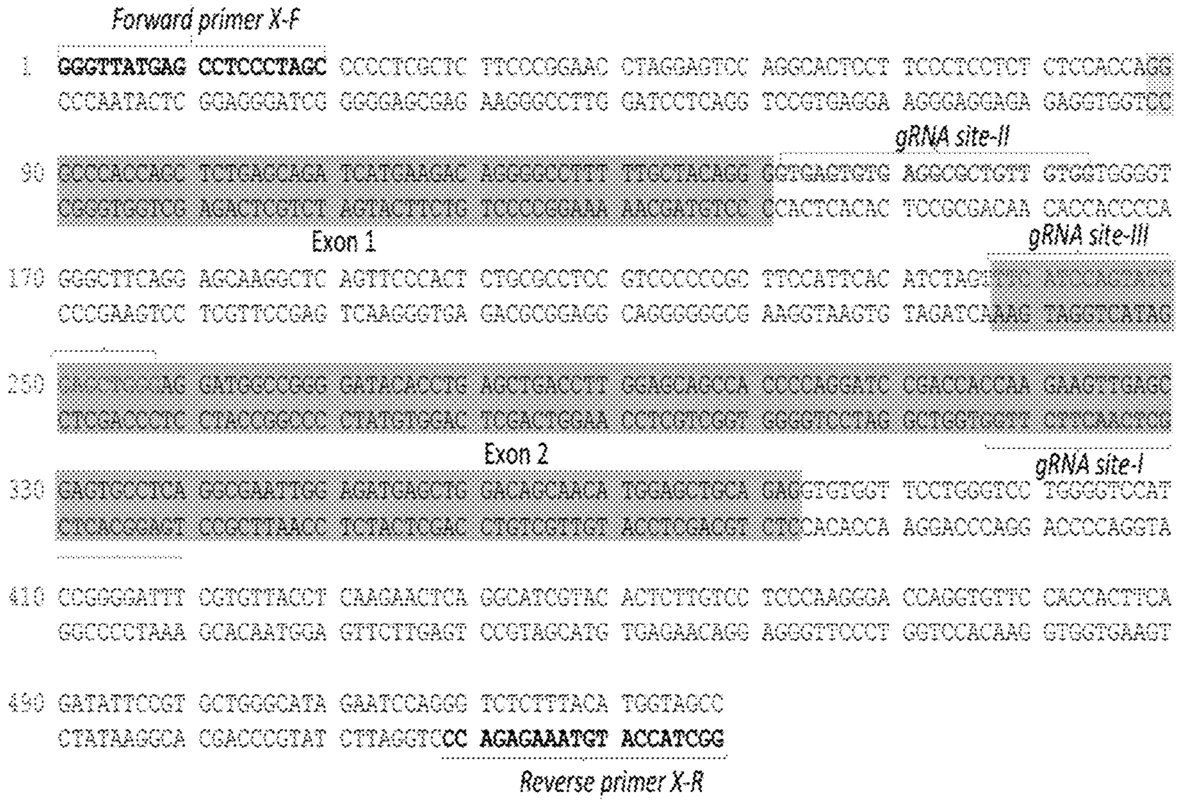
FIG. 5. CRISPR gRNA design of targeted BAX gene in CHO cells. Genomic DNA sequence of BAX gene in CHO cells in which three gRNA sequences have been annotated are depicted. Genomic DNA sequence of BAX gene, exon 1 and exon 2 are shown in gray shade. The other sequence of BAX is shown in plain text. Primers used in PCR and sequencing are shown at the beginning and the end of the sequence as forward primer and reverse primer respectively.

CRISPR gRNA design of targeted BAX gene in CHO cells is illustrated in FIG. 5. As shown, three gRNA sites targeting BAX gene in CHO cells were designed using an online CRISPR gRNA design tool specific to CHO-K1 genome (see on the world wide web at staff.biosustain.dtu.dk/lacb/crispy/). Genomic DNA sequence of BAX gene, exon 1 and exon 2 are shown in gray shade. The other sequence of BAX is shown in plain text. Primers used in PCR sequencing are shown at the beginning and the end of the sequence as forward primer and reverse primer respectively. As shown in Table 1, three BAX sites (each has 19-nucleotide-long sequence, the -NGG PAM (protospacer adjacent motif) sequence is omitted during design due to the nature of plasmid pGCNV that is cut-open and has two sticky ends, as shown in FIG. 7) are as follows:

```
site-I
                         (SEQ ID NO: 1)
(AGGCACTCGCTCAACTTCG),

site-II
                         (SEQ ID NO: 2)
(TGAGTGTGACCGGCTGTTG)
and

site-III
                         (SEQ ID NO: 3)
(TTTCATCCATGTATCGAGCT).
```

As shown in FIG. 6, CRISPR was used to design gRNA of targeted BAK gene in CHO cells. FIG. 6 depicts genomic DNA sequence of BAK gene in CHO cells in which two gRNA sequences have been annotated. Genomic DNA sequence of BAK gene, exon 2 and exon 3 are shown in gray shade. The other sequence of BAK is shown in plain text. Primers used in PCR sequencing are shown at the beginning and the end of the sequence as forward primer and reverse primer respectively. Three BAK sites shown in Table 1, are as follows:

```
Exon 2
                         (SEQ ID NO: 4)
BAK-IGAACAAATTGTCCATCTCG,

Exon 3
                         (SEQ ID NO: 5)
BAK-IIATGCTGTAAGAACGGGAGT,

Exon 3
                         (SEQ ID NO: 6)
BAK-IIIGAAGCCGGTCAAACCACGT.
```

CRISPR plasmids used in BAX or BAK knockout experiments were also designed as shown in FIG. 7 using a commercially available vector, Geneart CRISPR Nuclease Vector (pGCNV), (Thermo Fisher Scientific). The complete form of pGCNV plasmid was prepared by inserting an oligo-duplex into the cut-open pGCNV vector containing a slot for oligo duplex and designed with specific 19-nucleotide-long gRNA sequences to target a gene site individually (see Table 1 elsewhere herein).

To form an oligo duplex that can be inserted into pGCNV, five (5) pairs of oligos were synthetized as disclosed in Table 3 below.

TABLE 3

Oligo sequences used to prepare BAX and BAK knockout CRISPR constructs

| SEQ ID | Name | Oligo sequence |
|---|---|---|
| 83 | BAX-I-F | AGGCACTCGCTCAACTTCGGTTTT |
| 84 | BAX-I-R | CGAAGTTGAGCGAGTGCCTCGGTG |
| 85 | BAX-II-F | TGAGTGTGACCGGCTGTTGGTTTT |
| 86 | BAX-II-R | CAACAGCGCCTCACACTCACCGGTG |
| 87 | BAX-III-F | TTTCATCCATGTATCGAGCTGTTTT |
| 88 | BAX-III-R | AGCTCGATACTGGATGAAGACGGTG |
| 89 | BAK-I-F | GAACAAATTGTCCATCTCGGTTTT |
| 90 | BAK-I-R | CGAGATGGACAATTTGTTCCGGTG |
| 91 | BAK-II-F | ATGCTGTAAGAACGGGAGTGTTTT |
| 92 | BAK-II-R | CACTCCCGTTCTTACAGCATCGGTG |

To generate double-stranded oligonucleotides, each oligo pairs is incubated at final concentration of 50 uM in Oligonucleotide Annealing buffer at 95° C. for 4 minutes before cooling down to 25° C. for 5-10 minutes. After 10-fold dilution (5 uM), oligonucleotide duplex can be used in ligation procedure. Ligation can be done with Roche quick ligation kit (Roche). In a 21 ul reaction containing 3 ul of pGCNV vector, 1 ul of oligo duplex, 2 ul of DNA dilution buffer, 4 ul of water, 10 ul of T4 DNA ligase buffer and 1 ul of T4 ligase. Reaction mixture was incubation at room temperature for 5 minutes. 3 ul of ligation mixture can be used for transformation of *E. coli* to screen for positive clones.

Example 6: Examples of Non-Natural Amino Acids Used in the Present Invention The invention involves site-specific incorporation of non-canonical or non-natural amino acids in a gene of interest using an orthogonal aminoacyl-tRNA synthetase/transfer RNA pair discussed elsewhere herein. FIG. 8 provides a representative number of non-natural amino acids that can be used. In an exemplary manner, one such non-natural amino acid para-acetyl-L-phenylalanine (pAF) was added in the culture medium to initiate the production of fully assembled gene of interest, for example biotherapeutics including monoclonal antibodies, with site-specific incorporation of pAF.

Example 7: Generation and Analysis of BAX/BAK Deficient anti-HER2 Expressing Cell Lines Simultaneous ablation of BAX and BAK was conducted using CRISPR technology. Transient transfection was performed using three BAX targeted gRNA constructs and two BAK targeted gRNA constructs on anti-HER2 expressing cell line L082. Transfection of plasmids were done with electroporation. During electroporation, 6 million cells were mixed with 2 ug DNA plasmid in 100 ul of electroporation solution. Cells were transfected in an Amaxa Nucleofector II (Lonza) using program U-023 and recovered in 0.5 ml warm medium. Surveyor was performed on the transfected pool of cells to measure the knock out efficiency as disclosed in Example 3, FIG. 3B. Seven days after being transfected with three BAX targeted gRNA constructs together with two BAK targeted gRNA constructs simultaneously, the cells were subcloned at a seeding density of 0.5 cell/well into 96-well plates into single clones using limiting dilution method. Each single cell in the 96-well plate was grown for about 2-3 weeks to generate a sufficient number of cells to be used for further genetic analysis. Single-cell derived clones were selected and screened through 96-well, 24-well and 24-deep well for productivity, growth, and genotyping by targeted DNA sequencing.

Example 8: DNA Analysis of BAX and BAK Deficient Anti-HER2 Expressing Clones

Figure 9:
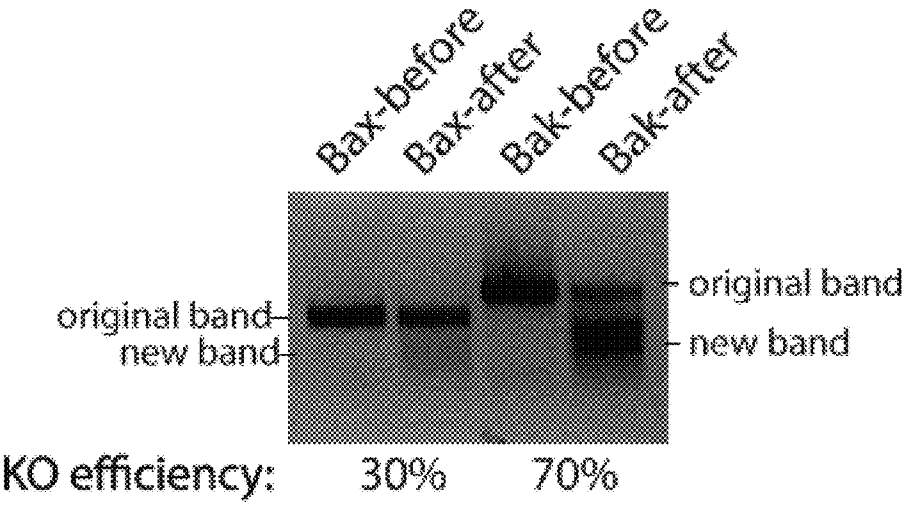
FIG. 9. Surveyor assay of anti-HER2 expressing cell populations in which BAX or BAK was knocked out using CRISPR. Surveyor assay analysis of knockout efficiency during BAX or BAK knockout using CRISPR is depicted. Diminishing of the top band and appearance of the bottom new bands indicate the efficiency that can be quantified by densitometry analysis of the scanned image by Image J software. The ratio of the original band before and after CRISPR knockout (KO) was used to measure the knockout efficiency. The knockout efficiency for BAX and BAK was 30% and 70% respectively, resulting in the calculated double knockout efficiency of approximately 21%.

BAX and BAK inactivated CHO cells were generated and analyzed at the genetic level. Three plasmids encoding three different gRNA sequences targeting BAK sites were co-transfected into CHO cell-derived stable cell lines that has been engineered to have pAF-RS and pAF-tRNA plus anti-HER2 gene or fragment thereof. 72 hours after transfection, genomic DNA was isolated and a portion of the BAK locus was PCR amplified using the oligos K-I-II-F and K-I-II-R (Table 2; 5'-CAGACAGCCTTCTCTTGCT-3' (SEQ ID NO: 45) and 5'-AGAGCTCCTGAGAGGCATGA-3' (SEQ ID NO: 46)). PCR was performed using Phusion High-Fidelity PCR master mix (New England Biolabs, Ipswich, MA). The conditions were as follows: after an initial denature at 95° C. for 2 min, 30 cycles of PCR were performed with a 95° C. denature for 20 second, followed by a 30 second annealing at 60° C. step, followed by a 1 minute extension at 72° C. After the 30 cycles, the reaction was incubated at 72° C. for 5 minutes then at 4° C. indefinitely. PCR products were used in Surveyor assay analysis to evaluate knockout efficiency. Surveyor assay detection was performed using Surveyor Mutation detection kit from IDT (Integrated DNA Technology, San Diego, CA). Heteroduplex was formed using a thermocycler to mimic the naturally cooling down procedure of a heated oligo mixture. The following procedure was used in forming the heteroduplex: 95° C. for 10 minutes, followed by cooling down from 95° C. to 85° C. (−2.0° C./s), 85° C. incubation for 1 minute; cooling down from 85° C. to 75° C. (−0.3° C./s), 75° C. incubation for 1 minute; cooling down from 75° C. to 65° C. (−0.3° C./s), 65° C. incubation for 1 minute; cooling down from 65° C. to 55° C. (−0.3° C./s), 55° C. incubation for 1 minute; cooling down from 55° C. to 45° C. (−0.3° C./s), 45° C. incubation for 1 minute; cooling down from 45° C. to 35° C. (−0.3° C./s), 35° C. incubation for 1 minute; cooling down from 35° C. to 25° C. (−0.3° C./s), 25° C. incubation for 1 minute; and then at 4° C. indefinitely. Heteroduplex DNA (20 ul) was incubated with 1 ul of Surveyor Enhancer S (2 ul) and Surveyor Nuclease S (1 ul) at 42° C. for 60 minutes. 10 ul of digested sample was run on a 1% agarose gel side by side with 10 ul of undigested sample. As shown in FIG. 9, a Surveyor assay was performed on the transfected pool of cells to measure the knock out efficiency as disclosed in Example 3, FIG. 3B. Analysis of knockout efficiency was conducted in anti-HER2 expressing cell populations. The diminishing top band and appearance of the bottom new bands is indicative of the efficiency that can be quantified by densitometry analysis of the scanned image by Image J software. The ratio of the original band before and after CRISPR KO was used to measure the knockout efficiency. The knockout efficiency for BAX and BAK was 30% and 70% respectively, resulting in the calculated double knockout efficiency of appropriately 21%.

Duplicated plates of single-cell containing 96-well plates were used to perform genomic DNA isolation and DNA sequencing. QuickExtract solution was used in high-throughput isolation of genomic DNA. 150 ul of supernatant of cell culture was removed from the culture before adding 150 ul of QuickExtract solution. After being lysed at room temperature for 10 minutes, the cell lysates were transferred to fresh microtubes to be heated on heat block at 65° C. for 6 minutes followed by 98° C. for 2 minutes.

Genomic DNA extract was used for PCR amplification. The PCR products were then purified and were sequenced. Sequencing results were analyzed using alignment tools in Vector NTI software suite. Genomic sequence of genes (in this case, BAK gene) obtained on the worldwide web at CHOgenome.org was used as wild type sequence during alignment analysis.

Figure 10:
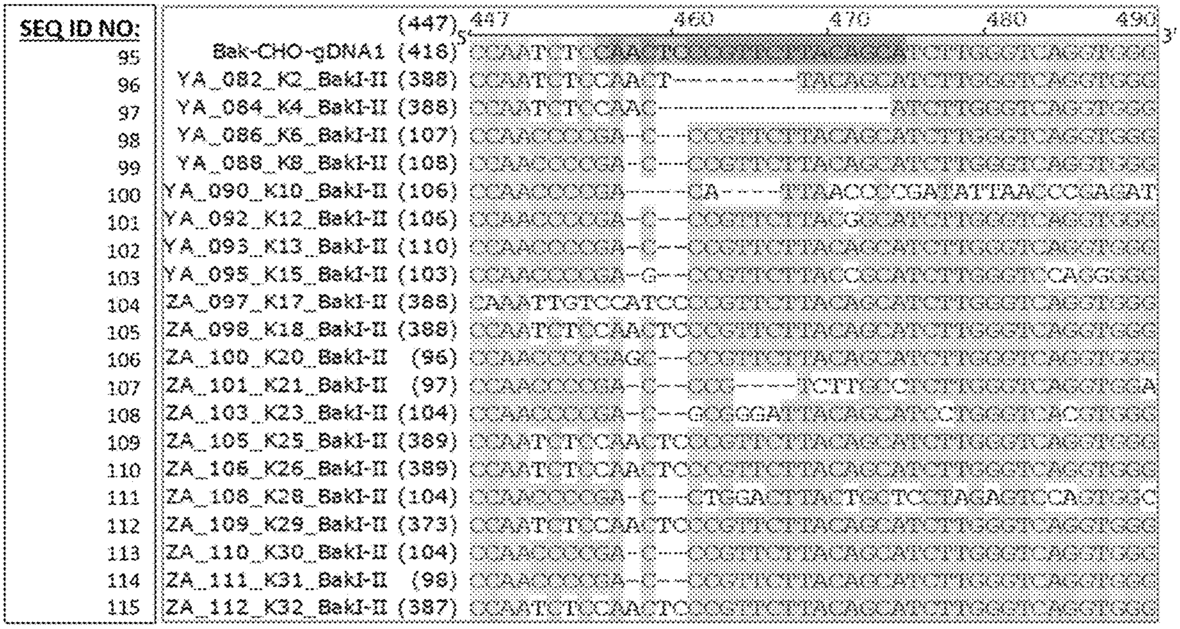
FIG. 10. DNA analysis of anti-HER2 expressing single cell clones with BAX and BAK gene knocked out using CRISPR. The DNA sequencing results of twenty single cell clones after BAK knockout using CRISPR are depicted. The top DNA sequence (Bak-CHO-gDNA1) is the DNA sequence of the genomic region of the original BAK gene. Only 'ZA_112_K32_BakI-II' clone has identical sequence to the original BAK gene. The other genes shown in FIG. 10 either have deletions or insertions in their sequences.

FIG. 10 depicts the DNA sequencing results of twenty single cell clones after BAK knockout using CRISPR. The top DNA sequence (Bak-CHO-gDNA1) is the DNA sequence of the genomic region of the original BAK gene. Only 'ZA_112_K32_BakI-II' clone has identical sequence to the original BAK gene. The other genes shown either have deletions or insertions in their sequences. Similar observations were noted with BAX (data not shown).

Figure 11:
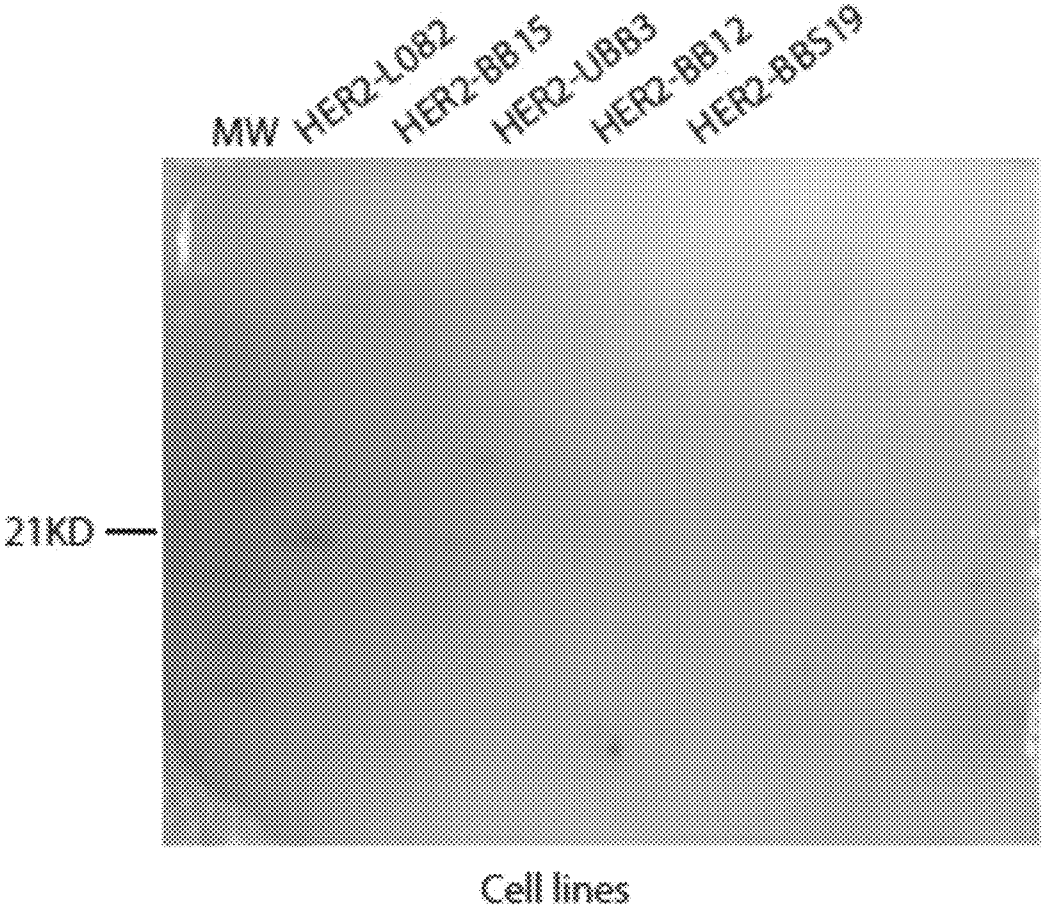
FIG. 11. Western blot analysis of BAX knockout confirmation in anti-HER2 expressing BAX knockout clones using CRISPR. BAX is a 21-KD protein that is shown as a band in L082 cells that have no gene knockout and express wild type BAX protein. The other clones showed no detectable expression of BAX protein except clone UBB3 that shows residual BAX expression.

Example 9: Protein Analysis of BAX and BAK Knockout in Anti-HER2 Expressing Clones The BAX and BAK knockout anti-HER2 expressing single cell derived cell lines were tested for BAX protein expression using Western Blot analysis (FIG. 11). Lysates from 6 million BAX/BAK double knockout cell lines were prepared by resuspending in 100 ul RIPA buffer (Abcam) plus protease inhibitors (Sigma tablets, Sigma). Lysates were incubated on ice for 1 hour before being centrifuged at 12,000 rpm for 20 minutes. Protein concentration was determined by BCA kit (Pierce). 20 ug of protein was used for Western blot. Protein extracts from different cell lines were probed with anti-BAX antibody (Abcam). As shown in FIG. 11, BAX/BAK double knockout cell lines such as BB15, BB12 and BBS19 did not express any detectable BAX proteins. In contrast, as a positive control cell line, L082, showed expression of full-length BAX, a 21-KD protein. It is noted that the UBB3 cell line expressed residual BAX although it was characterized to be genetically BAX-deficient by gene sequencing. Similar observations were noted with BAK (data not shown).

Figure 12A:
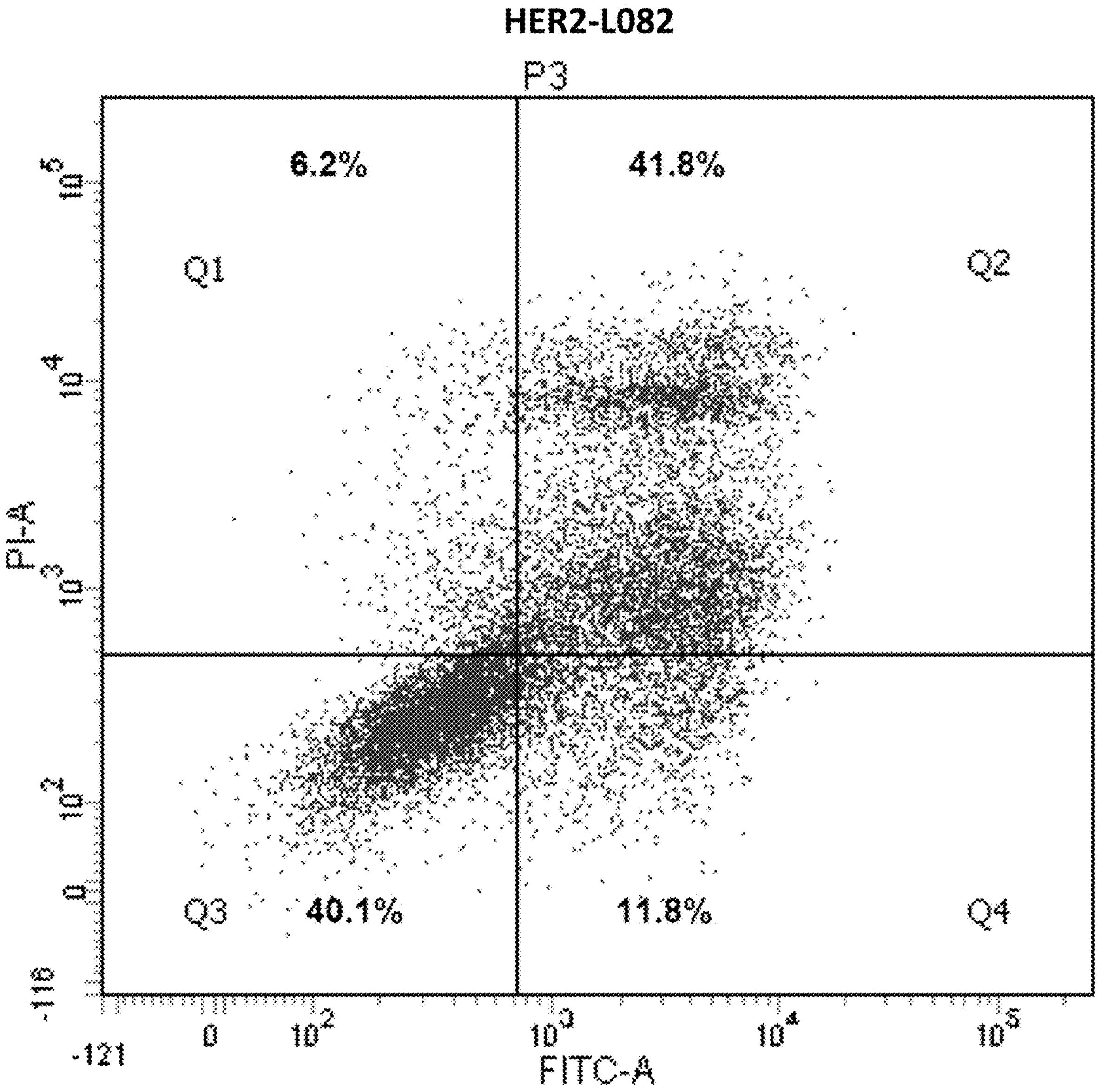
FIG. 12A-FIG. 12C. Apoptosis analysis of anti-HER2 expressing BAX/BAK knockout cell lines.
Figures 12B, 12C:
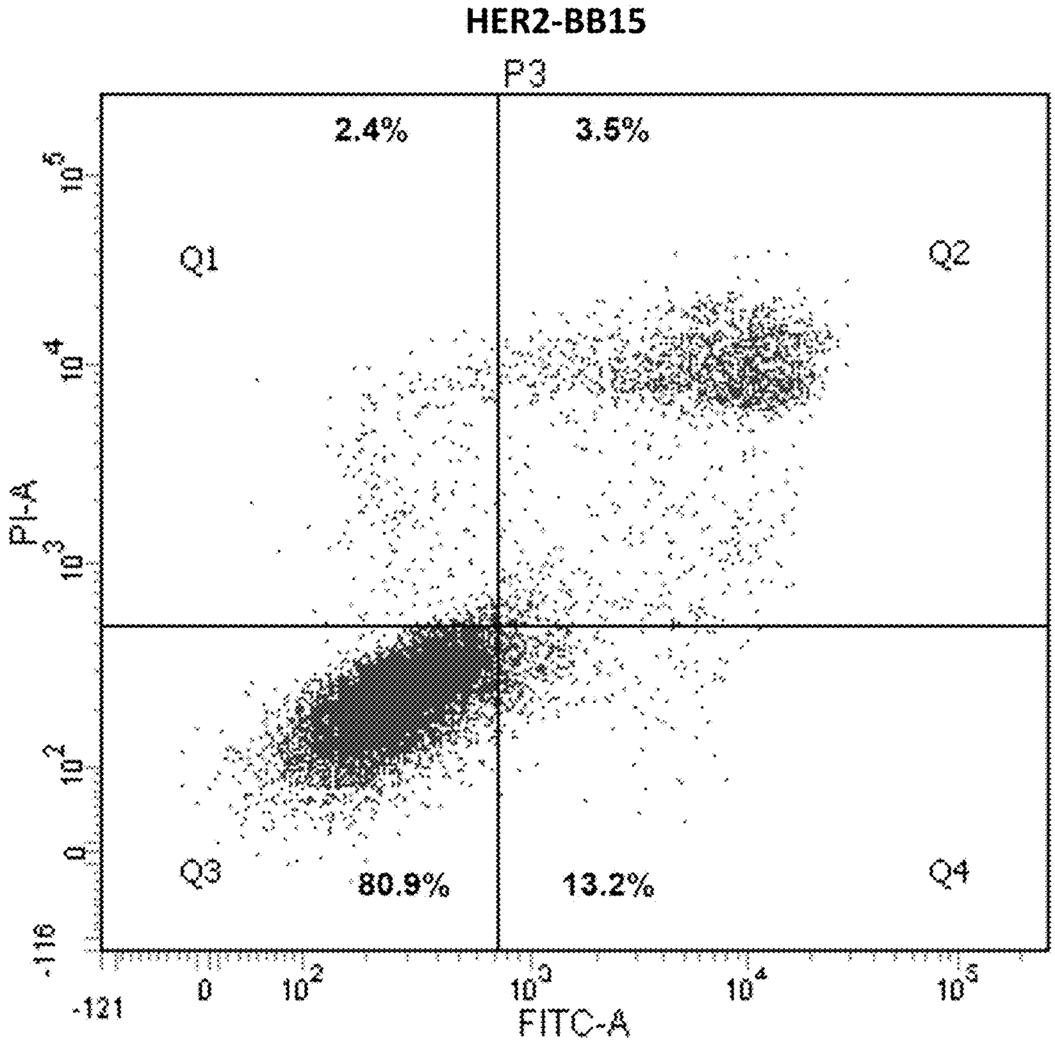

Example 10: Apoptosis is Prevented in BAX/BAK Deficient Anti-HER2 Expressing Cell Lines The BAX/BAK double knockout cell lines were tested for their resistance to apoptosis. The property of apoptosis resistance was evaluated during fed-batch procedure. Flow cytometry analysis of Annexin V staining of day-12 of the cells in fed-batch was performed. Standard protocol using FITC Annexin V apoptosis detection kit from BD Biosciences was followed under manufacture's recommended conditions. Cells can be divided into four stages and/or populations during apoptosis assay: normal viable cells stage (quadrant 3, Q3), early stage of apoptosis (quadrant 4, Q4), late stage of apoptosis (quadrant 2, Q2), and dead cells stage (quadrant 1, Q1). As shown in FIG. 12A, the normal (control) L082 cells that have no knockouts showed severe apoptosis as depicted in Q4 (11.8%) and Q2 (41.8%). In contrast, the BAX/BAK double knockout cell line (BB15) showed much improved viability (Q3, 80.9%) and resistance to apoptosis (Q4, 13.2%; Q2, 3.5%) as depicted in FIG. 12B. Hence, the apoptotic cells were observed to decrease from 53% to 17%.

Figure 13A:
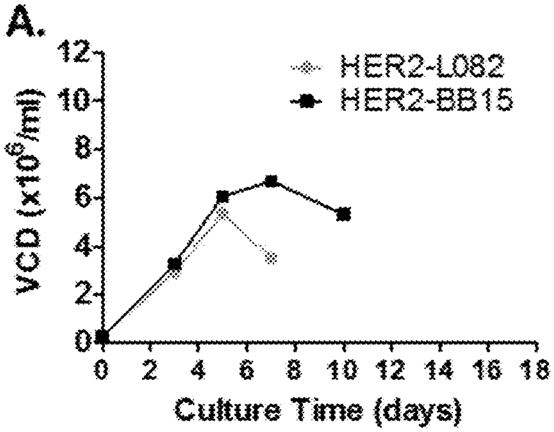
FIG. 13A-FIG. 13D. Promotion in anti-HER2 antibody production in BAX/BAK knockout cell lines in batch culture. The protein production changes in BAX/BAK double knockout cell lines are depicted. Protein productions are analyzed during batch production. Viable Cell Density (VCD, FIG. 13A). Cell Viability (FIG. 13B). During batch production (day 7), BAX/BAK double knockout cell line showed titer increase from 150 mg/L to 270 mg/L (FIG. 13C). Specific productivity (Qp) (FIG. 13D).
Figure 13B:
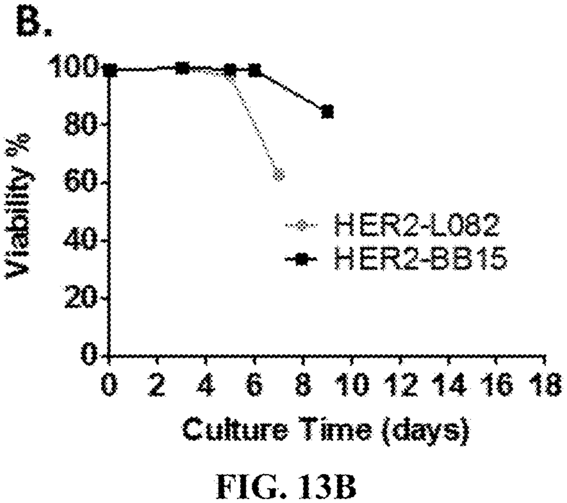
Figure 13C:
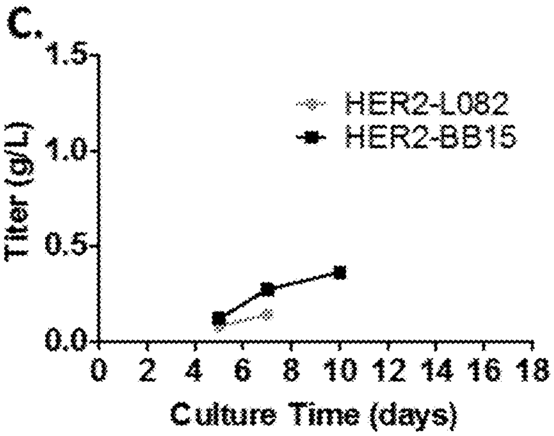
Figure 13D:
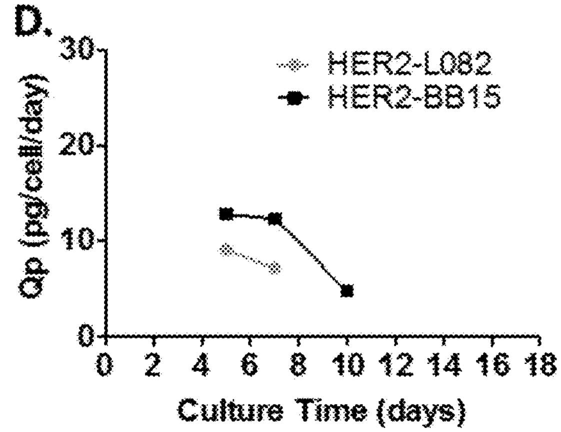

Example 11: Production of Recombinant Protein is Increased in BAX/BAK Deficient Anti-HER2 Expressing Cell Lines Productions of antibody were evaluated in both batch (FIG. 13A, FIG. 13B, FIG. 13C and FIG. 13D) and fed-batch procedures (FIG. 14A, FIG. 14B, FIG. 14C and FIG. 14D). Under batch culture conditions, non-natural amino acid pAF was added in the culture medium on day 3 to initiate the production of fully assembled anti-HER2 antibody with site-specific incorporation of pAF. As expected for anti-apoptosis engineering, the peak cell density as measured by viable cell density (VCD) of knockout cells (FIG. 13A) is 25% higher than parental cells and production time (FIG. 13B) extended up to 10 days from 7 days for parental cells. Surprisingly, the Day 7 daily Qp of knockout cells (FIG. 13D) was improved by 50% over parental cells, possibly due to maintained cellular activity resulting from anti-apoptosis engineering. BAX/BAK double knockout cell lines showed 1.8-fold increase in titer (270 mg/L vs. 150 mg/L) compared to parental cells (FIG. 13C) at day 7 of production.

Figure 14A:
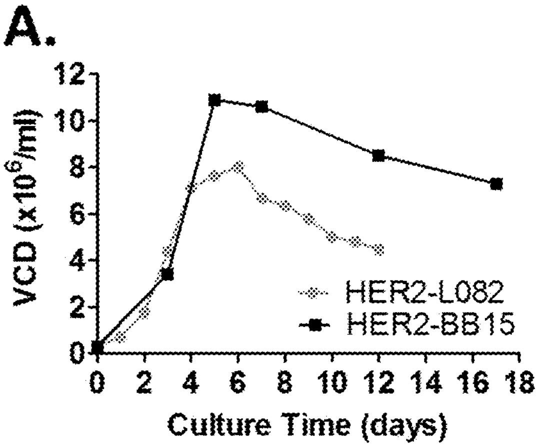
FIG. 14A-FIG. 14D. Promotion in anti-HER2 antibody production in BAX/BAK knockout cell lines in fed-batch culture. The protein production changes in BAX/BAK double knockout cell lines are depicted. Protein productions are analyzed during fed-batch production. Viable Cell Density (VCD, FIG. 14A). Cell Viability (FIG. 14B). During fed-batch production (day 14), BAX/BAK double knockout cell line shows titer increase from 450 mg/L to 1500 mg/L (FIG. 14C). Specific productivity (Qp) (FIG. 14D).
Figure 14B:
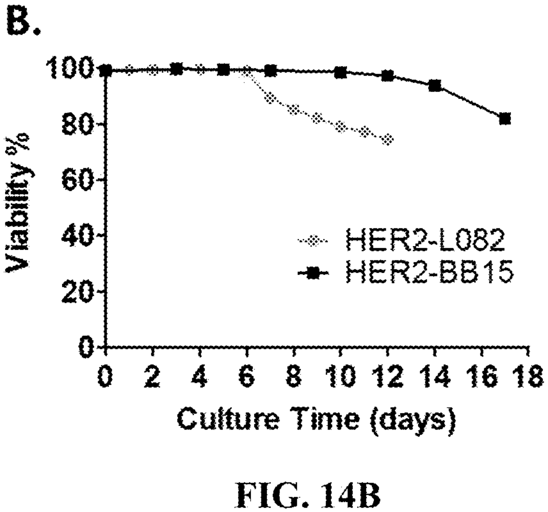
Figure 14C:
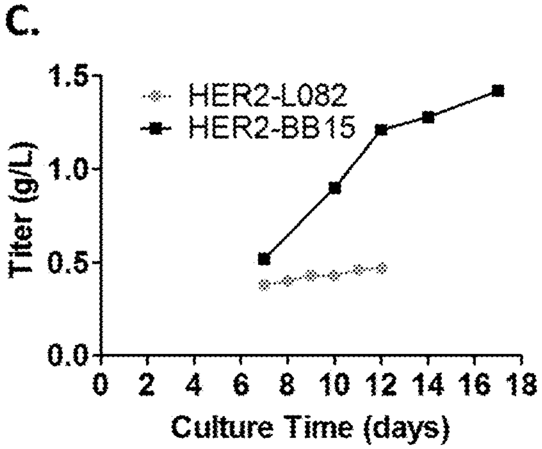
Figure 14D:
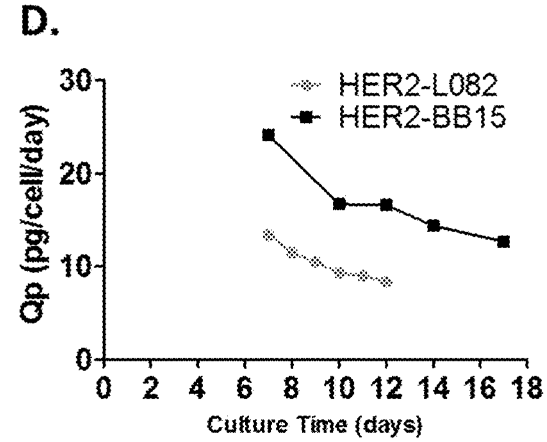

Similar trend was observed under fed-batch culture conditions (FIG. 14A, FIG. 14B, FIG. 14C and FIG. 14D), combination of improvement in growth based on peak cell density (VCD) as shown in FIG. 14A, production time (FIG. 14B) and cell-specific productivity (FIG. 14D) lead to 3.3-fold increase in titer for BAX/BAK double knockout cell lines (FIG. 14C) showing BB15 clone with titer of 1500 mg/L compared to parental cell line (L082, 450 mg/L).

Example 12: Product Quality of BAX/BAK Deficient Anti-HER2 Expressing Cell Lines Product quality was analyzed by intact mass spectrometry (MS) and size exclusion chromatography (SEC) using samples produced by fed-batch production from anti-HER2 expressing parental cell line and BAX/BAK double knockout anti-HER2 expressing cell line (Table 4). It was observed by MS that the primary amino acid sequence of the engineered clone and parental cell line is the same as deduced from the cDNA sequence confirming the identification of the mAb, (data not shown).

TABLE 4

Quality analyses of products from anti-HER2 expressing cell lines

| | SEC | | | Intact Mass (% Glycoform) | | | | |
|---|---|---|---|---|---|---|---|---|
| | HMW | Main | LMW | Man5 | G0 | G0F | G1F | G2F |
| HER2-BB15 | 4.4% | 92.6% | 3.1% | 0% | 1% | 77% | 21% | 2% |
| HER2-L082 | 6.0% | 89.0% | 5.0% | 2.4% | 3.2% | 64.4% | 25.4% | 4.5% |

As depicted in Table 4, product quality was analyzed using samples produced by fed-batch production from parental and BAX/BAK double knockout anti-HER2 expressing cell lines. The glycoform profiles assessed by MS were comparable before, (HER2-L082), and after knockout, (HER2-BB15), and within the normal distribution range for mAb at the clone selection stage. SEC showed that the percentage of high molecular weight (HMW) aggregates and low molecular weight (LMW) degraded species were both lower than 5% and comparable before and after engineering, indicating the knockout and single cell cloning procedure did not impact negatively on purity of product.

Example 13: Generation of BAX/BAK Deficient Anti-PSMA Expressing Cell Line

Simultaneous ablation of BAX and BAK using CRISRP technology was performed by transfection of three BAX targeted gRNA constructs and two BAK targeted gRNA constructs into anti-PSMA expressing cell line KO183. The BAX and BAK constructs used in this experiment were designed and prepared as described in the above Examples and illustrated in FIG. 5, FIG. 6 and FIG. 7 and Tables 1-3. CRISPR plasmids used in the knockout experiments relating to anti-PSMA were also designed as shown in FIG. 7 using a commercially available vector, Gencart CRISPR Nuclease Vector (pGCNV), (Thermo Fisher Scientific). The oligo duplex inserted into pGCNV, comprised five (5) pairs of synthetized oligos of SEQ ID Nos: 83 to SEQ ID No:92.

Figure 15:
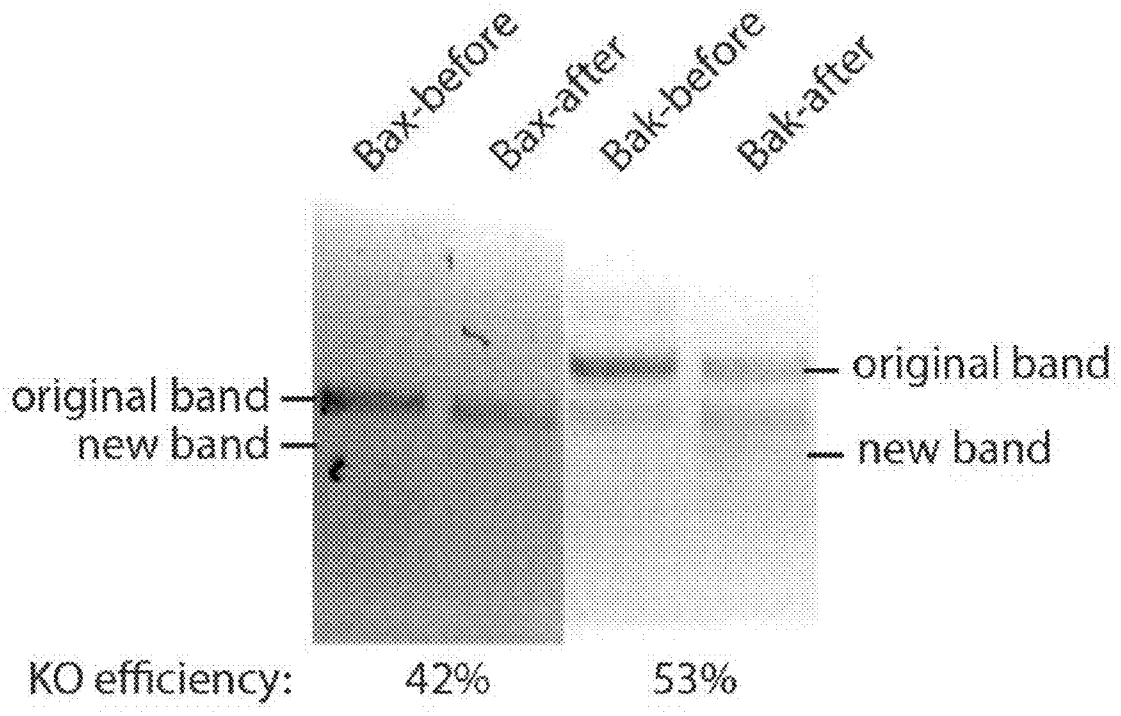
FIG. 15. Surveyor assay of anti-PSMA expressing cell populations in which BAX or BAK was knocked out using CRISPR. Surveyor assay analysis of knockout efficiency during BAX or BAK knockout using CRISPR is depicted. The ratio of the original band before and after CRISPR knockout (KO) was quantified by densitometry analysis of the scanned image by Image J software and used to measure the knockout efficiency. The knockout efficiency for BAX and BAK was 42% and 53% respectively, resulting in the calculated double knockout efficiency of approximately 20%.

Three plasmids encoding three different gRNA sequences targeting BAX sites and two plasmids encoding two different gRNA sequences targeting BAK sites were co-transfected into CHO cell-derived stable cell lines that has been engineered to have pAF-RS and pAF-tRNA plus anti-PSMA gene or fragment thereof. 72 hours after transfection, genomic DNA was isolated and a portion of the BAK locus was PCR amplified using oligos of SEQ ID NO: 45 and 46 as described in Example 8. BAX locus was PCR amplified using oligos of SEQ ID NO: 43 and 44 instead. DNA analysis of BAX and BAK deficient anti-PSMA expressing clones was conducted as described in the above Examples. As shown in FIG. 15, a Surveyor assay was conducted to determine the knockout efficiency in anti-PSMA expressing cell populations based on CRISPR editing technology. The ratio of the original band before and after CRISPR KO was used to measure the knockout efficiency. The knockout efficiency for Bax and Bak was 42% and 53% respectively, resulting in the calculated double knockout efficiency of approximately 20%.

Seven days later, the transfected pool of cells was subcloned at a seeding density of 1 cell/well into 40 plates using FACS. Approximately 1000 image-confirmed, single-cell derived clones were selected and screened through 96-well, 24-well and 24-deep well for productivity, growth and genotyping by targeted DNA sequencing.

DNA analysis of BAX and BAK deficient anti-PSMA expressing clones was conducted as described in Example 8 (data not shown). The top KO183 BAX/BAK double KO clones (KO183 BB KO) were selected for further assessment of growth and productivity by 2-month stability study and for confirmation of knockout status by western blotting.

Figure 16A:
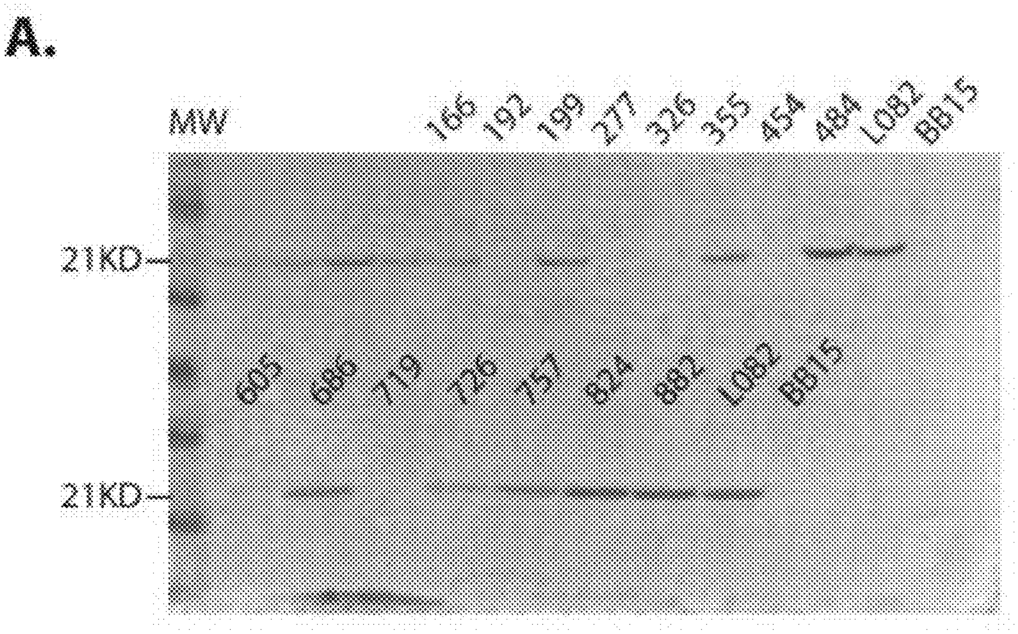
FIG. 16A-FIG. 16B. Western blot analysis of BAX and BAK knockout confirmation in anti-PSMA expressing clones. BAX knockout confirmation in anti-PSMA expressing clones using CRISPR (FIG. 16A). BAK knockout confirmation in anti-PSMA expressing clones (FIG. 16B). Controls are L082 cells that express wild type BAX protein, band at 21-KD and anti-HER2 expressing BB15 cells—BAX/BAK double knockout.
Figure 16B:
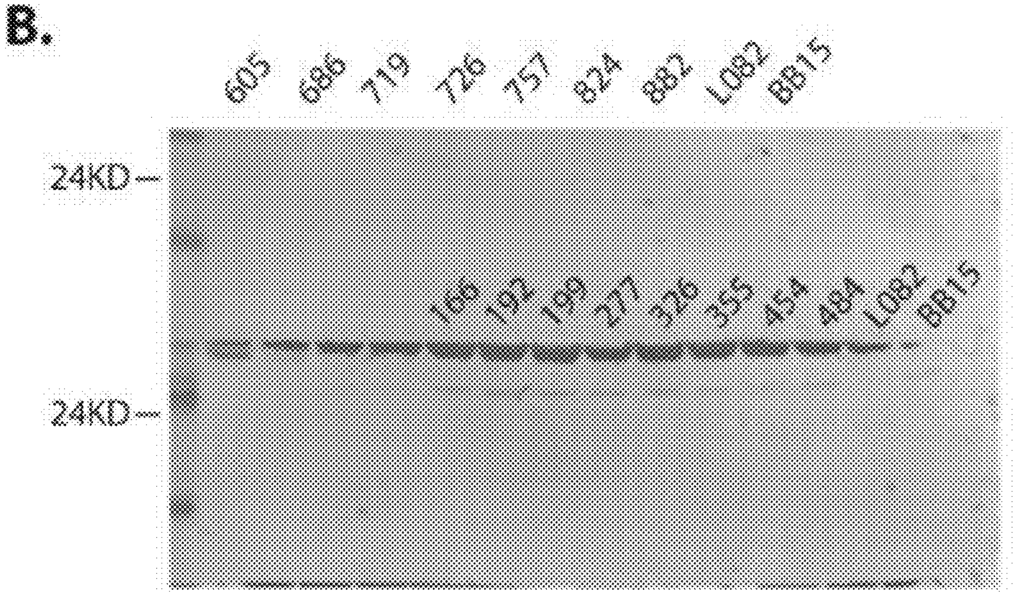
Figure 17A:
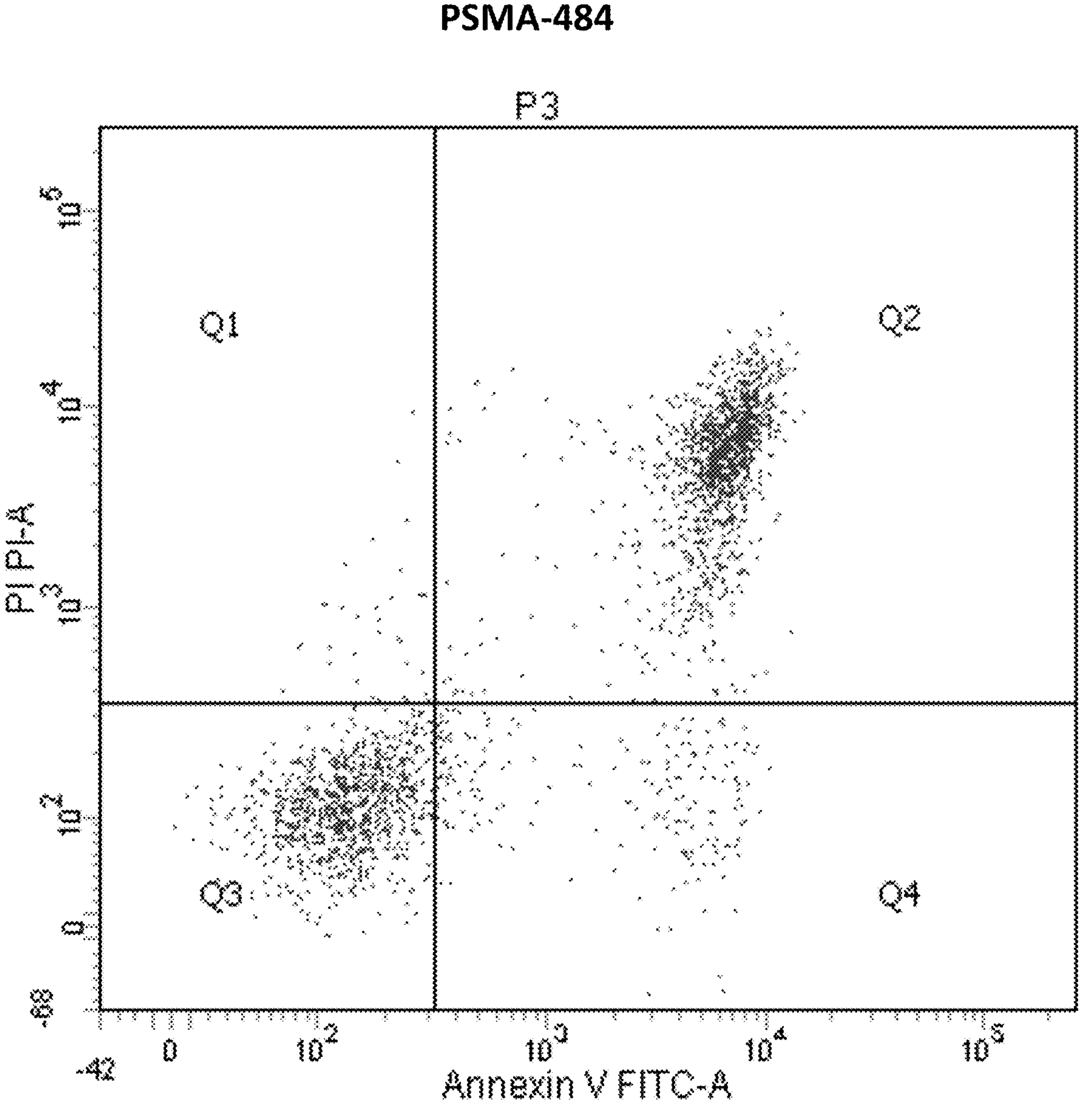
Figure 17B:
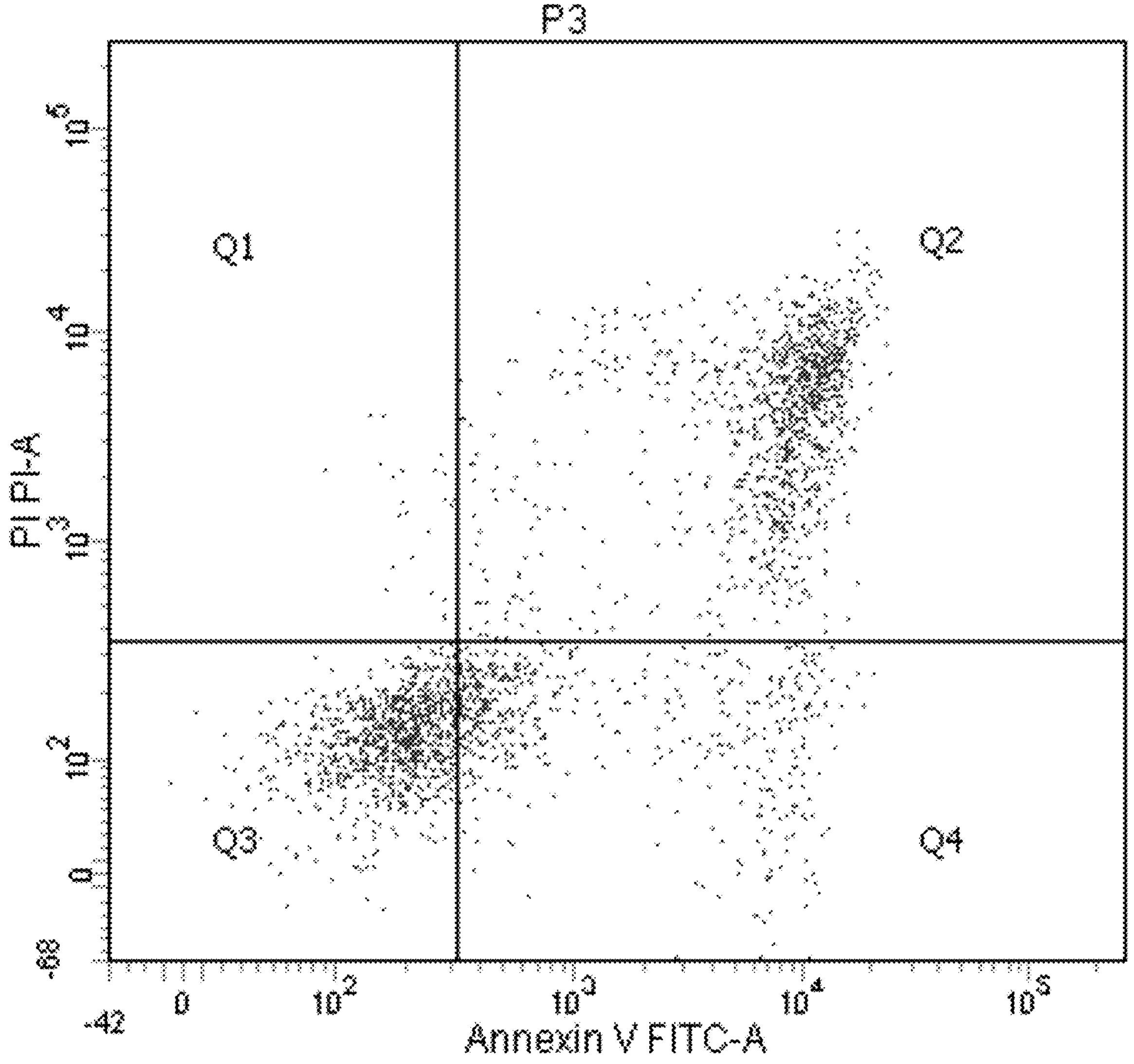
Figure 17C:
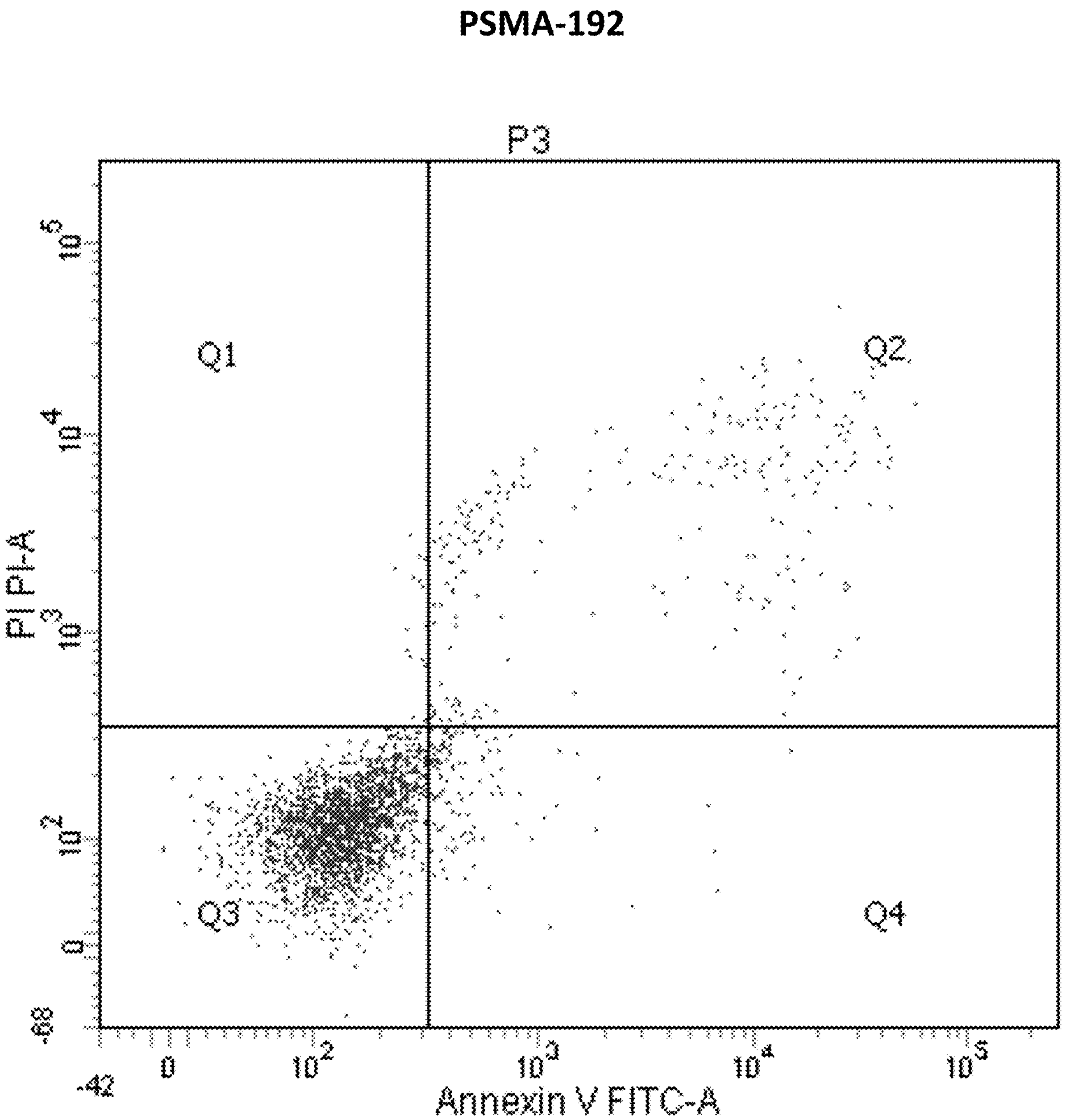
Figure 17D:
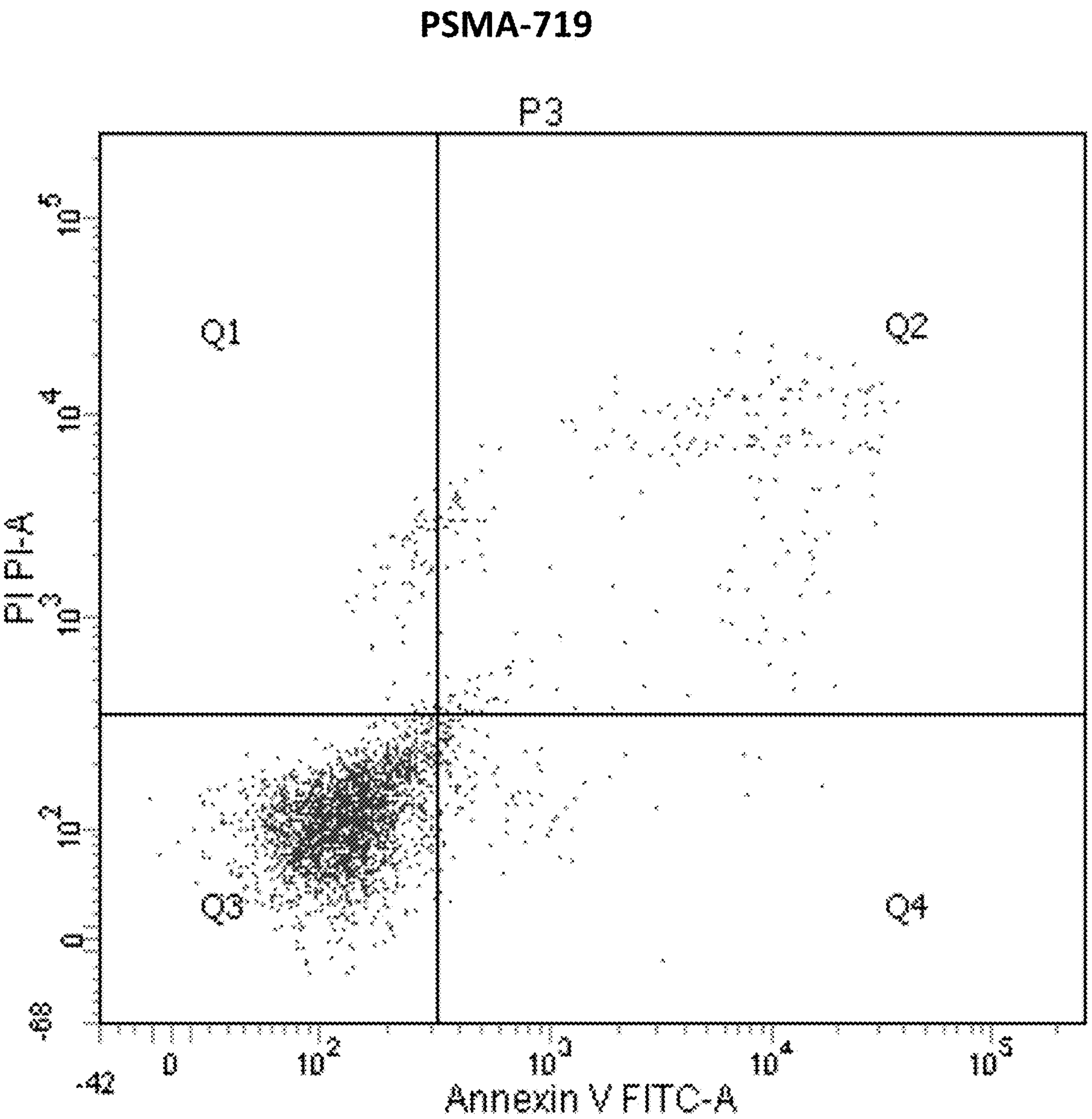

As shown in FIG. 16A and FIG. 16B, protein analysis of BAX and BAK knockout in anti-PSMA expressing clones was assessed by using Western Blot. Lysates from 6 million BAX/BAK double knockout cell lines were prepared by resuspending in 100 ul RIPA buffer (Abcam) plus protease inhibitors (Sigma tablets; Sigma). Lysates were incubated on ice for 1 hour before being centrifuged at 12,000 rpm for 20 minutes. Protein concentration was determined by BCA kit (Pierce). 20 ug of protein was used for Western blot. Protein extracts from different cell lines were probed with anti-BAX antibody (Abcam).

FIG. 16A, shows BAX knockout in anti-PSMA expressing clones engineered using CRISPR. FIG. 16B, BAK knockout in anti-PSMA expressing clones engineered using CRISPR. Of the top 15 clones depicted, 5 were BAX/BAK double knockouts. L082 is a positive control cell line expressing wild type or full-length BAX, a 21 KD protein and wild-type BAK, a 24 KD protein. Anti-HER2 expressing BB15 cells were used as double knockout control.

An analysis of apoptosis was further conducted in anti-PSMA expressing clones of the invention by Annexin-V binding apoptosis assay. As depicted in FIG. 17A, FIG. 17B, FIG. 17C, FIG. 17D and FIG. 17E, BAX/BAK double knockout clones, for example PSMA-192 and PSMA-719, showed cell viability of about 85%, compared to approximately 35-37% observed in single knockout clones, for example PSMA-882 and non-knockout clones for example PSMA-484.

Example 14: Production of Recombinant Protein is Increased in BAX/BAK Deficient Anti-PSMA Expressing Clones Based on the analysis of the anti-PSMA expressing BAX and BAK clones by western blotting and Annexin V analysis, a number of stable clones were selected for further optimization. Three (3) stable clones 192, 719 (both having BAX/BAK knockout) and 882 (BAK knockout) were selected for process optimization to improve titer based on high productivity, robust growth and 2-month stability observed for each.

Production of antibody was evaluated in fed-batch process as depicted in FIG. 18A, FIG. 18B and FIG. 18C. Under fed-batch culture conditions, BAX/BAK double knockout cell line (PSMA-BBKO-192) showed 3-fold increase in titer (1400 mg/L vs. 500 mg/L), (FIG. 18C) at day 10 of production. Simultaneously, the viability was also significantly improved (FIG. 18B) greater than 90%. The non-engineered cell line PSMA-S-164 was used as a control.

Example 15: Product Quality of BAX/BAK Deficient Anti-PSMA Expressing Cell Lines Product quality was analyzed by intact mass spectrometry (MS) and size exclusion chromatography (SEC) using samples produced by fed-batch production from anti-PSMA expressing control cell line (PSMA-S-164), and BAX/BAK double knockout anti-PSMA expressing cell line (PSMA-BBKO-192) as disclosed in Table 5. It was observed by MS that the primary amino acid sequence of the engineered clone and parental cell line is the same as deduced from the cDNA sequence confirming the identification of the mAb, (data not shown).

TABLE 5

Quality analyses of product from anti-PSMA expressing cell lines

| | SEC | | | nrCE-SDS | | | Intact Mass (% Glycoform) | | | | | |
|---|---|---|---|---|---|---|---|---|---|---|---|---|
| | HMW | Main | LMW | Main | Frag. | HMW | mAB | Man5 | G0 | G0F | G1F | G2F |
| PSMA-BBKO-192 | 3.2% | 94.7% | 2.1% | 96.5% | 3.5% | 0% | 0.2% | 0% | 1% | 77% | 21% | 2% |
| PSMA-S-164 | 2.4% | 97.6% | 0% | 96.1% | 3.8% | 0% | 0.5% | 1% | 1% | 64% | 29% | 5% |

As shown in Table 5, the glycoform profiles assessed by MS were comparable between non-engineered (PSMA-S-164) and BAX/BAK double knockout cell line (PSMA-BBKO-192) and within the normal distribution range for mAb at clone selection stage. SEC measured the percentage of high molecular weight (HMW) aggregates and nrCE-SDS measured the percentage of low molecular weight (LMW) degraded species. Both the HMW aggregates and LMW degraded species were lower than 5% and comparable between anti-PSMA expressing non-engineered and engineered cell lines. These quality profiles indicate that the CRISPR-Cas9 engineering and subsequent single cell cloning have not adversely impacted the product quality of anti-PSMA expressing cell lines.

Example 16: Generation of BAX/BAK Deficient Anti-CD70 Expressing Cell Line

Simultaneous ablation of BAX and BAK using CRISRP-Cas9 editing technology was performed by transfection of three BAX targeted gRNA constructs and two BAK targeted gRNA constructs into anti-CD70 expressing mini-pool cell population (CD70-MW-108). The BAX and BAK constructs used in this experiment were designed and prepared as described in the above Examples and illustrated in FIG. 5, FIG. 6 and FIG. 7 and Tables 1-3. CRISPR plasmids used in the knockout experiments relating to anti-CD70 were also designed as shown in FIG. 7 using a commercially available vector, Geneart CRISPR Nuclease Vector (pGCNV), (Thermo Fisher Scientific). The oligo duplex inserted into pGCNV, comprised five (5) pairs of synthetized oligos of SEQ ID Nos: 83 to SEQ ID No:92.

Figure 19:
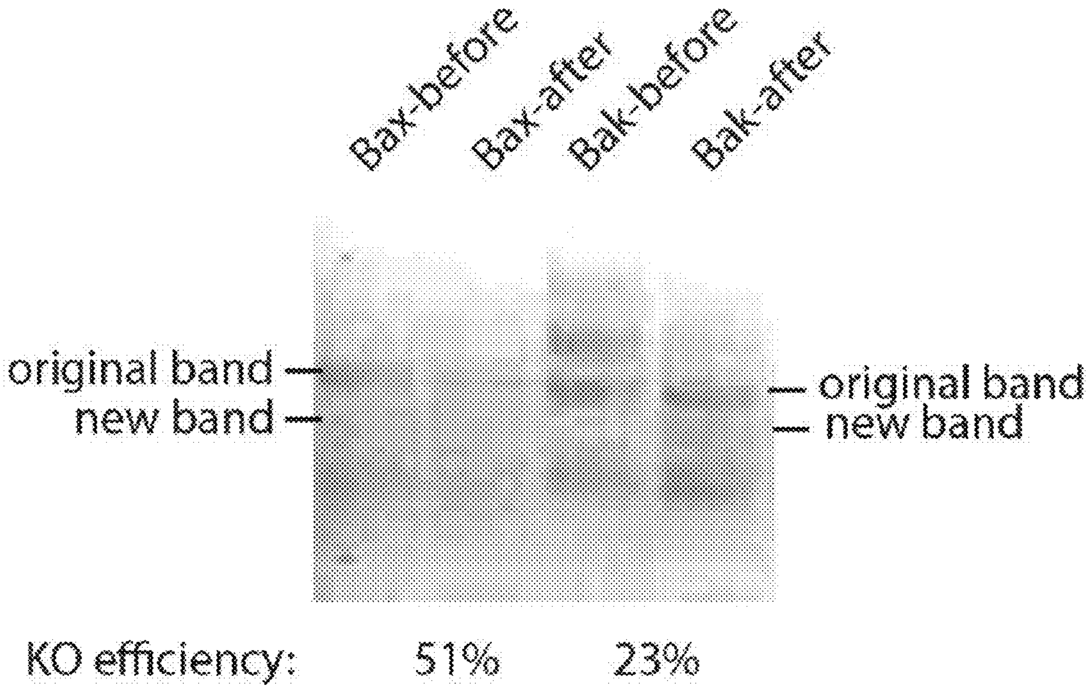
FIG. 19. Surveyor assay of anti-CD70 expressing cell populations in which BAX or BAK was knocked out using CRISPR. Surveyor assay analysis of knockout efficiency during BAX or BAK knockout using CRISPR is depicted. The ratio of the original band before and after CRISPR knockout (KO) was quantified by densitometry analysis of the scanned image by Image J software and used to measure the knockout efficiency. The knockout efficiency for BAX and BAK was 51% and 23% respectively, resulting in the calculated double knockout efficiency of approximately 10%.

Three plasmids encoding three different gRNA sequences targeting BAX sites and two plasmids encoding two different gRNA sequences targeting BAK sites were co-transfected into CHO cell-derived stable cell lines that has been engineered to have pAF-RS and pAF-tRNA plus anti-PSMA gene or fragment thereof. 72 hours after transfection, genomic DNA was isolated and a portion of the BAK locus was PCR amplified using oligos of SEQ ID NO: 45 and 46 as described in Example 5. BAX locus was PCR amplified using oligos of SEQ ID NO: 43 and 44 instead. As shown in FIG. 19, a Surveyor assay was conducted to determine the knockout efficiency in anti-CD70 expressing cell populations based on CRISPR editing technology. The ratio of the original band before and after CRISPR KO was quantified by densitometry analysis of the scanned image by Image J software and used to measure the knockout efficiency. The knockout efficiency for BAX and BAK was 51% and 23% respectively, resulting in the calculated double knockout efficiency of approximately 10%. A nonspecific band was observed in this assay. It is believed that this band may be due to the mini-pool nature of the cell population.

Seven days later, the transfected pool of cells was subcloned at a seeding density of 1 cell/well into 40 plates using FACS. Approximately 1000 image-confirmed, single-cell derived clones were selected and screened through 96-well, 24-well and 24-deep well for productivity, growth and genotyping by targeted DNA sequencing. DNA analysis of BAX and BAK deficient anti-CD70 expressing clones was conducted as described in Example 8 (data not shown). From the number of anti-CD70 expressing clones generated, the BAX/BAK double knockout clones, were selected for further assessment of growth and productivity by 2-month stability study and for confirmation of knockout status by western blotting.

Figure 20A:
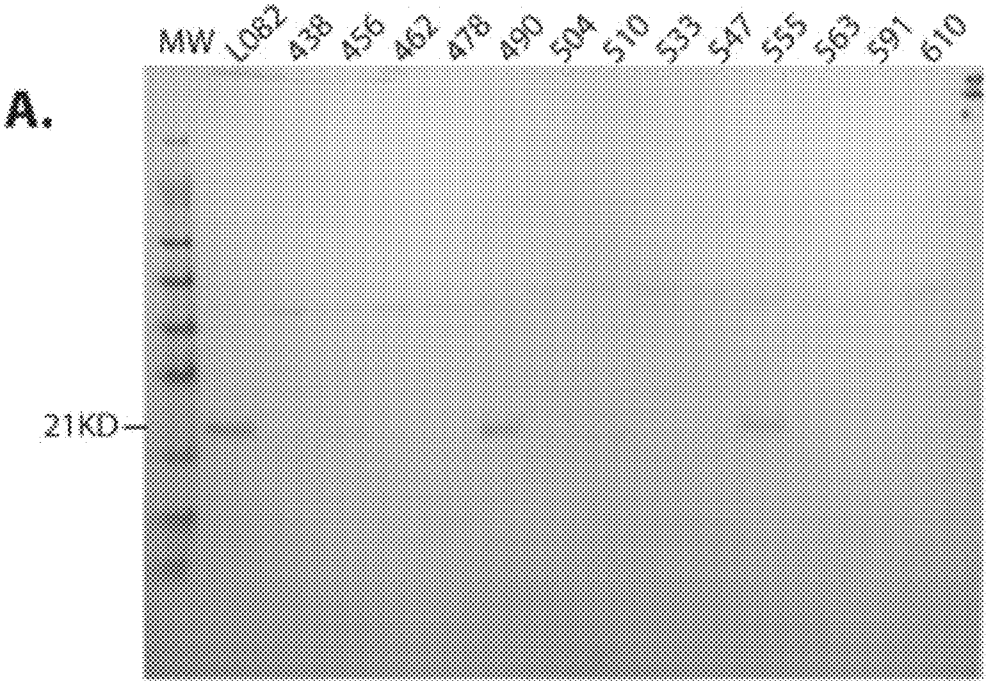
FIG. 20A-FIG. 20B. Western blot analysis of BAX and BAK knockout confirmation in anti-CD70 expressing clones. BAX knockout confirmation in anti-CD70 expressing clones (FIG. 20A). BAK knockout confirmation in anti-CD70 expressing clones (FIG. 20B). Control L082 cells expressing wild type BAX protein, band at 21-KD, and BAK wild type protein, band at 24 KD.
Figure 20B:
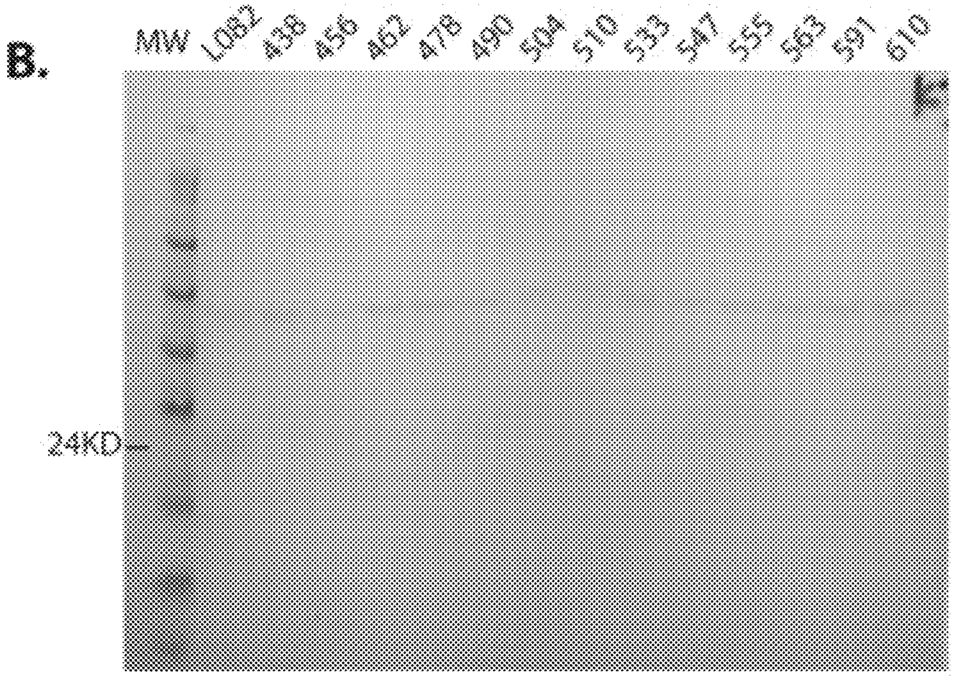

As shown in FIG. 20A and FIG. 20B, protein analysis of BAX and BAK knockout in anti-CD70 expressing clones was assessed by using Western Blot. Lysates from 6 million BAX/BAK double knockout cell lines were prepared by resuspending in 100 ul RIPA buffer (Abcam) plus protease inhibitors (Sigma tablets; Sigma). Lysates were incubated on ice for 1 hour before being centrifuged at 12,000 rpm for 20 minutes. Protein concentration was determined by BCA kit (Pierce). 20 ug of protein was used for Western blot. Protein extracts from different cell lines were probed with anti-BAX antibody (Abcam). FIG. 20A, shows BAX knockout in anti-CD70 expressing clones engineered using CRISPR. As shown in FIG. 20B, BAK knockout in anti-CD70 expressing clones engineered using CRISPR was observed in a number of clones. Of the top 13 clones depicted, 8 were BAX/BAK double knockouts. It is noted that the clone 108 parental cell line retained residual BAK protein expression. L082 is a positive control cell line expressing wild type or full-length BAX, a 21-KD protein and BAK wild type protein, band at 24 KD.

Figure 21A:
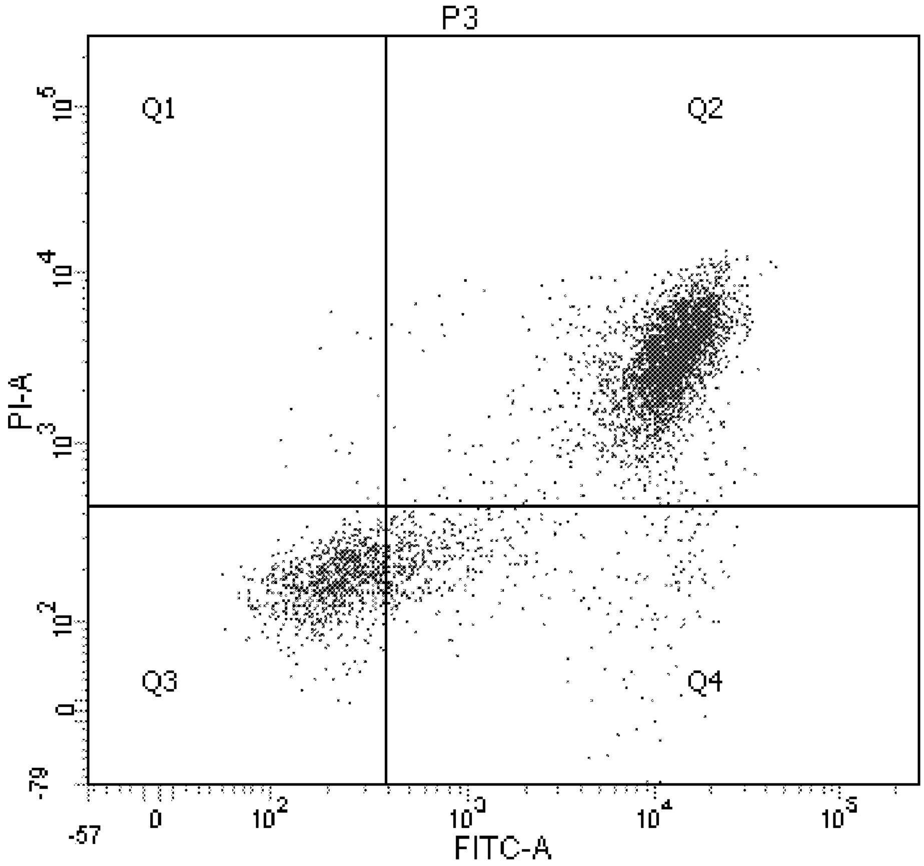
FIG. 21A-FIG. 21C. Apoptosis analysis of BAX/BAK knockout anti-CD70 expressing cell lines. Annexin V apoptosis analysis of BAX/BAK double knockout cell line CD70-BBKO-563 (FIG. 21B), for example, with cell viability of 60% compared to parental cell line CD70-MW-108 (FIG. 21A) with cell viability of 18%, are depicted, as summarized in FIG. 21C. Apoptotic cells decreased from 80% to 40%.
Figures 21B, 21C:
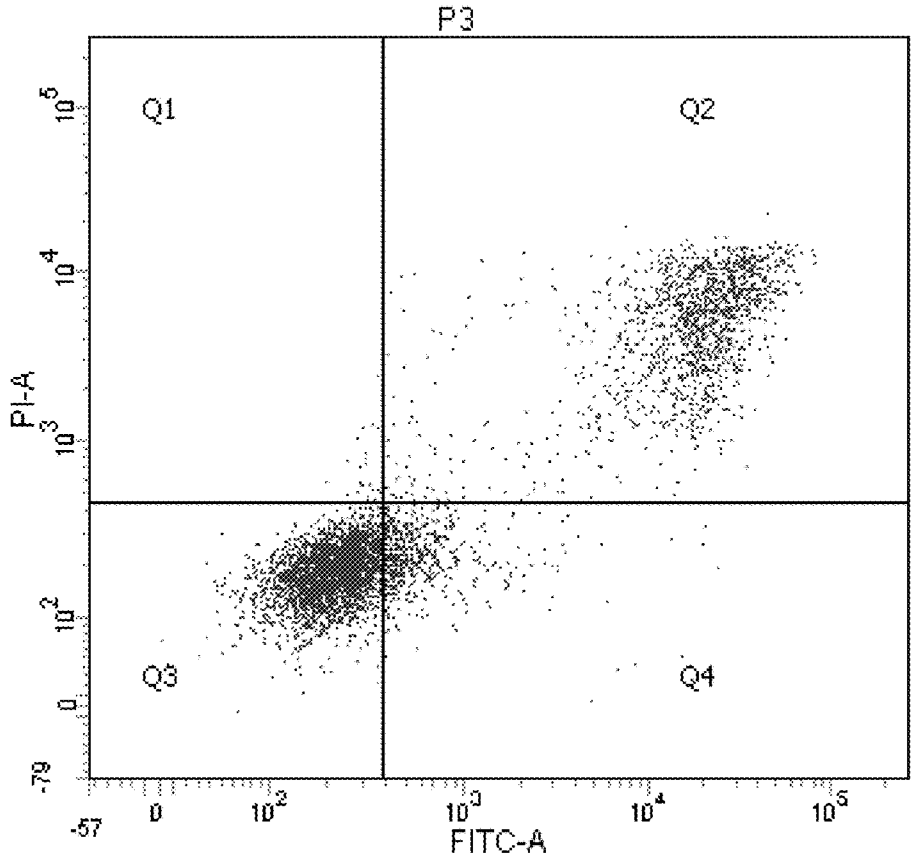

An analysis of apoptosis was further conducted in anti-CD70 expressing clones of the invention by Annexin-V binding apoptosis assay. As depicted in FIG. 21A, FIG. 21B and FIG. 21C, BAX/BAK double knockout clones, for example CD70-BBKO-563, showed cell viability of about 60%, compared to approximately 18% observed in the parental cell line CD70-MW-108. Simultaneously, the apoptotic cells decreased from 80% to 40% as observed from Q2 and Q4 for each cell line.

Example 17: Production of Recombinant Protein is Increased in BAX/BAK Deficient Anti-CD70 Expressing Clones Based on the analysis of the anti-CD70 expressing BAX and BAK clones by western blotting and Annexin V analysis, a number of stable clones were selected for further optimization. As depicted in FIG. 21A, FIG. 21B and FIG. 21C, nine (9) of the stable clones with both BAX/BAK knockout, were selected for process optimization to improve titer based on high productivity, robust growth and 2-month stability observed for each.

Figure 22A:
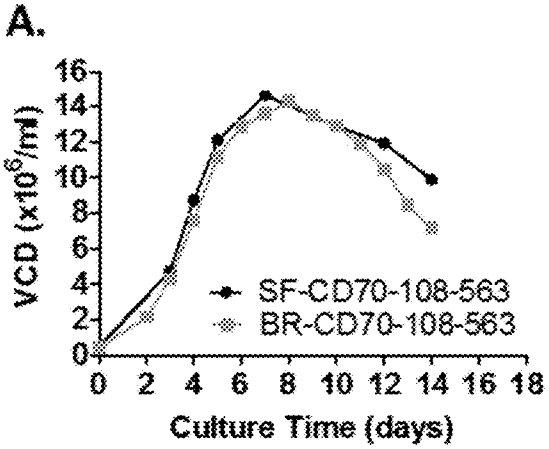
FIG. 22A-FIG. 22C. Promotion in anti-CD70 antibody production in BAX/BAK knockout cell lines in fed-batch culture. The production profiles of BAX/BAK double knockout anti-CD70 expressing cell lines in shake flask and bench top bioreactor are depicted. Viable Cell Density (VCD, FIG. 22A). Cell Viability (FIG. 22B). As an example, BAX/BAK double knockout cell line, CD70-BBKO-563, showed high titer of 1000 mg/L (FIG. 22C).
Figure 22B:
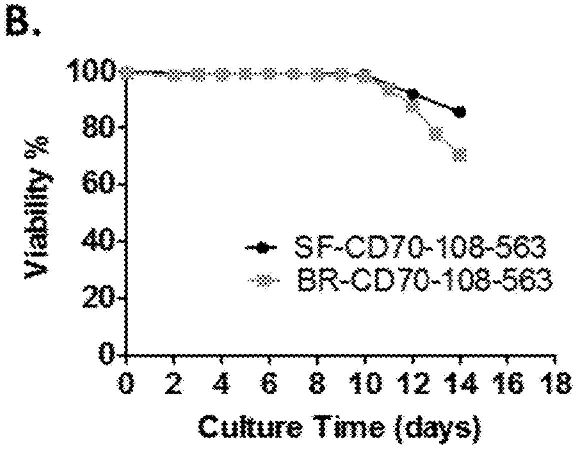
Figure 22C:
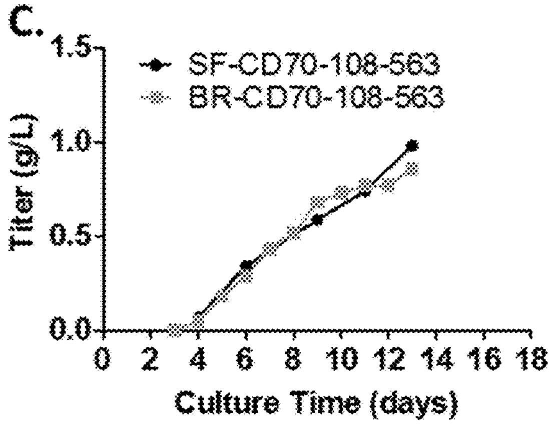

Production of antibody was evaluated in fed-batch process as depicted in FIG. 22A, FIGS. 22B and 22C. Under fed-batch culture conditions, anti-CD70 expressing BAX/BAK double knockout cell line (CD70-BBKO-563) showed titer of 1000 mg/L in both shaker flask and bench top bioreactor conditions, (FIG. 22C) at day 14 of production. The cell viability under both shaker flask and bench top bioreactor conditions (FIG. 22B) was about 90%. Overall, the production profile, VCD, viability and titer under the shaker flask and bioreactor conditions were comparable and support that the process is scalable. Further studies were conducted under the bioreactor conditions and processes based on the comparable productivity and growth profile analyzed (data not shown). This study supports the embodiment of the present invention to control apoptotic stressors that affect cell growth under conditions of a bioreactor by using CRISPR technology to knockout genes controlling or regulating apoptosis.

Example 18: Product Quality of BAX/BAK Deficient Anti-CD70 Expressing Cell Lines Product quality was analyzed by intact mass spectrometry (MS) and size exclusion chromatography (SEC) using samples produced by fed-batch production from anti-CD70 expressing BAX/BAK double knockout cell lines under bioreactor and shaker flask conditions as disclosed in Table 6.

TABLE 6

Quality analyses of product from anti-CD70 expressing cell lines

| | SEC | | | Intact Mass (% Glycoform) | | | | |
|---|---|---|---|---|---|---|---|---|
| | HMW | Main | LMW | Man5 | G0 | G0F | G1F | G2F |
| Shake Flask | 7.7% | 90.7% | 1.6% | 1.5% | 1.7% | 68.7% | 22.8% | 5.4% |
| Bio-reactor | 6.9% | 92.1% | 1.1% | 1.8% | 2.3% | 63.3% | 28.7% | % |

As shown in Table 5, the glycoform profiles assessed by MS were comparable between the shaker flask and bioreactor conditions and were within the normal distribution range for mAb at clone selection stage. SEC measured the percentage of high molecular weight (HMW) aggregates and the percentage of low molecular weight (LMW) degraded species. Both the HMW aggregates and LMW degraded species were within the normal range at the clone selection stage. The slightly higher than 5% HMW was observed to be reduced to 2-3% after purification (data not shown). These quality profiles indicate that CRISPR and subsequent single cell cloning have not adversely impacted the product quality of anti-CD70 expressing cell lines. It was also noted that the product quality attributes, (aggregates, integrity and glycoforms), in the bioreactor conditions matched the counterparts in shaker flask conditions proving that the process is scalable.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions disclosed and described herein belong. Although any methods, devices, and materials similar or equivalent to those described herein can be used in the practice or testing of the inventions described herein, the preferred methods, devices and materials are now described.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described herein can be used in various combinations. It is understood that the examples and embodiments described herein are for illustrative purposes only and that various modifications or changes in light thereof will be suggested to persons skilled in the art and are to be included within the spirit and purview of this application and scope of the appended claims.

INCORPORATION BY REFERENCE

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of generating a cell line for incorporating a non-natural amino acid into a protein, the method comprising inactivating one or more target site or region in a cell, wherein the one or more target site or region is Bak, Bax, or both; wherein the cell expresses a selector codon containing gene of interest, and wherein the cell comprises an orthogonal aminoacyl tRNA synthetase and an orthogonal suppressor transfer RNA (tRNA).

2. The method of claim 1, wherein the cell line is a eukaryotic cell line.

3. The method of claim 1, wherein the cell line is COS, Chinese hamster ovary (CHO), VERO, Madin-Darby canine kidney (MDCK), WI38, V79, B14AF28-G3, baby hamster kidney (BHK), hamster kidney (HaK), NS0, SP2/0-Ag14, HeLa, or human embryonic kidney (HEK293).

4. The method of claim 1, wherein the cell line generated by the method is resistant to apoptosis.

5. The method of claim 1, wherein the gene of interest is a biotherapeutic gene.

6. The method of claim 5, wherein the biotherapeutic gene is a vaccine.

7. The method of claim 1, wherein the gene of interest encodes an antibody, single chain variable fragment (ScFv), scFv fusion protein, fragment crystallizable (Fc) fusion protein, Factor VII, Factor VIII, or Factor IV.

8. The method of claim 1, wherein the gene of interest encodes an antibody.

9. The method of claim 1, wherein the gene of interest encodes a cytokine, interleukin, interferon, chemokine, growth factor or hormone; or a receptor or bispecific thereof.

10. The method of claim 1, wherein the gene of interest encodes Human epidermal growth factor receptor 2 (HER2), Cluster of Differentiation 70 (CD-70), Prostate-specific membrane antigen (PSMA), Trophoblast glycoprotein (5T4), Epidermal growth factor receptor (EGFR), Trophoblast cell surface antigen 2 (TROP2), Cluster of differentiation 3 (CD3), Interleukin-2 (IL-2), Interleukin-3 (IL-3), Interleukin-10 (IL-10), Interleukin-15 (IL-15), Glypican-3 (GPC3), Delta-like ligand 3 (DLL3), Receptor Tyrosine Kinase-like Orphan Receptor 1 (ROR1) leptin, Fibroblast Growth Factor 21 (FGF-21), Fibroblast Growth Factor 23 (FGF-23), human growth hormone (HGH), Fc receptor (FcR), insulin, Tumor Necrosis Factor Receptor 1 (TNFR1), TNF-related apoptosis-inducing ligand (TRAIL) or erythropoietin (EPO); or a receptor or bispecific thereof.

11. The method of claim 1, wherein the one or more target site or region Bak.

12. The method of claim 1, wherein the one or more target site or region is Bax.

13. The method of claim 1, wherein the one or more target site or region is Bak and Bax.

14. The method of claim 1, wherein the one or more target site or region is at least 30% inactivated.

15. The method of claim 1, wherein the selector codon is a nonsense codon, a rare codon, or a four-base codon.

16. The method of claim 15, wherein the selector codon is a nonsense codon, wherein the nonsense codon comprises an ochre codon, an opal codon, or an amber codon.

17. The method of claim 1, further comprising introducing a nucleic acid selected from the group consisting of SEQ ID NOs: 1 to 6 into the cell, wherein the nucleic acid is capable of inactivating the one or more target site or region in the cell.

18. The method of claim 1, wherein the cell line is a transient cell line, a stable cell line population or a stable clonal cell line.

19. The method of claim 18, wherein the cell line is a stable cell line population, and the stable cell line population is a platform cell line or a production cell line.

20. A cell or cell line for incorporating a non-natural amino acid into a protein, wherein the cell or cell line expresses a selector codon-containing gene of interest, wherein the cell or cell line comprises an orthogonal aminoacyl tRNA synthetase, and an orthogonal suppressor tRNA; and wherein the cell or cell line comprises one or more inactivated target site or region, wherein the one or more inactivated target site or region is Bak, Bax, or both.

21. A method comprising:

(i) generating a cell or cell line for incorporating a non-natural amino acid into a protein, comprising:
  providing a cell or cell line expressing a selector codon-containing gene of interest, and comprising an orthogonal aminoacyl tRNA synthetase and an orthogonal suppressor tRNA; and
  inactivating one or more target site or region in the cell or cell line, wherein the one or more target site or region is Bak, Bax, or both; and (ii) producing the protein comprising the non-natural amino acid.

22. The method of claim 21, wherein the one or more target site or region is Bak.

23. The method of claim 21, wherein the one or more target site or region is Bax.

24. The method of claim 21, wherein the one or more target site or region is Bak and Bax.

25. The method of claim 21, wherein producing the protein comprising the non-natural amino acid comprises providing a non-natural amino acid to the cell or cell line generated by the method, wherein the non-natural amino acid is incorporated into the protein.

26. The method of claim 21, wherein the yield of the protein comprising the non-natural amino acid is from 0.5-fold to 10-fold greater than the yield of the protein in the absence of the inactivation of the one or more target site or region.

27. The method of claim 21, wherein the non-natural amino acid is an O-methyl-L-tyrosine, an L-3-(2-naphthyl) alanine, a 3-methyl-phenylalanine, an O-4-allyl-L-tyrosine, a 4-propyl-L-tyrosine, p-propargyloxy-L-phenylalanine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, or an isopropyl-L-phenylalanine, para-acetyl phenylalanine, p-nitrophenylalanine, p-sulfotyrosine, p-carboxyphenylalanine, an o-nitrophenylalanine, an m-nitrophenylalanine, a p-boronyl phenylalanine, an o-boronylphenylalanine, an m-boronylphenylalanine, a p-aminophenylalanine, an o-aminophenylalanine, an m-aminophenylalanine, a p-acylphenylalanine, an o-acylphenylalanine, an m-acylphenylalanine, a p-OMe phenylalanine, an o-OMe phenylalanine, an m-OMe phenylalanine, a p-sulfophenylalanine, an o-sulfophenylalanine, an m-sulfophenylalanine, a 5-nitro histidine (His), a 3-nitro tyrosine (Tyr) a 2-nitro Tyr, a nitro substituted leucine (Leu) Leu, a nitro substituted His, a nitro substituted tryptophan (Trp), a 2-nitro Trp, a 4-nitro Trp, a 5-nitro Trp, a 6-nitro Trp, a 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-carboxyphenylalanine, p-acetyl-L-phenylalanine, a p-propargylphenylalanine, O-methyl-L-tyrosine, an L-3-(2-naphthyl) alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine or a p-propargyloxyphenylalanine.

* * * * *

SEQUENCE LISTING

```
Sequence total quantity: 115
SEQ ID NO: 1           moltype = DNA  length = 19
FEATURE                Location/Qualifiers
source                 1..19
                       mol_type = other DNA
                       organism = Cricetulus griseus
SEQUENCE: 1
aggcactcgc tcaacttct                                                   19

SEQ ID NO: 2           moltype = DNA  length = 19
FEATURE                Location/Qualifiers
source                 1..19
                       mol_type = other DNA
                       organism = Cricetulus griseus
SEQUENCE: 2
tgagtgtgac cggctgttg                                                   19

SEQ ID NO: 3           moltype = DNA  length = 19
FEATURE                Location/Qualifiers
source                 1..19
                       mol_type = other DNA
                       organism = Cricetulus griseus
SEQUENCE: 3
tttcatccag tatcgagct                                                   19

SEQ ID NO: 4           moltype = DNA  length = 19
FEATURE                Location/Qualifiers
source                 1..19
                       mol_type = other DNA
                       organism = Cricetulus griseus
SEQUENCE: 4
gaacaaattg tccatctcg                                                   19

SEQ ID NO: 5           moltype = DNA  length = 19
FEATURE                Location/Qualifiers
source                 1..19
                       mol_type = other DNA
```

-continued

```
                        organism = Cricetulus griseus
SEQUENCE: 5
atgctgtaag aacgggagt                                              19

SEQ ID NO: 6            moltype = DNA  length = 19
FEATURE                 Location/Qualifiers
source                  1..19
                        mol_type = other DNA
                        organism = Cricetulus griseus
SEQUENCE: 6
gaagccggtc aaaccacgt                                              19

SEQ ID NO: 7            moltype = DNA  length = 19
FEATURE                 Location/Qualifiers
source                  1..19
                        mol_type = other DNA
                        organism = Cricetulus griseus
SEQUENCE: 7
tcatggattg gccagtaac                                              19

SEQ ID NO: 8            moltype = DNA  length = 19
FEATURE                 Location/Qualifiers
source                  1..19
                        mol_type = other DNA
                        organism = Cricetulus griseus
SEQUENCE: 8
ccactgggcg agacggtgc                                              19

SEQ ID NO: 9            moltype = DNA  length = 19
FEATURE                 Location/Qualifiers
source                  1..19
                        mol_type = other DNA
                        organism = Cricetulus griseus
SEQUENCE: 9
gaagcaccgg tcctggatc                                              19

SEQ ID NO: 10           moltype = DNA  length = 19
FEATURE                 Location/Qualifiers
source                  1..19
                        mol_type = other DNA
                        organism = Cricetulus griseus
SEQUENCE: 10
agctctgtag gtggcgcac                                              19

SEQ ID NO: 11           moltype = DNA  length = 19
FEATURE                 Location/Qualifiers
source                  1..19
                        mol_type = other DNA
                        organism = Cricetulus griseus
SEQUENCE: 11
tgacatatgc ctcggtaat                                              19

SEQ ID NO: 12           moltype = DNA  length = 19
FEATURE                 Location/Qualifiers
source                  1..19
                        mol_type = other DNA
                        organism = Cricetulus griseus
SEQUENCE: 12
taatcggtgg accccgaat                                              19

SEQ ID NO: 13           moltype = DNA  length = 20
FEATURE                 Location/Qualifiers
source                  1..20
                        mol_type = other DNA
                        organism = Cricetulus griseus
SEQUENCE: 13
aacaggagta tactctcttg                                             20

SEQ ID NO: 14           moltype = DNA  length = 21
FEATURE                 Location/Qualifiers
source                  1..21
                        mol_type = other DNA
                        organism = Cricetulus griseus
SEQUENCE: 14
cgccagacaa agcctatcgc a                                           21

SEQ ID NO: 15           moltype = DNA  length = 20
FEATURE                 Location/Qualifiers
source                  1..20
```

```
                         mol_type = other DNA
                         organism = Cricetulus griseus
SEQUENCE: 15
agcctacgat cccaaggggg                                                20

SEQ ID NO: 16            moltype = DNA  length = 19
FEATURE                  Location/Qualifiers
source                   1..19
                         mol_type = other DNA
                         organism = Cricetulus griseus
SEQUENCE: 16
gcctcctcga tgtgcctgg                                                 19

SEQ ID NO: 17            moltype = DNA  length = 19
FEATURE                  Location/Qualifiers
source                   1..19
                         mol_type = other DNA
                         organism = Cricetulus griseus
SEQUENCE: 17
cattgtccag gtccccctt                                                 19

SEQ ID NO: 18            moltype = DNA  length = 19
FEATURE                  Location/Qualifiers
source                   1..19
                         mol_type = other DNA
                         organism = Cricetulus griseus
SEQUENCE: 18
acaatgcccg tcgtctgac                                                 19

SEQ ID NO: 19            moltype = DNA  length = 19
FEATURE                  Location/Qualifiers
source                   1..19
                         mol_type = other DNA
                         organism = Cricetulus griseus
SEQUENCE: 19
tgaccctgtt catcagcgc                                                 19

SEQ ID NO: 20            moltype = DNA  length = 19
FEATURE                  Location/Qualifiers
source                   1..19
                         mol_type = other DNA
                         organism = Cricetulus griseus
SEQUENCE: 20
tcagcgcggt ccaggacca                                                 19

SEQ ID NO: 21            moltype = DNA  length = 19
FEATURE                  Location/Qualifiers
source                   1..19
                         mol_type = other DNA
                         organism = Cricetulus griseus
SEQUENCE: 21
tccaggacca ggtggtgcc                                                 19

SEQ ID NO: 22            moltype = DNA  length = 19
FEATURE                  Location/Qualifiers
source                   1..19
                         mol_type = other DNA
                         organism = Cricetulus griseus
SEQUENCE: 22
tcgatgagct gatgctttg                                                 19

SEQ ID NO: 23            moltype = DNA  length = 19
FEATURE                  Location/Qualifiers
source                   1..19
                         mol_type = other DNA
                         organism = Cricetulus griseus
SEQUENCE: 23
agctgatgct ttgggccga                                                 19

SEQ ID NO: 24            moltype = DNA  length = 19
FEATURE                  Location/Qualifiers
source                   1..19
                         mol_type = other DNA
                         organism = Cricetulus griseus
SEQUENCE: 24
gaggactgcc ccgaagtcc                                                 19

SEQ ID NO: 25            moltype = DNA  length = 19
FEATURE                  Location/Qualifiers
```

```
source                  1..19
                        mol_type = other DNA
                        organism = Cricetulus griseus
SEQUENCE: 25
ggcggtgttc gccgagatc                                                 19

SEQ ID NO: 26           moltype = DNA  length = 19
FEATURE                 Location/Qualifiers
source                  1..19
                        mol_type = other DNA
                        organism = Cricetulus griseus
SEQUENCE: 26
ccgagatcgg cccgcgcat                                                 19

SEQ ID NO: 27           moltype = DNA  length = 19
FEATURE                 Location/Qualifiers
source                  1..19
                        mol_type = other DNA
                        organism = Cricetulus griseus
SEQUENCE: 27
gcgcatggcc gagttgagc                                                 19

SEQ ID NO: 28           moltype = DNA  length = 19
FEATURE                 Location/Qualifiers
source                  1..19
                        mol_type = other DNA
                        organism = Cricetulus griseus
SEQUENCE: 28
cagggcctcg gccgagcct                                                 19

SEQ ID NO: 29           moltype = DNA  length = 19
FEATURE                 Location/Qualifiers
source                  1..19
                        mol_type = other DNA
                        organism = Cricetulus griseus
SEQUENCE: 29
cccgctgccg cccccctgt                                                 19

SEQ ID NO: 30           moltype = DNA  length = 19
FEATURE                 Location/Qualifiers
source                  1..19
                        mol_type = other DNA
                        organism = Cricetulus griseus
SEQUENCE: 30
ggcttgggga tgccctgcg                                                 19

SEQ ID NO: 31           moltype = DNA  length = 19
FEATURE                 Location/Qualifiers
source                  1..19
                        mol_type = other DNA
                        organism = Cricetulus griseus
SEQUENCE: 31
tacatcatcg cccagtgtg                                                 19

SEQ ID NO: 32           moltype = DNA  length = 19
FEATURE                 Location/Qualifiers
source                  1..19
                        mol_type = other DNA
                        organism = Cricetulus griseus
SEQUENCE: 32
agcttcttct tgaattcgc                                                 19

SEQ ID NO: 33           moltype = DNA  length = 19
FEATURE                 Location/Qualifiers
source                  1..19
                        mol_type = other DNA
                        organism = Cricetulus griseus
SEQUENCE: 33
atgaagacga agagggtca                                                 19

SEQ ID NO: 34           moltype = DNA  length = 19
FEATURE                 Location/Qualifiers
source                  1..19
                        mol_type = other DNA
                        organism = Cricetulus griseus
SEQUENCE: 34
agatgcccat attattggc                                                 19

SEQ ID NO: 35           moltype = DNA  length = 19
```

```
FEATURE                Location/Qualifiers
source                 1..19
                       mol_type = other DNA
                       organism = Cricetulus griseus
SEQUENCE: 35
atctggactc agacccctt                                                    19

SEQ ID NO: 36          moltype = DNA  length = 19
FEATURE                Location/Qualifiers
source                 1..19
                       mol_type = other DNA
                       organism = Cricetulus griseus
SEQUENCE: 36
gcaggcaatg cattggact                                                    19

SEQ ID NO: 37          moltype = DNA  length = 19
FEATURE                Location/Qualifiers
source                 1..19
                       mol_type = other DNA
                       organism = Cricetulus griseus
SEQUENCE: 37
ctctttttgg cacgctcca                                                    19

SEQ ID NO: 38          moltype = DNA  length = 19
FEATURE                Location/Qualifiers
source                 1..19
                       mol_type = other DNA
                       organism = Cricetulus griseus
SEQUENCE: 38
atccacagtg aatttgtgc                                                    19

SEQ ID NO: 39          moltype = DNA  length = 19
FEATURE                Location/Qualifiers
source                 1..19
                       mol_type = other DNA
                       organism = Cricetulus griseus
SEQUENCE: 39
cgttttgccc gtttaagaa                                                    19

SEQ ID NO: 40          moltype = DNA  length = 20
FEATURE                Location/Qualifiers
source                 1..20
                       mol_type = other DNA
                       organism = Cricetulus griseus
SEQUENCE: 40
gcagatatgt tattctccgc                                                   20

SEQ ID NO: 41          moltype = DNA  length = 20
FEATURE                Location/Qualifiers
source                 1..20
                       mol_type = other DNA
                       organism = Cricetulus griseus
SEQUENCE: 41
gatccgtcca caaccttggc                                                   20

SEQ ID NO: 42          moltype = DNA  length = 20
FEATURE                Location/Qualifiers
source                 1..20
                       mol_type = other DNA
                       organism = Cricetulus griseus
SEQUENCE: 42
gataaactgc aatctggttg                                                   20

SEQ ID NO: 43          moltype = DNA  length = 20
FEATURE                Location/Qualifiers
source                 1..20
                       mol_type = other DNA
                       organism = Cricetulus griseus
SEQUENCE: 43
agggttatga gcctccctag                                                   20

SEQ ID NO: 44          moltype = DNA  length = 20
FEATURE                Location/Qualifiers
source                 1..20
                       mol_type = other DNA
                       organism = Cricetulus griseus
SEQUENCE: 44
ggctaccatg taaagagacc                                                   20
```

```
SEQ ID NO: 45           moltype = DNA  length = 19
FEATURE                 Location/Qualifiers
source                  1..19
                        mol_type = other DNA
                        organism = Cricetulus griseus
SEQUENCE: 45
cagacagcct tctcttgct                                              19

SEQ ID NO: 46           moltype = DNA  length = 20
FEATURE                 Location/Qualifiers
source                  1..20
                        mol_type = other DNA
                        organism = Cricetulus griseus
SEQUENCE: 46
agagctcctg agaggcatga                                             20

SEQ ID NO: 47           moltype = DNA  length = 19
FEATURE                 Location/Qualifiers
source                  1..19
                        mol_type = other DNA
                        organism = Cricetulus griseus
SEQUENCE: 47
tttcacgctg tgacaccca                                              19

SEQ ID NO: 48           moltype = DNA  length = 20
FEATURE                 Location/Qualifiers
source                  1..20
                        mol_type = other DNA
                        organism = Cricetulus griseus
SEQUENCE: 48
cagaaccaca ccaagaattg                                             20

SEQ ID NO: 49           moltype = DNA  length = 20
FEATURE                 Location/Qualifiers
source                  1..20
                        mol_type = other DNA
                        organism = Cricetulus griseus
SEQUENCE: 49
tgtttaggac cttcggtttc                                             20

SEQ ID NO: 50           moltype = DNA  length = 20
FEATURE                 Location/Qualifiers
source                  1..20
                        mol_type = other DNA
                        organism = Cricetulus griseus
SEQUENCE: 50
atgtcaaggg cactatagac                                             20

SEQ ID NO: 51           moltype = DNA  length = 19
FEATURE                 Location/Qualifiers
source                  1..19
                        mol_type = other DNA
                        organism = Cricetulus griseus
SEQUENCE: 51
cccaacgcaa gagaccttc                                              19

SEQ ID NO: 52           moltype = DNA  length = 20
FEATURE                 Location/Qualifiers
source                  1..20
                        mol_type = other DNA
                        organism = Cricetulus griseus
SEQUENCE: 52
agagtgaacc tcagcgcacg                                             20

SEQ ID NO: 53           moltype = DNA  length = 20
FEATURE                 Location/Qualifiers
source                  1..20
                        mol_type = other DNA
                        organism = Cricetulus griseus
SEQUENCE: 53
agtgaaagag agaggagagg                                             20

SEQ ID NO: 54           moltype = DNA  length = 22
FEATURE                 Location/Qualifiers
source                  1..22
                        mol_type = other DNA
                        organism = Cricetulus griseus
SEQUENCE: 54
gatgaagtga agttgctcta cc                                          22
```

```
SEQ ID NO: 55          moltype = DNA  length = 20
FEATURE                Location/Qualifiers
source                 1..20
                       mol_type = other DNA
                       organism = Cricetulus griseus
SEQUENCE: 55
ctacgcaagg cacgaggttc                                                20

SEQ ID NO: 56          moltype = DNA  length = 20
FEATURE                Location/Qualifiers
source                 1..20
                       mol_type = other DNA
                       organism = Cricetulus griseus
SEQUENCE: 56
ataagcctct gctactccag                                                20

SEQ ID NO: 57          moltype = DNA  length = 21
FEATURE                Location/Qualifiers
source                 1..21
                       mol_type = other DNA
                       organism = Cricetulus griseus
SEQUENCE: 57
cacttgaaca aaggcatcaa g                                              21

SEQ ID NO: 58          moltype = DNA  length = 21
FEATURE                Location/Qualifiers
source                 1..21
                       mol_type = other DNA
                       organism = Cricetulus griseus
SEQUENCE: 58
tctcattgag aaggcatgtg c                                              21

SEQ ID NO: 59          moltype = DNA  length = 20
FEATURE                Location/Qualifiers
source                 1..20
                       mol_type = other DNA
                       organism = Cricetulus griseus
SEQUENCE: 59
gggaattcca aataggaccc                                                20

SEQ ID NO: 60          moltype = DNA  length = 20
FEATURE                Location/Qualifiers
source                 1..20
                       mol_type = other DNA
                       organism = Cricetulus griseus
SEQUENCE: 60
ctgctcggga aggttatgtt                                                20

SEQ ID NO: 61          moltype = DNA  length = 21
FEATURE                Location/Qualifiers
source                 1..21
                       mol_type = other DNA
                       organism = Cricetulus griseus
SEQUENCE: 61
atggccaagt tgaccagtgc c                                              21

SEQ ID NO: 62          moltype = DNA  length = 21
FEATURE                Location/Qualifiers
source                 1..21
                       mol_type = other DNA
                       organism = Cricetulus griseus
SEQUENCE: 62
tcagtcctgc tcctcggcca c                                              21

SEQ ID NO: 63          moltype = DNA  length = 21
FEATURE                Location/Qualifiers
source                 1..21
                       mol_type = other DNA
                       organism = Cricetulus griseus
SEQUENCE: 63
atgaaaaagc ctgaactcac c                                              21

SEQ ID NO: 64          moltype = DNA  length = 21
FEATURE                Location/Qualifiers
source                 1..21
                       mol_type = other DNA
                       organism = Cricetulus griseus
SEQUENCE: 64
```

```
tcattcctct gccctcggac g                                                21

SEQ ID NO: 65          moltype = DNA  length = 21
FEATURE                Location/Qualifiers
source                 1..21
                       mol_type = other DNA
                       organism = Cricetulus griseus
SEQUENCE: 65
atgaccgagt acaagcccac g                                                21

SEQ ID NO: 66          moltype = DNA  length = 21
FEATURE                Location/Qualifiers
source                 1..21
                       mol_type = other DNA
                       organism = Cricetulus griseus
SEQUENCE: 66
agtccgtggc ccgaacgccc a                                                21

SEQ ID NO: 67          moltype = DNA  length = 21
FEATURE                Location/Qualifiers
source                 1..21
                       mol_type = other DNA
                       organism = Cricetulus griseus
SEQUENCE: 67
ggcagcgcgt cagccccctg c                                                21

SEQ ID NO: 68          moltype = DNA  length = 21
FEATURE                Location/Qualifiers
source                 1..21
                       mol_type = other DNA
                       organism = Cricetulus griseus
SEQUENCE: 68
tcagtgccag ttttcttggc t                                                21

SEQ ID NO: 69          moltype = DNA  length = 21
FEATURE                Location/Qualifiers
source                 1..21
                       mol_type = other DNA
                       organism = Cricetulus griseus
SEQUENCE: 69
gctgaggggg cagcaagctg c                                                21

SEQ ID NO: 70          moltype = DNA  length = 21
FEATURE                Location/Qualifiers
source                 1..21
                       mol_type = other DNA
                       organism = Cricetulus griseus
SEQUENCE: 70
ctgcccagcc cgaggaggca g                                                21

SEQ ID NO: 71          moltype = DNA  length = 21
FEATURE                Location/Qualifiers
source                 1..21
                       mol_type = other DNA
                       organism = Cricetulus griseus
SEQUENCE: 71
atgaagctac tcgagaactc c                                                21

SEQ ID NO: 72          moltype = DNA  length = 21
FEATURE                Location/Qualifiers
source                 1..21
                       mol_type = other DNA
                       organism = Cricetulus griseus
SEQUENCE: 72
tttcatcctc accaccctgg c                                                21

SEQ ID NO: 73          moltype = DNA  length = 21
FEATURE                Location/Qualifiers
source                 1..21
                       mol_type = other DNA
                       organism = Cricetulus griseus
SEQUENCE: 73
caggtgggct cacatctttg c                                                21

SEQ ID NO: 74          moltype = DNA  length = 21
FEATURE                Location/Qualifiers
source                 1..21
                       mol_type = other DNA
                       organism = Cricetulus griseus
```

-continued

```
SEQUENCE: 74
tcacatacag atcactggaa c                                            21

SEQ ID NO: 75          moltype = DNA  length = 21
FEATURE                Location/Qualifiers
source                 1..21
                       mol_type = other DNA
                       organism = Cricetulus griseus
SEQUENCE: 75
tcatactgtg ttgagtggga c                                            21

SEQ ID NO: 76          moltype = DNA  length = 21
FEATURE                Location/Qualifiers
source                 1..21
                       mol_type = other DNA
                       organism = Cricetulus griseus
SEQUENCE: 76
ccacactaga gagcccacaa c                                            21

SEQ ID NO: 77          moltype = DNA  length = 24
FEATURE                Location/Qualifiers
source                 1..24
                       mol_type = other DNA
                       organism = Cricetulus griseus
SEQUENCE: 77
atgccatcat atatcgtgag catc                                         24

SEQ ID NO: 78          moltype = DNA  length = 23
FEATURE                Location/Qualifiers
source                 1..23
                       mol_type = other DNA
                       organism = Cricetulus griseus
SEQUENCE: 78
aaacaagctt gttccctaac tag                                          23

SEQ ID NO: 79          moltype = DNA  length = 22
FEATURE                Location/Qualifiers
source                 1..22
                       mol_type = other DNA
                       organism = Cricetulus griseus
SEQUENCE: 79
aggagtgtag tgtagtgatg at                                           22

SEQ ID NO: 80          moltype = DNA  length = 21
FEATURE                Location/Qualifiers
source                 1..21
                       mol_type = other DNA
                       organism = Cricetulus griseus
SEQUENCE: 80
atttgctctg ctgccctaac t                                            21

SEQ ID NO: 81          moltype = DNA  length = 21
FEATURE                Location/Qualifiers
source                 1..21
                       mol_type = other DNA
                       organism = Cricetulus griseus
SEQUENCE: 81
tgacagcaat ggactgttct c                                            21

SEQ ID NO: 82          moltype = DNA  length = 22
FEATURE                Location/Qualifiers
source                 1..22
                       mol_type = other DNA
                       organism = Cricetulus griseus
SEQUENCE: 82
cagcttcagg atatgtaggg ta                                           22

SEQ ID NO: 83          moltype = DNA  length = 24
FEATURE                Location/Qualifiers
source                 1..24
                       mol_type = other DNA
                       organism = Cricetulus griseus
SEQUENCE: 83
aggcactcgc tcaacttcgg tttt                                         24

SEQ ID NO: 84          moltype = DNA  length = 24
FEATURE                Location/Qualifiers
source                 1..24
                       mol_type = other DNA
```

-continued

```
                        organism = Cricetulus griseus
SEQUENCE: 84
cgaagttgag cgagtgcctc ggtg                                            24

SEQ ID NO: 85           moltype = DNA  length = 24
FEATURE                 Location/Qualifiers
source                  1..24
                        mol_type = other DNA
                        organism = Cricetulus griseus
SEQUENCE: 85
tgagtgtgac cggctgttgg tttt                                            24

SEQ ID NO: 86           moltype = DNA  length = 25
FEATURE                 Location/Qualifiers
source                  1..25
                        mol_type = other DNA
                        organism = Cricetulus griseus
SEQUENCE: 86
caacagcgcc tcacactcac cggtg                                           25

SEQ ID NO: 87           moltype = DNA  length = 25
FEATURE                 Location/Qualifiers
source                  1..25
                        mol_type = other DNA
                        organism = Cricetulus griseus
SEQUENCE: 87
tttcatccat gtatcgagct gtttt                                           25

SEQ ID NO: 88           moltype = DNA  length = 25
FEATURE                 Location/Qualifiers
source                  1..25
                        mol_type = other DNA
                        organism = Cricetulus griseus
SEQUENCE: 88
agctcgatac tggatgaaga cggtg                                           25

SEQ ID NO: 89           moltype = DNA  length = 24
FEATURE                 Location/Qualifiers
source                  1..24
                        mol_type = other DNA
                        organism = Cricetulus griseus
SEQUENCE: 89
gaacaaattg tccatctcgg tttt                                            24

SEQ ID NO: 90           moltype = DNA  length = 24
FEATURE                 Location/Qualifiers
source                  1..24
                        mol_type = other DNA
                        organism = Cricetulus griseus
SEQUENCE: 90
cgagatggac aatttgttcc ggtg                                            24

SEQ ID NO: 91           moltype = DNA  length = 24
FEATURE                 Location/Qualifiers
source                  1..24
                        mol_type = other DNA
                        organism = Cricetulus griseus
SEQUENCE: 91
atgctgtaag aacgggagtg tttt                                            24

SEQ ID NO: 92           moltype = DNA  length = 25
FEATURE                 Location/Qualifiers
source                  1..25
                        mol_type = other DNA
                        organism = Cricetulus griseus
SEQUENCE: 92
cactcccgtt cttacagcat cggtg                                           25

SEQ ID NO: 93           moltype = DNA  length = 528
FEATURE                 Location/Qualifiers
source                  1..528
                        mol_type = other DNA
                        organism = Cricetulus griseus
SEQUENCE: 93
gggttatgag cctccctagc cccctcgctc ttcccggaac ctaggagtcc aggcactcct  60
tccctcctct ctccaccagg gcccaccagc tctgagcaga tcatgaagac aggggccttt  120
ttgctacagg ggtgagtgtg aggcgctgtt gtggtggggt gggcttcagg agcaaggctc  180
agttcccact ctgcgcctcc gtccccccgc ttccattcac atctagtttc atccagtatc  240
gagctgggag gatggccggg gatacacctg agctgacctt ggagcagcca ccccaggatc  300
```

-continued

```
cgaccaccaa gaagttgagc gagtgcctca ggcgaattgg agatgagctg gacagcaaca  360
tggagctgca gaggtgtggt tcctgggtcc tggggtccat ccggggattt cgtgttacct  420
caagaactca ggcatcgtac actcttgtcc tcccaaggga ccaggtgttc caccacttca  480
gatattccgt gctgggcata gaatccaggg tctctttaca tggtagcc                528

SEQ ID NO: 94           moltype = DNA  length = 740
FEATURE                 Location/Qualifiers
source                  1..740
                        mol_type = other DNA
                        organism = Cricetulus griseus
SEQUENCE: 94
cagacagcct tctcttgctg actcccagct ctgaccccag aacagcaggt ggcccaggac  60
acagaggagg tctttcgaag ctatgttttc catctccacc atcaggaaca agagacccag  120
ggggcggctg cccctgccaa ccccgagatg gacaatttgc tcctagaacc caacaggtaa  180
gctccagccc caggggggaca ggtcccgggg ggagggggac tggacttatc tctgtcatct  240
ctctcccttc tcaatctggt cccccccca tctgcagtcc tatactcctt tcaggacatg  300
cccgtcctgt ccttagcaca gccctcctgg ccactgtcga ggacgttggc ggtgcggggt  360
aaagtctgct cctacccccca ccccaggaga atccattctg tgccacgagc cgggttccca  420
atctccaact cccgttctta cagcatcttg ggtcaggtgg gccggcagct tgctatcatt  480
ggagatgaca ttaaccggag atacgacaca gagttccaga atttactgga gcagctgcag  540
cccacagctg ggaatgccta cgaactcttc accaagattg cctccaggta cccaccacca  600
cctgacccag cacacacgtg atgggctccc tggctgggga ccgagttcgt gaactcagat  660
acgatccccg cccatctccc cgtctctggg ccccactcgc tgtcttctgc atacttgctg  720
tcatgcctct caggagctct                                               740

SEQ ID NO: 95           moltype = DNA  length = 740
FEATURE                 Location/Qualifiers
source                  1..740
                        mol_type = other DNA
                        organism = Cricetulus griseus
SEQUENCE: 95
cagacagcct tctcttgctg actcccagct ctgaccccag aacagcaggt ggcccaggac  60
acagaggagg tctttcgaag ctatgttttc catctccacc atcaggaaca agagacccag  120
ggggcggctg cccctgccaa ccccgagatg gacaatttgc tcctagaacc caacaggtaa  180
gctccagccc caggggggaca ggtcccgggg ggagggggac tggacttatc tctgtcatct  240
ctctcccttc tcaatctggt cccccccca tctgcagtcc tatactcctt tcaggacatg  300
cccgtcctgt ccttagcaca gccctcctgg ccactgtcga ggacgttggc ggtgcggggt  360
aaagtctgct cctacccccca ccccaggaga atccattctg tgccacgagc cgggttccca  420
atctccaact cccgttctta cagcatcttg ggtcaggtgg gccggcagct tgctatcatt  480
ggagatgaca ttaaccggag atacgacaca gagttccaga atttactgga gcagctgcag  540
cccacagctg ggaatgccta cgaactcttc accaagattg cctccaggta cccaccacca  600
cctgacccag cacacacgtg atgggctccc tggctgggga ccgagttcgt gaactcagat  660
acgatccccg cccatctccc cgtctctggg ccccactcgc tgtcttctgc atacttgctg  720
tcatgcctct caggagctct                                               740

SEQ ID NO: 96           moltype = DNA  length = 708
FEATURE                 Location/Qualifiers
variation               1..3
                        note = n is a, c, g, or t
source                  1..708
                        mol_type = other DNA
                        organism = Cricetulus griseus
SEQUENCE: 96
nnntcgaaca ggaaaagcaa gtggcccagg acacagagga ggtctttcga agctatgttt  60
tccatctcca ccatcaggaa caagagaccc agggggcggc tgcccctgcc aaccccgatg  120
gacaatttgc tcctagaacc caacaggtaa gctccagccc caggggggaca ggtcccgggg  180
ggagggggac tggacttatc tctgtcatct ctctcccttc tcaatctggt cccccccca  240
tctgcagtcc tatactcctt tcaggacatg cccgtcctgt ccttagcaca gccctcctgg  300
ccactgtcga ggacgttggc ggtgcggggt aaagtctgct cctacccccca ccccaggaga  360
atccattctg tgccacgagc cgggttccca atctccaact tacagcatct tgggtcaggt  420
gggccggcag cttgctatca ttggagatga cattaaccgg agatacgaca cagagttcca  480
gaatttactg gagcagctgc agcccacagc tgggaatgcc tacgaactct tcaccaagat  540
tgcctccagg tacccaccac cacctgaccc agcacacacg tgatgggctc cctggctggg  600
gaccgagttc gtgaactcag atacgatccc cgcccatctc cccgtctctg ggccccactc  660
gctgtcttct gcatacttgc tgtcatgcct ctcagggagc tctaaagc                708

SEQ ID NO: 97           moltype = DNA  length = 702
FEATURE                 Location/Qualifiers
variation               2..3
                        note = n is a, c, g, or t
source                  1..702
                        mol_type = other DNA
                        organism = Cricetulus griseus
SEQUENCE: 97
anntggaacc actaaagcaa gtggccaagg acacagagga ggtctttcga agctatgttt  60
tccatctcca ccatcaggaa caagagaccc agggggcggc tgcccctgcc aaccccgatg  120
gacaatttgc tcctagaacc caacaggtaa gctccagccc caggggggaca ggtcccgggg  180
ggagggggac tggacttatc tctgtcatct ctctcccttc tcaatctggt cccccccca  240
tctgcagtcc tatactcctt tcaggacatg cccgtcctgt ccttagcaca gccctcctgg  300
```

```
ccactgtcga ggacgttggc ggtgcggggt aaagtctgct cctaccccca ccccaggaga  360
atccattctg tgccacgagc cgggttccca atctccaaca tcttgggtca ggtgggccgg  420
cagcttgcta tcattggaga tgacattaac cggagatacg acacagagtt ccagaattta  480
ctggagcagc tgcagcccac agctgggaat gcctacgaac tcttcaccaa gattgcctcc  540
aggtacccac caccacctga cccagcacac acgtgatggg ctccctgggc tggggaccga  600
gttcgtgaac tcagatacga tccccgccca tctccccgtc tctgggcccc actcgctgtc  660
ttctgcatac ttgctgggca tgcctctcag gagctctcaa ag                     702

SEQ ID NO: 98          moltype = DNA  length = 426
FEATURE                Location/Qualifiers
source                 1..426
                       mol_type = other DNA
                       organism = Cricetulus griseus
SEQUENCE: 98
tcttgtaaca gaaagcaggt ggcccaggac acagaggagg tctttcgaag ctatgttttc  60
catctccacc atcaggaaca agagacccag ggggcggctg cccctgccaa ccccgacccg  120
ttcttacagc atcttgggtc aggtgggccg gcagcttgct atcattggag atgacattaa  180
ccggagatac gacacagagt tccagaattt actggagcag ctgcagccca cagctgggaa  240
tgcctacgaa ctcttcacca agattgcctc caggtaccca ccaccacctg acccagcaca  300
cacgtgatgg gctccctggc tggggaccga gttcgtgaac tcagatacga tccccgccca  360
tctccccgtc tctgggcccc actcgctgtc ttctgcatac ttgctgtcat gcctctcagg  420
agctct                                                             426

SEQ ID NO: 99          moltype = DNA  length = 427
FEATURE                Location/Qualifiers
variation              1..3
                       note = n is a, c, g, or t
source                 1..427
                       mol_type = other DNA
                       organism = Cricetulus griseus
SEQUENCE: 99
nnnttgaaca agacagcagg tggcccagga cacagaggag gtctttcgaa gctatgtttt  60
ccatctccac catcaggaac aagagaccca gggggcggct gcccctgcca accccgaccc  120
gttcttacag catcttgggt caggtgggcc ggcagcttgc tatcattgga gatgacatta  180
accggagata cgacacagag ttccagaatt tactggagca gctgcagccc acagctggga  240
atgcctacga actcttcacc aagattgcct ccaggtaccc accaccacct gacccagcac  300
acacgtgatg ggctccctgg ctggggaccg agttcgtgaa ctcagatacg atccccgccc  360
atctccccgt ctctgggccc cactcgctgt cttctgcata cttgctgtca tgcctctcag  420
gagctct                                                            427

SEQ ID NO: 100         moltype = DNA  length = 717
FEATURE                Location/Qualifiers
source                 1..717
                       mol_type = other DNA
                       organism = Cricetulus griseus
SEQUENCE: 100
gctttgtacc agacgcaggt ggccaggaca cagaggaggt ctttcgaagc tatgttttcc  60
atctccacca tcaggaacaa gagacccagg gggcggctgc cctgccaac cccgacatta  120
accccgatat taacccgaga tacgacacct acttccccaa tttactggag ttccaaaatt  180
tactggagca gctgcacccc acacctggga atgcctacga actcttcacc aacattgcct  240
ccaggtaccc accaccacct gacccagcac acacgtgatg ggctccctgg ctggggaccg  300
agttcgtgaa ctcagatacg atccccgccc atctccccgt ctctgggccc cactcgctgg  360
cttctgcata cttgctgtca tgcctctcag gagctctcat cttgggtctt acagggtctt  420
gggcttggtg ggccgggaga ttgctatcat tggagatgac attaaccgga gatacattta  480
ctggatccac aatttactgg agcaggtaat gcccacagct gggaatgcct aattaactct  540
tcgtaccgat tgcctcctgg tacccaccac cacctgaccc gctccacacg tgatgggctc  600
cctggctggg gaccgagtta tccaactcca tatacgatcc cccgcccatc ccactcgtct  660
gtgggtccac tcgctgtctt ctgcatactt ggaggtcatg cctctcagga actcaaa     717

SEQ ID NO: 101         moltype = DNA  length = 712
FEATURE                Location/Qualifiers
source                 1..712
                       mol_type = other DNA
                       organism = Cricetulus griseus
SEQUENCE: 101
gcctggaaca gaacgcaggt ggccaggaca cagaggaggt ctttcgaagc tatgttttcc  60
atctccacca tcaggaacaa gagacccagg gggcggctgc cctgccaac cccgacccgt  120
tcttacggca tcttgggtca ggtgggccgg cagcttgcta tgattggaga tgacattaac  180
cggatatacg acacagagtt ccagaattta ctggagcagc tgcagcccac agctgggaat  240
gcctacgaac tcttcaccaa gattgcctcc aggtacccac caccacctga cccagcacac  300
acgtgatggg ctccctggct ggggaccgac ttcgcgaact caaatacgat ccccgcccat  360
ctccccgact ctgggcccca ctcgctgtct tctgcatact tgctgtcatg cctctatgga  420
gctctgtggg ccggcagctt gctatcattg gagatgacat taaccggaga tacgacacag  480
agttccagaa tttactggag cagctgcagc ccacagctgg gaatgcctac gaactcttca  540
ccaagattgc ctccaggtac ccaccaccac ctgacccagc acacacgtga tgggctccct  600
ggctggggac cgagttcgtg aactcagata cgatccccgc ccatctcccc gtctctgggc  660
cccactcgct gtcttctgca tacttgctgt catgcctcta gggagctcta ag          712

SEQ ID NO: 102         moltype = DNA  length = 432
```

-continued

```
FEATURE                Location/Qualifiers
source                 1..432
                       mol_type = other DNA
                       organism = Cricetulus griseus
SEQUENCE: 102
ccctttaccc gaaccgccat gtaggcgcag gacacagagg aggtctttcg aagctatgtt  60
ttccatctcc accatcagga acaagagacc cagggggcgg ctgcccctgc caaccccgac  120
ccgttcttac agcatcttgg gtcaggtggg ccggcagctt gctatcattg gagatgacat  180
taaccggaga tacgacacag agttccagaa tttactggag cagctgcagc ccacagctgg  240
gaatgcctac gaactcttca ccaagattgc ctccaggtac ccaccaccac ctgacccagc  300
acacacgtga tgggctccct ggctggggac cgagttcgtg aactcagata cgatccccgc  360
ccatctcccc gtctctgggc cccactcgct gtcttctgca tacttgctgt catgcctctc  420
aggagctcta cg                                                      432

SEQ ID NO: 103         moltype = DNA  length = 432
FEATURE                Location/Qualifiers
source                 1..432
                       mol_type = other DNA
                       organism = Cricetulus griseus
SEQUENCE: 103
ccttaacaat aagcaggtgg ccaggacaca gaggaggtct ttcgaagcta tgttttcctc  60
tccaccatcg ggaacaagag acccaggggg cggctgcccc tgccaacccc gagccgttct  120
taccgcatct tgggtccagg gggccggcag cttgctatta ttggaaaaga cattaaccgg  180
aaataccaca cagaattcca gaatttaatg gaacaactgc atcccacagc tgggaatgcc  240
taccaactct tcaccaacat tgcctcccgg gacccaccac cacctgaccc aacacacccc  300
tgatggggtc cctggctggg gaccgaattc ctgaactcag atacgatccc cggccatctc  360
cccgtctctg ggccccactc actatcctct gcatacttgc tgtcatggct ctccagaact  420
cttattctgc at                                                      432

SEQ ID NO: 104         moltype = DNA  length = 714
FEATURE                Location/Qualifiers
source                 1..714
                       mol_type = other DNA
                       organism = Cricetulus griseus
SEQUENCE: 104
gctgtcaacc caaaaagcag gggccaggac acagaggagg tctttcaagc tatgttttcc  60
atctccacca tcaggaacaa gagacccagg gggcggctgc ccctgccaac cccgagagtt  120
ggagattggg aacccggctc gtggcacaga atggattctc ctggggtggg ggtaggagca  180
gactttaccc cgcaccgcca acgtcctcga cagtggccag gagggctgtg ctaaggacag  240
gacgggcatg tcctgaaagg agtataggac tgcagatggg gggggacca gattgagaag   300
ggagagagat gacagagata agtccagtcc ccctccccc gggacctgtc cccctggggc   360
tggagcttac ctgttgggtt ctaggagcaa attgtccatc cccgttctta cagcatcttg  420
ggtcaggtgg gccggcagct tgctatcatt ggagatgaca ttaaccggag atacgacaca  480
gagttccaga atttactgga gcagctgcag cccacagctg ggaatgccta cgaactcttc  540
accaagattg cctccaggta cccaccacca cctgacccag cacacacgtg atgggctccc  600
tggctgggga ccgagttcgt gaactcagat acgatccccg cccatctccc cgtctctggg  660
ccccactcgc tgtcttctgc atacttgctg tcatgcctct cagggagctc ttaa        714

SEQ ID NO: 105         moltype = DNA  length = 713
FEATURE                Location/Qualifiers
variation              1
                       note = n is a, c, g, or t
source                 1..713
                       mol_type = other DNA
                       organism = Cricetulus griseus
SEQUENCE: 105
naccgcatac caaaaaaaac atggcaggac acagaggagg tctttcgaag ctatgttttc  60
catctccacc atcaggaaca agagacccag ggggcggctg cccctgccaa ccccgagatg  120
gacaatttgc tcctagaacc caacaggtaa gctccagccc cagggggaca ggtcccgggg  180
ggagggggac tggacttatc tctgtcatct ctctcccttc tcaatctggt cccccccca   240
tctgcagtcc tatactcctt tcaggacatg cccgtcctgt ccttagcaca gccctcctgg  300
ccactgtcga ggacgttggc ggtgcggggt aaagtctgct cctaccccca ccccaggaga  360
atccattctg tgccacgagc cgggttccca atctccaact cccgttctta cagcatcttg  420
ggtcaggtgg gccggcagct tgctatcatt ggagatgaca ttaaccggag atacgacaca  480
gagttccaga atttactgga gcagctgcag cccacagctg ggaatgccta cgaactcttc  540
accaagattg cctccaggta cccaccacca cctgacccag cacacacgtg atgggctccc  600
tggctgggga ccgagttcgt gaactcagat acgatccccg cccatctccc cgtctctggg  660
ccccactcgc tgtcttctgc atacttgctg tcatgcctct caggagctct gaa         713

SEQ ID NO: 106         moltype = DNA  length = 416
FEATURE                Location/Qualifiers
source                 1..416
                       mol_type = other DNA
                       organism = Cricetulus griseus
SEQUENCE: 106
cccccgccc caaaaagcat gccaggaaag aggagtcttc gaagttgttt cctctcccca   60
tcaggaacaa gagacccagg gggcggctgc ccctgccaac cccgagcccg ttcttacagc  120
atcttgggtc aggtgggccg gcagcttgct atcattggag atgacattaa ccggagatac  180
gacacagagt tccagaattt actggagcag ctgcagccca cagctgggaa tgcctacgaa  240
```

```
ctcttcacca agattgcctc caggtaccca ccaccacctg acccagcaca cacgtgatgg  300
gctccctggc tggggaccga gttcgtgaac tcagatacga tccccgccca tctccccgtc  360
tctgggcccc actcgctgtc ttctgcatac ttgctgtcat gcctctcagg agctct      416

SEQ ID NO: 107         moltype = DNA  length = 407
FEATURE                Location/Qualifiers
source                 1..407
                       mol_type = other DNA
                       organism = Cricetulus griseus
SEQUENCE: 107
actctccaac caaaaagcat ggcaggaaca gaggagtctt caactatgtt tcctctccac  60
catcaggaac aagagaccca gggggcggtg cccctgccaa ccccgacccg tcttgcctct  120
tgggtcaggt ggacgtccct tgctaggtga cagtgaagga gcaggagaaa cgaaccaaac  180
ttcctcaatt tactgcagcc tctgctccca cacctgggaa tgcctacgaa ctcttcacca  240
agattgcctc caggtaccca ccaccacctg acccaccaca cacgtgatgg gctccctggc  300
tggggaccga ttcctgaact cacatacgat ccccgcccat ctccccggtc tgggacccac  360
tcttgtcttc tgcatacttg ctgtcatgcc tctcgggagc tctcact                407

SEQ ID NO: 108         moltype = DNA  length = 558
FEATURE                Location/Qualifiers
variation              2
                       note = n is a, c, g, or t
source                 1..558
                       mol_type = other DNA
                       organism = Cricetulus griseus
SEQUENCE: 108
ancctctacc aaaacgcatg gcaggacaca gaggaggtct ttcgaagcta tgttttccat  60
ctccaccatc aggaacaaga gacccagggg gcggctgccc ctgccaaccc cgacgcggga  120
ttacagcatc ctgggtcacg tgggccggca gcttgctatc attggagatg acattagccg  180
aagataacag gcataattcc tgaatttact ggaccatctg cagcccacac ctgggaatgc  240
ctacgaactc ttcaccaaga ttgcctccag gtacccacca ccacctgacc catcacacac  300
gtgatgggct ccctggctgg ggaccgagtt cgtgaactca gatacgatcc ccgcccatct  360
ccccgtctct gggccccact cgctgccttc tgcatacttg ctgtcatgcc tctcaggagc  420
tctggcagct tgctatcatt ggagatgaca ttaaccggag atacgacaca gagttccaga  480
atttactgga gcagctgcag cccacagctg ggaatgccta cgaactcttc accaggattg  540
cctccaggta cccaacca                                                 558

SEQ ID NO: 109         moltype = DNA  length = 637
FEATURE                Location/Qualifiers
source                 1..637
                       mol_type = other DNA
                       organism = Cricetulus griseus
SEQUENCE: 109
acctccgaaa aagaaaacgc aatggccagg aacagaggag gtctttcgaa gctatgtttt  60
ccatctccac catcaggaac aagagaccca gggggcggct gcccctgcca accccgagat  120
ggacaatttg ctcctaaaac ccaacaggta agctccagcc ccaggggac aggtcccggg  180
gggaggggga ctggacttat ctctgtcatc tctctccctt ctcaatctgg tccccccccc  240
atctgcagtc ctatactcct ttcaggacat gcccgtcctg tccttagcac agccctcctg  300
gccactgtcg aggacgttgg cggtgcgggg taaagtctgc tcctaccccc accccaggag  360
aatccattct gtgccacgag ccgggttccc aatctccaac tcccgttctt acagcatctt  420
gggtcaggtg ggccggcagc ttgctatcat tggagatgac attaaccgga gatacgacac  480
agagttccag aatttactgg agcagctgca gcccacagct gggaatgcct acgaactctt  540
caccaagatt gcctccaggt acccaccacc acctgaccca gcacacacgt gatgggctcc  600
ctggctgggg acccgagttc gtgaactcag atacgat                            637

SEQ ID NO: 110         moltype = DNA  length = 713
FEATURE                Location/Qualifiers
variation              2
                       note = n is a, c, g, or t
source                 1..713
                       mol_type = other DNA
                       organism = Cricetulus griseus
SEQUENCE: 110
antgggaaca aaaaaagcca gtggccagga cacagaggag gtctttcgaa gctatgtttt  60
ccatctccac catcaggaac aagagaccca gggggcggct gcccctgcca accccgagat  120
ggacaatttg ctcctagaac ccaacaggta agctccagcc ccaggggac aggtcccggg  180
gggaggggga ctggacttat ctctgtcatc tctctccctt ctcaatctgg tccccccccc  240
atctgcagtc ctatactcct ttcaggacat gcccgtcctg tccttagcac agccctcctg  300
gccactgtcg aggacgttgg cggtgcgggg taaagtctgc tcctaccccc accccaggag  360
aatccattct gtgccacgag ccgggttccc aatctccaac tcccgttctt acagcatctt  420
gggtcaggtg ggccggcagc ttgctatcat tggagatgac attaaccgga gatacgacac  480
agagttccag aatttactgg agcagctgca gcccacagct gggaatgcct acgaactctt  540
caccaagatt gcctccaggt acccaccacc acctgaccca gcacacacgt gatgggctcc  600
ctggctgggg accgagttcg tgaactcaga tacgatcccc gcccatctcc ccgtctctgg  660
gccccactcg ctgtcttctg catacttgct gtcatgcctc tcaggagctc tga          713

SEQ ID NO: 111         moltype = DNA  length = 503
FEATURE                Location/Qualifiers
source                 1..503
```

-continued

```
                        mol_type = other DNA
                        organism = Cricetulus griseus
SEQUENCE: 111
acctttaacc ctaacgcatg ccaggacaca gaggaggtct ttcgaagcta tgttttccat  60
ctccaccatc aggaacaaga gacccagggg gcggctgccc ctgccaaccc cgacctggac  120
ttactgctcc tagagtccag tggccggtcc ttgctagggg gacagatgac ggggggaggg  180
ggactggaca gacttgccta ttttactgct tcagctgcgt gccccggctg gtaatgccta  240
ctaactatta ccctaaattg cctcccggca cccacctcca cctgttcctg cacacactgc  300
atgccctccc tggcagtgga cccaaactct tcactcagat accatccccg cccatctccc  360
cacctgaggg ccccactcgc tgtcttctgc atactttgtg gactgactct caggacctct  420
tacgatcccc gcccatctcc ccgtctctgg gccccactcg ctgtcttctg catacttgct  480
gtcatgcctc tcaggagctc tga                                          503

SEQ ID NO: 112          moltype = DNA  length = 696
FEATURE                 Location/Qualifiers
variation               3
                        note = n is a, c, g, or t
source                  1..696
                        mol_type = other DNA
                        organism = Cricetulus griseus
SEQUENCE: 112
gcnccgaacc aaacaccaca gtggcaggac acagaggagg tctttcgaag ctatgttttc  60
catctccacc atcaggaaca agagacccag gggcggctg ccccctgccaa tttgctccta  120
gaacccaaca ggtaagctcc agccccaggg ggacaggtcc cggggggagg gggactggac  180
ttatctctgt catctctctc ccttctcaat ctggtccccc ccccatctgc agtcctatac  240
tcctttcagg acatgcccgt cctgtcctta gcacagccct cctggccact gtcgaggacg  300
ttggcggtgc ggggtaaagt ctgctcctac ccccacccca ggagaatcca ttctgtgcca  360
cgagccgggt tcccaatctc caactcccgt tcttacagca tcttgggtca ggtgggccgg  420
cagcttgcta tcattggaga tgacattaac cggagatacg acacagagtt ccagaattta  480
ctggagcagc tgcagcccac agctgggaat gcctacgaac tcttcaccaa gattgcctcc  540
aggtacccac caccacctga cccagcacac acgtgatggg ctccctggct ggggaccgag  600
ttcgtgaact cagatacgat ccccgcccat ctccccgtct ctgggcccca ctcgctgtct  660
tctgcatact tgctgtcatg cctctcagga gctctg                            696

SEQ ID NO: 113          moltype = DNA  length = 672
FEATURE                 Location/Qualifiers
variation               2..3
                        note = n is a, c, g, or t
source                  1..672
                        mol_type = other DNA
                        organism = Cricetulus griseus
SEQUENCE: 113
gnnctttacc caaaaagcat gccaggacac agaggaggtc tttcaagcta tgttttccat  60
ctccaccatc aggaacaaga gacccagggg gcggctgccc ctgccaaccc cgacccgttc  120
ttacagcatc ttgggtcagg tgggccggcg gattgctatg attggagatg acattaaccg  180
gatataccac acagagttcc agaatttact ggagcagctg cagcccacag ctgggaatgc  240
ctacgaactc ttcaccaaga ttgcctccag gtacccacca ccacctgacc cagcacacac  300
gtgatgggct ccctggctgg ggaccgactt cccgaactca aatacgatcc ccgcccatct  360
ccccgtctct gggccccact cgctgtcttc tgcatacttg ctgtcatgcc tctcatgagc  420
tctgtgggcc ggcagcttgc tatcattgga gatgacatta accggagata cgacacagag  480
ttccagaatt tactggagca gctgcagccc acagctggga atgcctacga actcttcacc  540
aagattgcct ccaggtaccc accaccacct ggacccagca cacacgtgat gggctccctg  600
gctggggacc gagttcctga actcagatag gatccccgcc catctccccc cgtctctggg  660
cccccactcc gc                                                      672

SEQ ID NO: 114          moltype = DNA  length = 419
FEATURE                 Location/Qualifiers
source                  1..419
                        mol_type = other DNA
                        organism = Cricetulus griseus
SEQUENCE: 114
accccttaac cgaaaagcat ggcaggaaca gaggaggctt caagtatgtt tcctctccac  60
catcaggaac aagagaccca gggggcggct gcccctgcca accccgaccc gttcttacag  120
catcttgggt caggtgggcc ggcagcttgc tatcattgga gatgacatta accggagata  180
cgacacagag ttccagaatt tactggagca gctgcagccc acagctggga atgcctacga  240
actcttcacc aagattgcct ccaggtaccc accaccacct gacccagcac acacgtgatg  300
ggctccctgg ctggggaccg agttcgtgaa ctcagatacg atccccgccc atctccccgt  360
ctctgggccc cactcgctgt cttctgcata cttgctgtca tgcctctcag gagctctga   419

SEQ ID NO: 115          moltype = DNA  length = 713
FEATURE                 Location/Qualifiers
source                  1..713
                        mol_type = other DNA
                        organism = Cricetulus griseus
SEQUENCE: 115
gggacccgaa caaacgcatg gccaggacac agaggaggtc tttcgaagct atgttttcca  60
tctccaccat caggaacaag agacccaggg ggcggctgcc cctgccaacc ccgatgatgg  120
acaatttgct cctagaaccc aacaggtaag ctccagcccc agggggacag gtcccggggg  180
gagggggact ggacttatct ctgtcatctc tctcccttct caatctggtc cccccccat  240
```

-continued

```
ctgcagtcct atactccttt caggacatgc ccgtcctgtc cttagcacag ccctcctggc  300
cactgtcgag gacgttggcg gtgcggggta aagtctgctc ctacccccac cccaggagaa  360
tccattctgt gccacgagcc gggttcccaa tctccaactc ccgttcttac agcatcttgg  420
gtcaggtggg ccggcagctt gctatcattg gagatgacat taaccggaga tacgacacag  480
agttccagaa tttactggag cagctgcagc ccacagctgg gaatgcctac gaactcttca  540
ccaagattgc ctccaggtac ccaccaccac ctgacccagc acacacgtga tgggctccct  600
ggctggggac cgagttcgtg aactcagata cgatccccgc ccatctcccc gtctctgggc  660
cccactcgct gtcttctgca tacttgctgt catgcctctc aggagctctg aaa         713
```